United States Patent
Wagner

(10) Patent No.: US 11,529,414 B2
(45) Date of Patent: Dec. 20, 2022

(54) VIRAL VACCINES FOR IN VIVO EXPRESSION OF A NUCLEIC ACID ENCODING AN IMMUNOGENIC PEPTIDE AND METHODS OF USING THE SAME

(71) Applicant: ORBIS HEALTH SOLUTIONS, LLC, Greenville, SC (US)

(72) Inventor: Thomas E. Wagner, Greenville, SC (US)

(73) Assignee: ORBIS HEALTH SOLUTIONS, LLC, Greenville, SC (US)

( * ) Notice: Subject to any disclaimer, the term of this patent is extended or adjusted under 35 U.S.C. 154(b) by 0 days.

(21) Appl. No.: 16/909,311

(22) Filed: Jun. 23, 2020

(65) Prior Publication Data

US 2021/0393771 A1 Dec. 23, 2021

(51) Int. Cl.
| | |
|---|---|
| A61K 39/385 | (2006.01) |
| A61K 39/215 | (2006.01) |
| C12N 7/00 | (2006.01) |
| A61P 31/14 | (2006.01) |
| A61K 39/00 | (2006.01) |

(52) U.S. Cl.
CPC .......... *A61K 39/385* (2013.01); *A61K 39/215* (2013.01); *A61P 31/14* (2018.01); *C12N 7/00* (2013.01); *A61K 2039/53* (2013.01); *A61K 2039/54* (2013.01); *A61K 2039/6006* (2013.01); *C12N 2770/20034* (2013.01); *C12N 2770/20071* (2013.01)

(58) Field of Classification Search
None
See application file for complete search history.

(56) References Cited

U.S. PATENT DOCUMENTS

| | | | |
|---|---|---|---|
| 5,591,601 A | 1/1997 | Wagner et al. | |
| 5,635,380 A * | 6/1997 | Naftilan | A61K 9/1272 424/450 |
| 2009/0117658 A1 * | 5/2009 | Wagner | A61K 47/61 435/456 |
| 2010/0068808 A1 * | 3/2010 | Bangera | C01B 32/174 435/375 |
| 2010/0111985 A1 * | 5/2010 | Schwamberger | A61K 39/39 424/184.1 |
| 2010/0260797 A1 * | 10/2010 | Hanon | A61K 39/145 424/209.1 |

FOREIGN PATENT DOCUMENTS

| | | | |
|---|---|---|---|
| WO | WO-97/11605 A1 | | 4/1997 |
| WO | WO 00/11202 | * | 3/2000 |

OTHER PUBLICATIONS

Turunen et al. (MolecularTherapy. 2002; 6 (3): 306-312).*
Wagner et al. (PNAS. 1992; 89: 6099-6103).*
Mizuguchi et al. (Gene Therapy. 2001; 8: 730-735).*
Baklaushev et al. (Scientific Reports. 2017; 7.1: 1-17).*
Sequence alignment Seq ID No. 1 with Geneseq db acc No. BHT59643 by Qin et al May 1, 2020.*
Garofalo et al. (Vaccines. Jun. 10, 2020; 8: 293).*
Feng et al. (Nature Communications. 2020; 1 (1): 1-11).*
Pollet et al. (bioRxiv.Jan. 1, 2020 (not peer-reviewed)).*
Shen et al. (International Journal of Nanomedicine. 2017; 12: 5443-560).*
Curiel et al. (Human Gene Therapy. 1992; 31: 147-154).*
Shim et al. (BMC Immunology. 2010; 11: 65).*
Jaimes et al. (Journal of Molecular Biology. May 1, 2020; 432: 3309-3325).*
Chen et al. (Signal Transduction and Targeted Therapy. 2020; 5:180).*
Redding et al. ("DNA vaccines in veterinary use." Expert Review of Vaccines. 2009; 8 (9): 1251-1276).*
Sit et al. (Nature. Published online May 14, 2020; 586 (7831): 776-778).*
Argiolas et al., "Bombolitins, a New Class of Mast Cell Degranulating Peptides from the Venom of the Bumblebee *Megabombus pennsylvanicus*,"The Journal of Biological Chemistry, Feb. 10, 1985, 260(3):1437-1444.
Bal et al., "Adenovirus type 7 penton, Purification of soluble pentamers from *Escherichia coli* and development of an integrin-dependent gene delivery system," Eur. J. Biochem., 2000, 267:6074-6081.
Hammond et al., "A Particulate Viral Protein Vaccine Reduces Viral Load and Delays Progression to Disease in Immunized Ponies Challenged with Equine Infectious Anemia Virus," Virology, 1999, 254:37-49.
Lackey et al., "Enhancement of Cell Transfection Efficiency by a Biomimetic Membrane-disruptive Polymer in a Model Nonviral Targeted Delivery System," Abstracts of Scientific Presentations: The Third Annual Meeting of the American Society of Gene Therapy, Abstract No. 33, May 31, 2000-Jun. 4, 2000, Denver, Colorado.
Stayton et al., "Molecular engineering of proteins and polymers for targeting and intracellular delivery of therapeutics," Journal of Controlled Release, 2000, 65:203-220.

(Continued)

*Primary Examiner* — Shanon A. Foley
(74) *Attorney, Agent, or Firm* — Foley & Lardner LLP

(57) ABSTRACT

The present disclosure provides particles for delivering a nucleic acid that encodes an immunogenic peptide in an antigen presenting cell. The disclosed particles can function as a vaccine and can be used to treat or prevent a viral or bacterial infection in a subject by expressing in vivo an immunogenic peptide, thereby stimulating the subject's immune system to attack the virus or bacteria that naturally express the immunogenic peptide.

19 Claims, 13 Drawing Sheets

Specification includes a Sequence Listing.

(56) References Cited

OTHER PUBLICATIONS

Wagner et al,. "Influenza virus hemagglutinin HA-2 N-terminal fusogenic peptides augment gene transfer by transferrin-polylysine-DNA complexes: Toward a synthetic virus-like gene-transfer vehicle," Proc. Nat. Acad. Sci. USA, Sep. 1992, 89:7934-7938.

Werkmeister et al., "The effect of sequence variations and structure on the cytolytic activity of melittin peptides," Biochimica et Biophysica Acta, 1993, 1157:50-54.

* cited by examiner

FIG. 3

Mix 10mg of PEI coated TCWPs with 20µg of plasmid 2019-nCov-pcDNA3.1(+)-P2A-eGFP in PBS for 30 minutes at 15° to 25°C to form the DNA/PEI complex on the particle surface. Resulting N/P ratio equals 2X.

Add 5×10⁸ flu vaccine virus particles suspended in PBS to mixture and incubate 30 minutes at 15° to 25°C.

Yields 500-1000 viruses per TCWP.

Aliquot 1×10⁷ TCWPs per vaccine (equivalent to 20 µg COVID-19 glycoprotein plasmid DNA and 5×10⁹–1×10¹⁰ flu virus particles; dilute to a final volume of 750 µl) into sterile saline for injection; store at 4°C. (The pharmacist/coordinator draws the vaccine into a 1cc syringe for administration to the patient, using a needle no greater than 23 gauge.)

FIG. 4

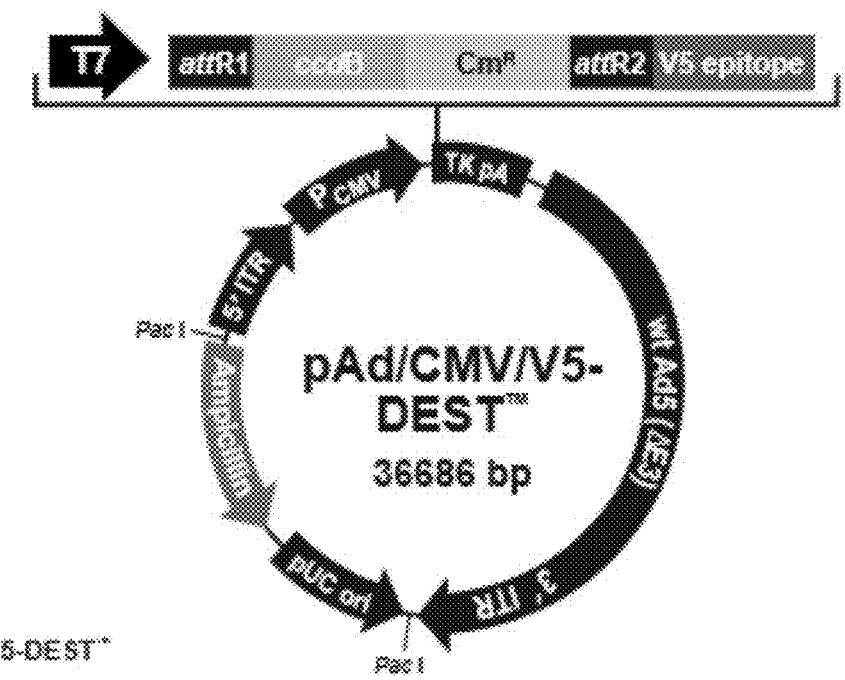

Comments for pAd/CMV/V5-DEST™
36686 nucleotides

Human Ad5 sequences (wt 1-458; includes 5′ L-ITR and packaging signal): 1-458
pAd forward priming site: bases 361-384
CMV promoter: bases 728-1315
T7 promoter/priming site: bases 1359-1378
attR1 site: bases 1407-1531
ccdB gene: bases 1980-2285 (C)
Chloramphenicol resistance gene (Cm$^R$): bases 2607-3266 (C)
attR2 site: bases 3547-3671
V5 epitope: bases 3697-3738
TK polyadenylation signal: bases 3765-4038
Human Ad5 sequences (wt 3513-35935; E3 region deleted; includes 3′ R-ITR): bases 4058-34604
pAd reverse priming site: bases 4059-4082
pUC origin: bases 34781-35442 (C)
Ampicillin (bla) resistance gene: bases 35568-36428 (C)
bla promoter: bases 36429-36527 (C)
Pac I restrictions sites: bases 34610 and 36684
(C) = complementary strand FIG. 6
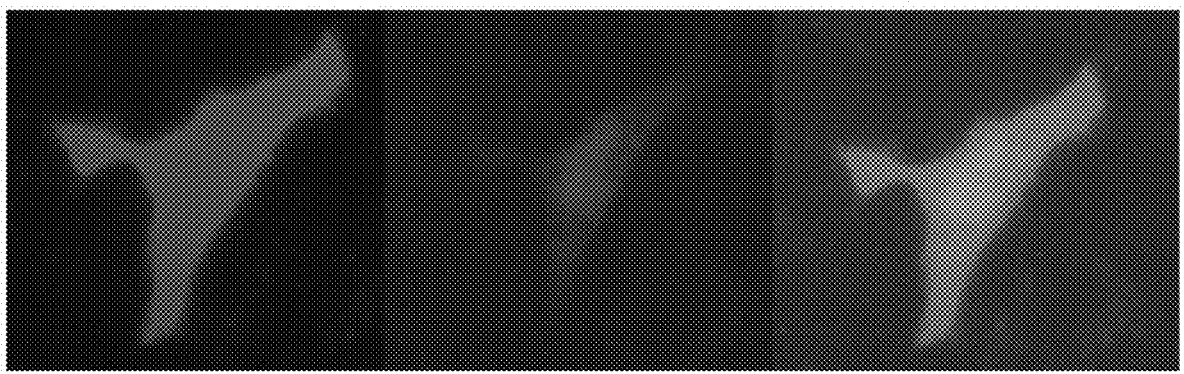
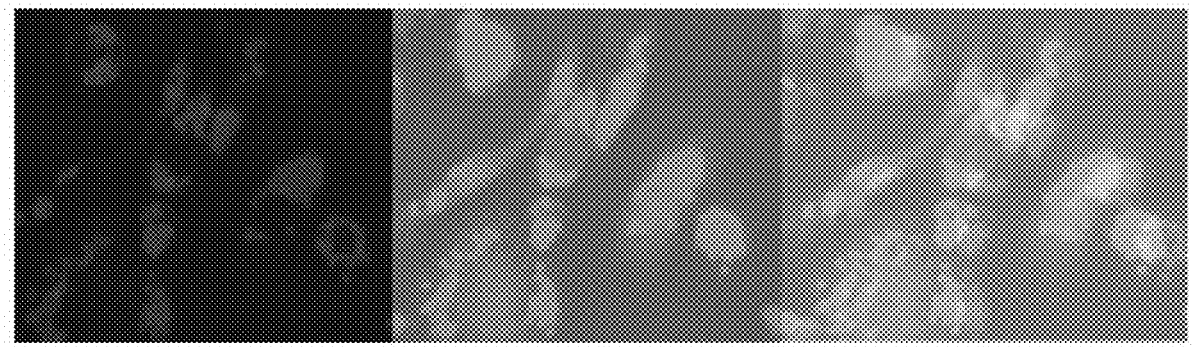

FIG. 9
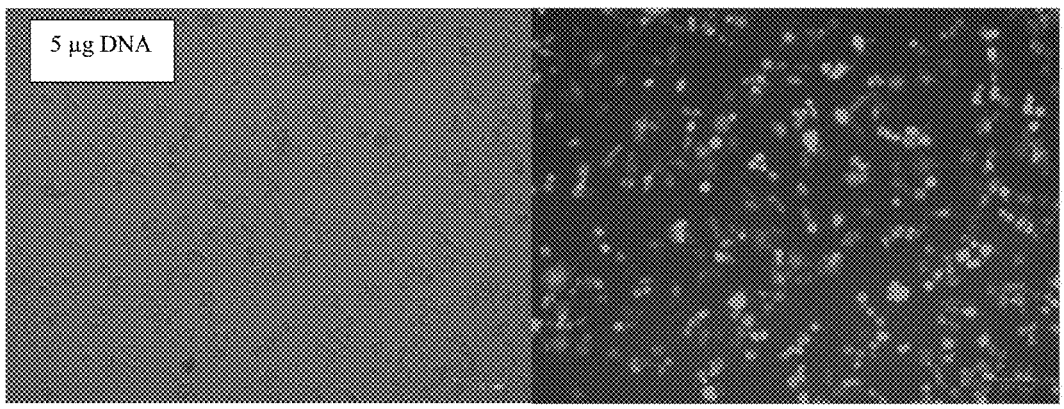
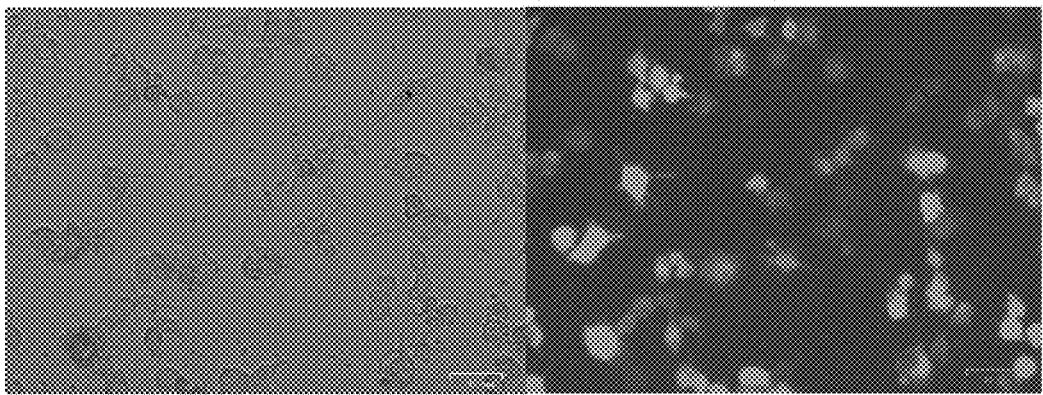

A. GIGAVLKVLTTGLPALISWIKRKRQQ (SEQ ID NO: 3)

LLGDFFRKSKEKIGKEFKRIVQRIKDFLRNLVPRTES (SEQ ID NO: 4)

VIRAL VACCINES FOR IN VIVO EXPRESSION OF A NUCLEIC ACID ENCODING AN IMMUNOGENIC PEPTIDE AND METHODS OF USING THE SAME

SEQUENCE LISTING

The instant application contains a Sequence Listing which has been submitted electronically in ASCII format and is hereby incorporated by reference in its entirety. Said ASCII copy, created on Jun. 29, 2020, is named 096630-0190_SL.txt and is 51,501 bytes in size.

FIELD OF INVENTION

The present disclosure relates generally to the field of infectious disease therapy, and, in particular, nucleic acid vaccines for treating or preventing viral, bacterial, or other microbial infections. The disclosure provides compositions and methods for effectively delivering to cells of the mononuclear phagocyte system (e.g., antigen presenting cells) and other immune cells a nucleic acid encoding an immunogenic peptide. The disclosure further provides methods of treating or preventing a viral, bacterial, or other microbial disease or infection by administering to a patient a vaccine comprising a nucleic acid that encodes an immunogenic peptide, such that the immunogenic peptide is expressed in vivo, thereby activating the patient's immune system to attack the virus or bacteria that expresses the immunogenic peptide.

BACKGROUND OF THE INVENTION

The following discussion is merely provided to aid the reader in understanding the disclosure and is not admitted to describe or constitute prior art thereto.

Infectious diseases caused by viruses, bacteria, and other microbes are a global public health threat. Globalization and increased international travel and commerce have created an environment that allows global disease to spread quickly throughout the world.

Coronavirus disease 2019 (COVID-19; also referred to as novel coronavirus pneumonia or 2019-nCoV acute respiratory disease) is exemplary of the kind of public health threat that can rapidly emerge without warning. COVID-19 is an infectious disease caused by the virus severe respiratory syndrome coronavirus 2 (SARS-CoV-2) (also referred to as novel coronavirus 2019, or 2019-nCoV). The disease was first identified in December 2019 and spread globally, causing a pandemic. Symptoms of COVID-19 include fever, cough, shortness of breath, fatigue, headache, loss of smell, nasal congestion, sore throat, coughing up sputum, pain in muscles or joints, chills, nausea, vomiting, and diarrhea. In severe cases, symptoms can include difficulty waking, confusion, blueish face or lips, coughing up blood, decreased white blood cell count, and kidney failure. Complications can include pneumonia, viral sepsis, acute respiratory distress syndrome, and kidney failure.

COVID-19 is especially threatening to public health because the virus is highly contagious, and studies currently indicate that it can be spread by asymptomatic carriers or by those who are pre-symptomatic. Likewise, the early stage of the disease is slow-progressing enough that carriers may not realize they are infected, leading them to expose numerous others to the virus. The combination of COVID-19's ease of transmission, its high rate of hospitalization, and its death rate make the virus a substantial public health risk, especially for countries without a healthcare system equipped to provide supportive care to pandemic-level numbers of patients. There is not yet a vaccine or specific antiviral treatment for COVID-19 and accordingly, there is a pressing need for treatments or cures.

SARS-CoV-2 is not the only coronavirus that causes disease. It is a β-coronavirus, a genus of coronaviruses that includes other human pathogens, including SARS-CoV (the causative agent of SARS), MERS-CoV (the causative agent of MERS), and HCoV-OC43 (a causative agent of the common cold). The infectivity of these viruses, and the severity of the diseases they cause, varies widely. β-coronavirus can also manifest as zoonotic infections, spread to and from humans and animals. Additionally, non-human species such as camels, bats, tigers, non-human primates, and rabbits can be susceptible to β-coronavirus. Accordingly, there is a pressing need for treatments or cures to multiple coronaviruses.

However, this need is not limited solely to coronaviruses. The next public health threat may emerge from a different type of virus or a bacteria or another type of microbe. Thus, there is a need for a vaccine platform technology that can quickly and adroitly address any infectious disease by training the immune system to recognize a given pathogen.

The immune system is made up of a variety of types of cells that are able to detect the presence of pathogens or pathologic cells in the body and remove them from the body. Sometimes this occurs when a foreign agent is enveloped by immune system cells and destroyed or carried out of the body. If living host cells have been invaded by a bacterial cell or virus, the immune system cells may target and destroy that infected cell or they may target the invading pathogen directly.

For example, monocytic cells are a type of antigen presenting cell that normally patrol the body in search of foreign, non-self-antigens, such as bacteria. Monocytic cells phagocytize bacteria, which are then digested to smaller antigenic portions in the lysosome. The resultant bacterial antigens are cycled back to the cell surface of these cells for presentation to the humoral and cellular arms of the immune system. This antigen presenting function is instrumental in the development of a host immune response to a given foreign, non-self-antigen, as the monocytes load the antigen on MEW class I and II molecules and prime CD8+ and CD4+ T cells, which then mount a specific immune response against the antigen.

Despite this understanding of the antigen presenting process, historically, it has been difficult to develop vaccines that effectively and consistently produce a sustained immunogenic response in a host to a particular antigen. Moreover, scale up and production for widespread use is exceedingly difficult. Most modern vaccines utilize whole virus or bacteria that have been killed or enfeebled prior to administration, or they utilize an isolated peptide or glycopeptide that has shown immunogenicity. Both of these types of vaccines are difficult to produce in mass, requiring large-scale bioreactors, extensive growth and production time, and often delicate and cost-intensive isolation/purification processes.

In contrast to whole pathogens (e.g., virus or bacteria) or peptides/glycopeptides, nucleic acid sequences (e.g., plasmids or expression vectors) are comparatively simple to produce in mass. Nucleic acid sequences can be quickly and reproducibly duplicated far more rapidly than peptides or pathogens, but historically, nucleic acid-based vaccines have achieved little clinical success, mostly due to the difficulty of effectively delivering nucleic acids in vivo. Indeed, with previous nucleic acid vaccines, less than 1% of the cells at an injection site of a nucleic acid vaccine actually take up the vaccine nucleic acid and far less express the encoded protein. For an effective immune response to be achieved, a nucleic acid must be delivered to a specific class of cells—antigen presenting cells (APCs)—and directly injected nucleic acid vaccines rarely reach this target.

Thus, there is a need in the art for a platform for nucleic acid vaccines. The present disclosure fulfills that need by providing multiple vaccine platforms that efficiently and effectively deliver nucleic acids to antigen presenting cells, which can then express an immunogenic peptide(s) encoded by the nucleic acid, thereby inducing a robust immune response to the immunogenic peptide.

SUMMARY OF THE INVENTION

Described herein are nucleic acid vaccines and methods of using the same for treating or preventing infections (i.e., diseases caused by viruses, bacteria, or other microbes).

In one aspect, the disclosure provides a vaccine comprising: (i) a base particle, (ii) a lysosome-evading component attached to the base particle, and (iii) a nucleic acid sequence encoding an immunogenic peptide.

In some embodiments, the base particle is a yeast cell wall particle (YCWP). In some embodiments, the base particle may be a bead (e.g., a ferro-magnetic bead).

In some embodiments, the lysosome-evading component is a non-infectious virus, such as a non-infectious adenovirus. In some embodiments, the non-infectious virus is also non-replicative. In some embodiments, the non-infectious virus is an enfeebled virus. In some embodiments, the lysosome-evading component is a quadrivalent influenza vaccine.

In some embodiments, the lysosome-evading component is a protein (e.g., a lytic protein). In some embodiments, the protein is a hexon protein, a penton protein, melittin, or LL37.

In some embodiments, the nucleic acid encoding the immunogenic peptide is comprised within an expression vector or plasmid.

In some embodiments, the immunogenic peptide is derived from a virus, bacteria, or other microbe. In some embodiments, the virus is a coronavirus, such as SARS-CoV-2.

In some embodiments, the immunogenic peptide is a viral spike protein or an immunogenic fragment thereof. In some embodiments, the immunogenic peptide comprises SEQ ID NO: 1 (i.e., the spike protein of SARS-CoV-2) or an immunogenic fragment thereof.

In some embodiments, the base particle is modified or coated with polyethyleneimine (PEI). For example, in some embodiments, the base particle may be a PEI-modified YCWP. In some embodiments, the base particle may be a PEI-modified bead.

In some embodiments, the lysosome-evading component is attached to the base particle by an antibody. For example, in some embodiments, the lysosome-evading component may be an adenovirus, which is attached to the based particle via an anti-hexon protein antibody.

In some embodiments, the base particle is modified or coated with succinimidyl 3-(2-pyridyldithio)propionate (SPDP). For example, in some embodiments, the base particle may be a SPDP-modified YCWP. In some embodiments, the base particle may be a SPDP-modified bead. In some embodiments, melittin or LL37 may be crosslinked to the base particle (e.g., a YCWP) by the SPDP.

In some embodiments, the vaccine particle is a size that allows it to be preferentially phagocytized by a monocytic cell, such as an antigen presenting cell.

In another aspect, the present disclosure provides a vaccine comprising: (i) yeast cell wall particle (YCWP) that is surface modified with polyethyleneimine (PEI), (ii) an adenovirus attached to the YCWP, and (iii) a nucleic acid sequence encoding a viral spike protein. In some embodiments, the adenovirus is attached to the YCWP indirectly via an anti-hexon protein antibody. In some embodiments, the adenovirus is non-infectious and non-replicative. In some embodiments, the viral spike protein is a SARS-CoV-2 spike protein. In some embodiments, the viral spike protein comprises SEQ ID NO: 1.

In another aspect, the present disclosure provides a vaccine comprising: (i) a non-infectious and non-replicative virus comprising polylysine cross-linked to one or more surface-exposed glutamine residues, and (ii) a nucleic acid sequence encoding an immunogenic peptide. In some embodiments, the virus is an adenovirus. In some embodiments, the one or more surface-exposed glutamine residues are located in the knob domain of an adenovirus fiber protein. In some embodiments, the nucleic acid encoding the immunogenic peptide is comprised within an expression vector or plasmid. In some embodiments, the immunogenic peptide is derived from a virus, bacteria, or other microbe. In some embodiments, the virus is a coronavirus, such as SARS-CoV-2. In some embodiments, the immunogenic peptide is a viral spike protein or an immunogenic fragment thereof. In some embodiments, the immunogenic peptide comprises SEQ ID NO: 1 or an immunogenic fragment thereof.

In another aspect, the present disclosure provides methods of treating or preventing an infectious disease in a patient comprising administering to a patient that may be exposed to an infectious disease a vaccine of any one of the foregoing aspects or embodiments.

In another aspect, the present disclosure provides methods of stimulating the immune system in a patient comprising administering to a patient a vaccine of any one of the foregoing aspects or embodiments.

In some embodiments of the disclosed methods, the vaccine is administered intradermally.

In some embodiments of the disclosed methods, the vaccine is phagocytosed by a monocytic cell and the monocytic cell subsequently expresses the immunogenic peptide and presents the immunogenic peptide on its surface.

In some embodiments of the disclosed methods, the infectious disease is caused by a virus or bacteria. In some embodiments, the infectious disease is coronavirus disease 2019 (COVID-19).

In another aspect, the present disclosure provides a vaccine according to any of the foregoing aspects or embodiments for use in preventing an infectious disease in a subject comprising administering the vaccine to the subject.

In another aspect, the present disclosure provides a vaccine according to any of the foregoing aspects or embodiments for use in stimulating the immune system of a subject in need thereof.

In another aspect, the present disclosure provides uses of the vaccine of any of the foregoing aspects or embodiments to prevent an infectious disease in a subject.

In another aspect, the present disclosure provides uses of the vaccine of any of the foregoing aspects or embodiments for stimulating the immune system of a subject in need thereof.

In another aspect, the present disclosure provides methods of preventing coronavirus disease 2019 (COVID-19) in a subject comprising, administering to a subject a vaccine comprising: (i) yeast cell wall particle (YCWP) that is surface modified with polyethyleneimine (PEI), (ii) an adenovirus attached to the YCWP, and (iii) a nucleic acid sequence encoding a viral spike protein from SARS-CoV-2 or an immunogenic fragment thereof. In some embodiments, the adenovirus is attached to the YCWP indirectly via an anti-hexon protein antibody. In some embodiments of the methods of preventing COVID-19, the adenovirus is non-infectious and non-replicative. In some embodiments, the viral spike protein comprises SEQ ID NO: 1. In some embodiments, the vaccine is administered intradermally. In some embodiments, the vaccine is phagocytosed by a monocytic cell and the monocytic cell subsequently expresses the immunogenic peptide and presents the immunogenic peptide on its surface. In some embodiments, the subject produces antibodies that specifically bind to the spike protein from SARS-CoV-2 as a result of administration of the vaccine.

The foregoing general description and following detailed description are exemplary and explanatory and not limiting of the disclosure.

BRIEF DESCRIPTION OF THE DRAWINGS

FIG. 3 shows a process flow diagram of loading YCWPs with COVID-19 glycoprotein S plasmid DNA and flu vaccine virus.

FIG. 4 shows a vector map of the destination vector pAd/CMV/V5-DEST under the control of a CMV promoter.

FIG. 6 shows mouse RAW 264.7 cells treated with plasmid DNA/Ad5 virus/YCWPs. Red and green fluorescence were observed 24 hours after transfection by fluorescence microscopy. Cells fluorescing green show the presence of functioning Ad5 GFP, while red fluorescing cells show the presence and functionality of the plasmid DNA attached to the YCWPs.

FIG. 9 shows fluorescent micrographs of mouse RAW 264.7 cells transfected with the YCWP with adenovirus attached via a biotin/streptavidin-linked anti-hexon antibody. The results show that essential every cell present was effectively transfected.

FIG. 13 shows the amino acid sequence of LL37.

DETAILED DESCRIPTION

Figure 1:
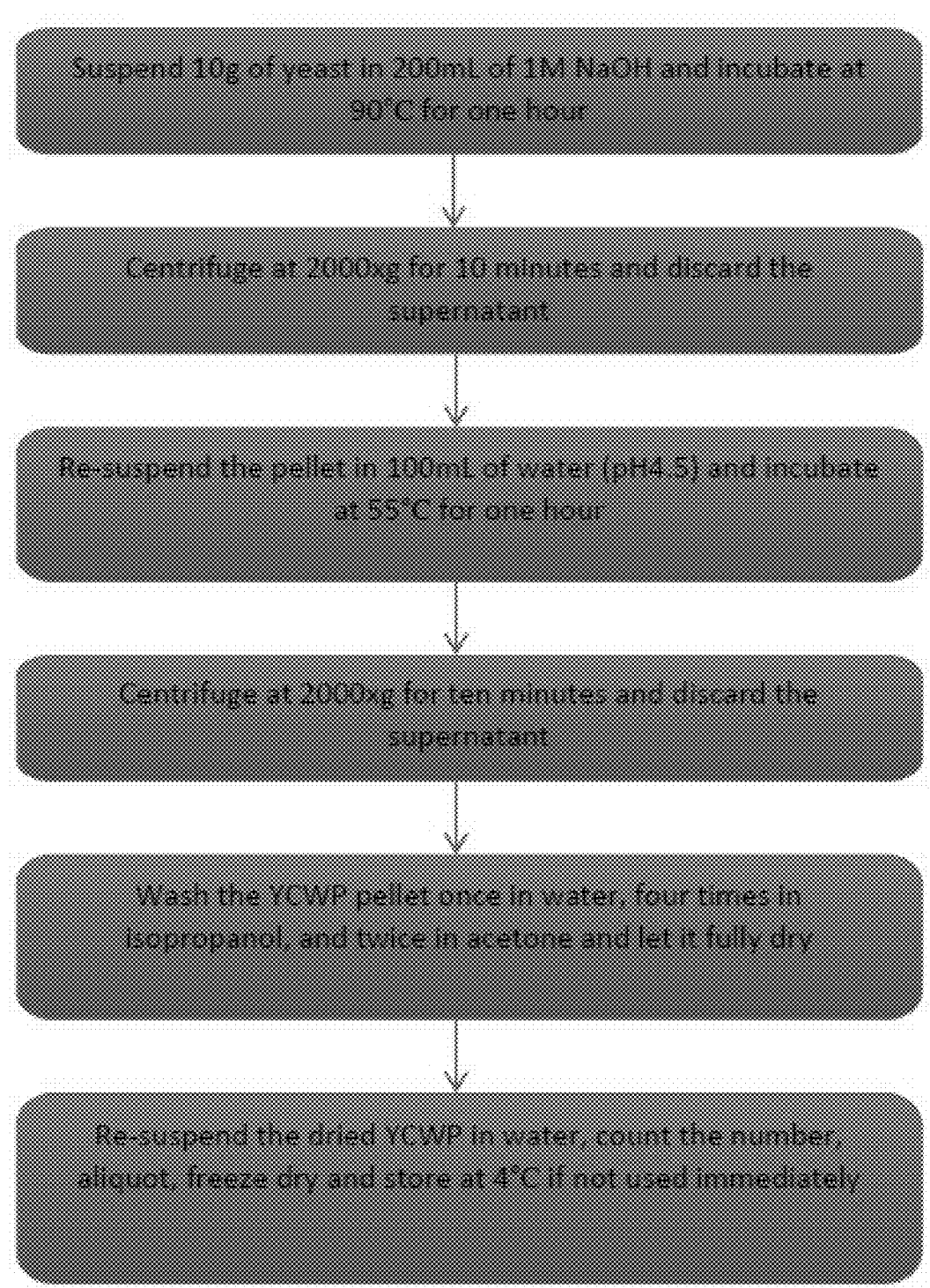
FIG. 1 shows a process flow diagram for the preparation of yeast cell wall particles (YCWPs).

In general, the present disclosure provides novel, nucleic acid vaccines for treating and preventing infections that may be caused by viruses, bacteria, or any number of other infections microbes (e.g., yeast). The disclosed vaccines provide a preventative, vaccine-like function when taken up by an antigen presenting cells (APC) and similar cells of the mononuclear phagocyte system (e.g., monocytes, macrophages, dendritic cells, or immature dendritic cells). In the field of vaccination, cells of the mononuclear phagocyte system are considered "professional" antigen presenting cells and thus, are the ideal target for vaccine delivery. It is well known that presentation of an antigen within an APC is vastly more effective in generating a strong cellular immune response than expression of the same antigen within any other cell type. Accordingly, loading the disclosed vaccine platforms with one or more nucleic acid that encodes an immunogenic peptide will result in the presentation of the immunogenic peptide on an antigen presenting cell via class I MHC and class II MHC molecules, thus eliciting a robust immune response to the immunogenic peptide and to the virus, bacteria, or other microbe from which the immunogenic peptide was derived.

Throughout this disclosure, various publications, patents and published patent specifications are referenced by an identifying citation. The disclosures of these publications, patents and published patent specifications are hereby incorporated by reference into the present disclosure to more fully describe the state of the art to which this disclosure pertains.

Definitions

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term as well as the specified term. For example, "about 10" should be understood as meaning "10" as well as "9 to 11."

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, the phrases "therapeutically effective amount" means that a dose of the disclosed particles provides the specific pharmacological effect for which the drug is administered in a subject in need of such treatment, i.e. to prevent, reduce, ameliorate, or eliminate an infection caused by a virus, bacteria, or other microbe by activating the immune system. It is emphasized that a therapeutically effective amount of a particle will not always be effective in treating or preventing the infection of every individual subject, even though such dosage is deemed to be a therapeutically effective amount by those of skill in the art. Those skilled in the art can adjust what is deemed to be a therapeutically effective amount in accordance with standard practices as needed to treat or prevent a specific subject and/or specific type of infection. The therapeutically effective amount may vary based on the route of administration, site of administration, dosage form, the age and weight of the subject, and/or the subject's condition, and/or type of infection that is being treated or prevented.

The terms "treatment" or "treating" as used herein with reference to an infection caused by a virus, bacteria, or other microbe refer to reducing, ameliorating or eliminating the number of virus, bacteria, or other microbe in the subject being treated (e.g., decreasing viral titer or bacterial load) or otherwise improving the subject's prognosis or quality of life.

The terms "prevent" or "preventing" as used herein refer to stopping an infection caused by a virus, bacteria, or other microbe before the infection develops, progresses, or causes illness in a subject or inhibiting the recurrence of an infection caused by a virus, bacteria, or other microbe.

The terms "individual," "subject," and "patient" are used interchangeably herein, and refer to any individual mammalian subject, e.g., bovine, canine, feline, equine, or human.

The compositions and methods of the disclosure may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Nucleic Acid Vaccine Platforms

The present disclosure provides two novel platforms for nucleic acid vaccines. The first described vaccine platform is particle-based, and the nucleic acid vaccine comprises (i) a base particle (e.g., a yeast cell wall particle or YCWP), (ii) a lysosome-evading component (e.g., a non-infectious virus) attached to the base particle, and (iii) a nucleic acid sequence encoding an immunogenic peptide. The second described vaccine platform is virus-based, and the nucleic acid vaccine comprises a polylysine-modified adenovirus onto which a nucleic acid sequence encoding an immunogenic peptide is attached.

Both nucleic acid vaccine platforms can be used to prepare vaccines against any number of viral, bacterial, or other microbial pathogens by substituting the nucleic acid while leaving the core (i.e., particle or polylysine-modified virus) the same. This is advantageous from both clinical and practical perspectives, as nucleic acids can be rapidly and reliably produced in large quantities, and would allow preparation of a vaccine to begin immediately upon sequencing of the pathogen genome.

As disclosed in further detail herein, both nucleic acid vaccine platforms can be used for treating or preventing infectious diseases caused by viruses (e.g., SARS-CovV-2), bacteria, or other microbes.

For the purposes of the present disclosure, both vaccine platforms share a common component of a nucleic acid that encodes an immunogenic peptide. A nucleic acid sequence encoding an immunogenic may be comprised within an expression vector (e.g., a plasmid), which is capable of expressing the immunogenic peptide in a target cell (e.g., a monocytic cell or antigen presenting cell). More specifically, the expression vector may be used to express one or more immunogenic peptides, which can then be presented on the surface of the target cell via class I MHC and/or class II MHC molecules, thus eliciting an immune response to the immunogenic peptide. An expression vector comprising the nucleic acid encoding an immunogenic peptide may further comprise regulatory sequences, including for example, a promoter, operably linked to the coding sequence, an enhancer, and/or a ribosomal entry site. The expression vector may optionally further comprise a selectable marker sequence, for instance for propagation in in vitro bacterial or cell culture systems. In some embodiments, the selectable marker may be a fluorescent peptide, such as green fluorescent protein (GFP) or red fluorescent protein (RFP).

Figure 5:
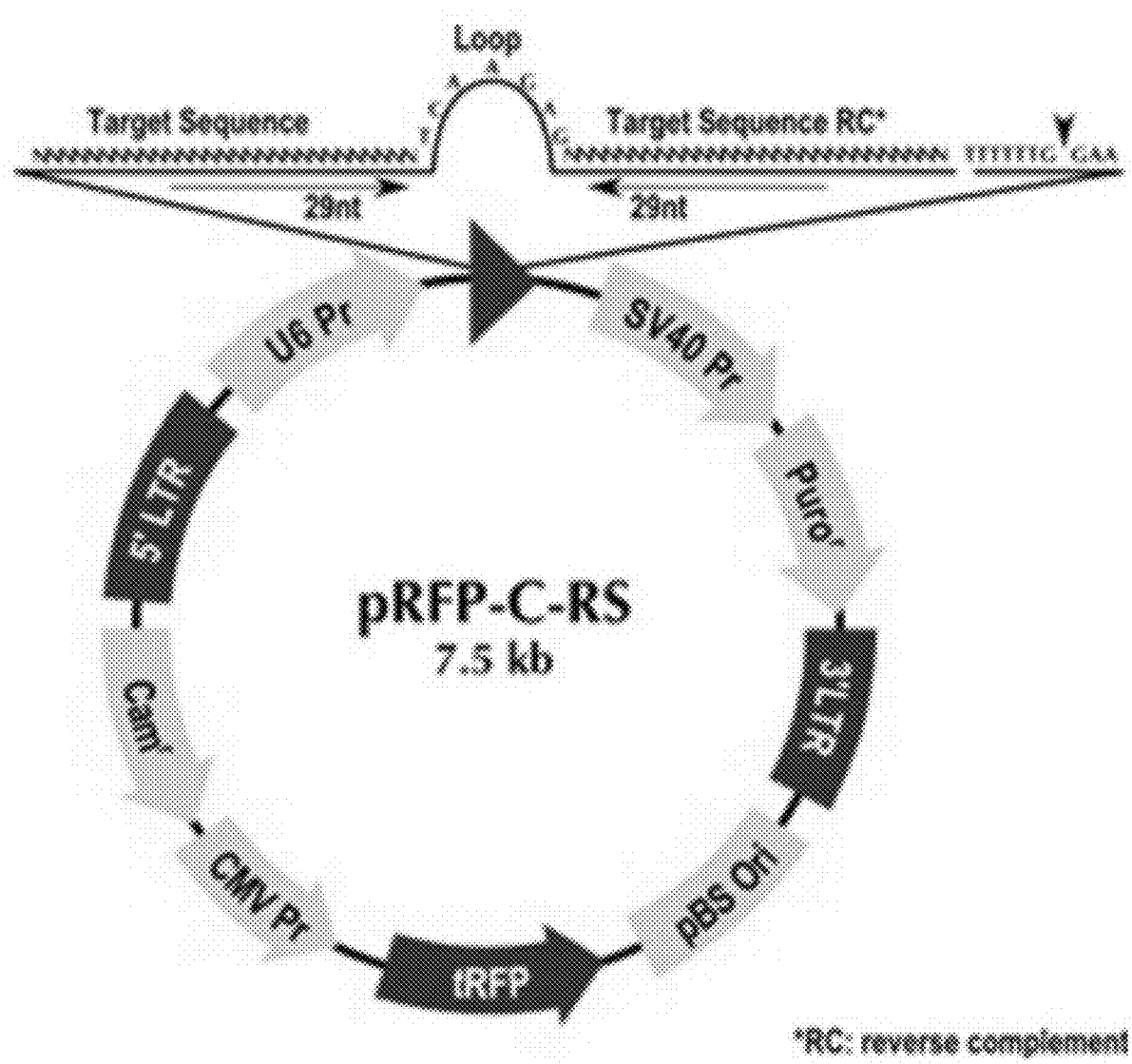
FIG. 5 shows a pRFP-C-RS shRNA plasmid, which was constructed such that the turbo RFP (red fluorescence protein) gene is driven by a CMV promoter. Figure discloses SEQ ID NO: 5.
Figure 7:
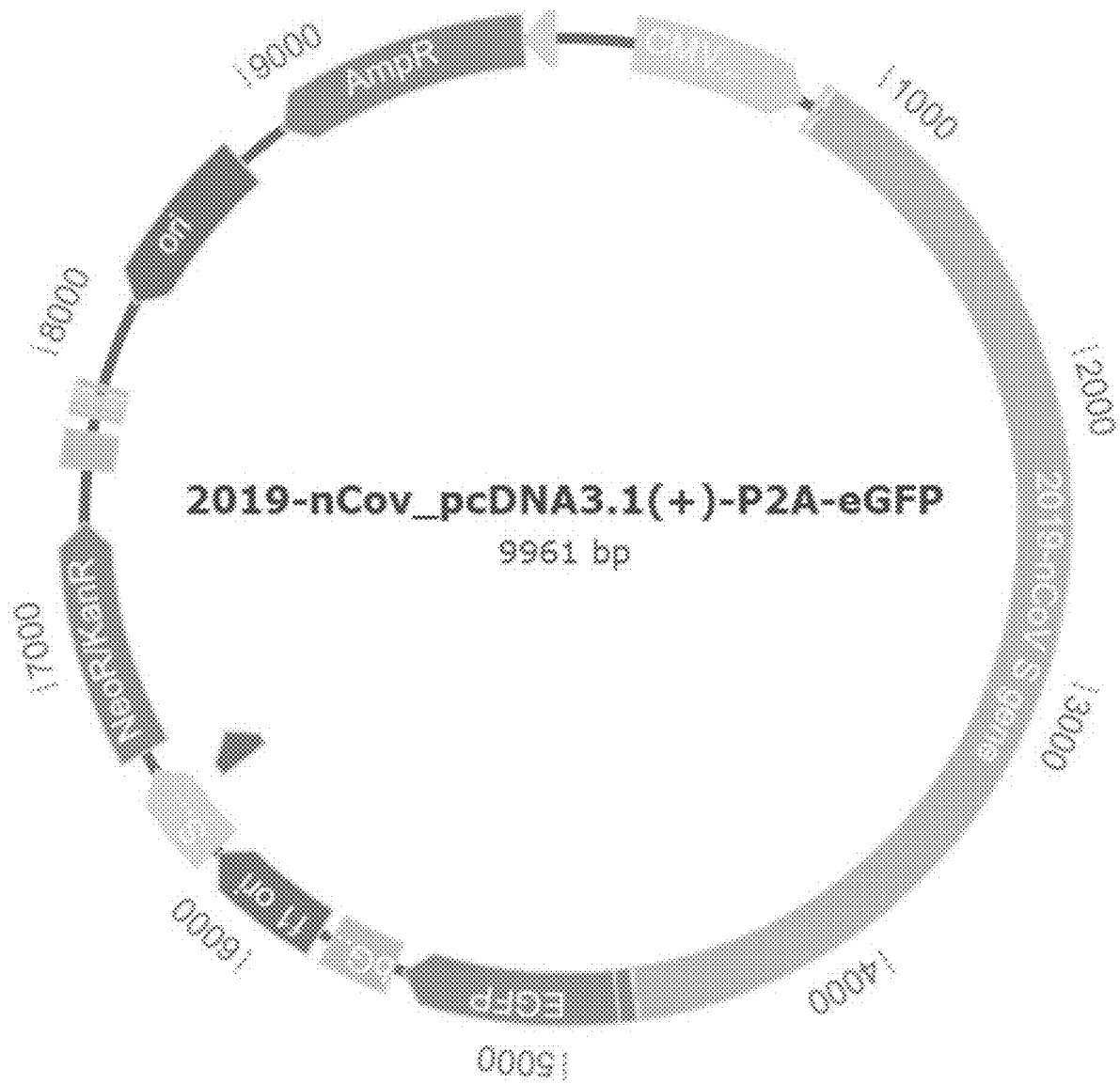
FIG. 7 shows a map of a plasmid encoding a COVID-19 surface glycoprotein S.

Preferred expression vectors may comprise one or more of an origin of replication, a suitable promoter and/or enhancer, and also any necessary ribosome binding sites, polyadenylation sites, splice donor and acceptor sites, transcriptional termination sequences, and 5' flanking non-transcribed sequences. DNA sequences derived from the SV40 or cytomegalovirus (CMV) viral genome, for example, SV40 origin, early promoter, enhancer, splice, and polyadenylation sites may be used to provide the required non-transcribed genetic elements. An exemplary expression vectors are shown in FIGS. 5 and 7. In some embodiments, the promoter may be a T7 promoter. Further exemplary promoters that can be used in the disclosed vaccines include, but are not limited to, EF1a, PGK1 (human or mouse), Ubc, human beta actin, CAG, TRE, UAS, Ac5, Polyhedrin, CaMKIIa, GAL1 and GAL 10 (either independently or together), TEF1, GDS, ADH1, CaMV35S, Ubi, H1, and U6.

Specific initiation signals may also be required for efficient translation and expression of the immunogenic peptide. These signals can include the ATG initiation codon and adjacent sequences. In some embodiments, an expression vector may comprise its own initiation codon and adjacent sequences may be inserted into the appropriate expression vector, and no additional translation control signals may be needed. However, in some embodiments, only a portion of an open reading frame (ORF) may be used, and exogenous translational control signals, including, for example, the ATG initiation codon, can be provided. Furthermore, the initiation codon may be in phase with the reading frame of the desired coding sequence (i.e., the nucleic acid sequence encoding the immunogenic peptide) to ensure translation of the entire target sequence.

Exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516-544 (1987)). Some appropriate expression vectors are described by Sambrook, et al., in *Molecular Cloning: A Laboratory Manual*, Second Edition, Cold Spring Harbor, N.Y. (1989), the disclosure of which is hereby incorporated by reference. If desired, to enhance expression and facilitate proper protein folding, the codon context and codon pairing of the sequence may be optimized, as explained by Hatfield et al., U.S. Pat. No. 5,082,767.

Promoters include, but are not limited to, EF-1a promoter, CMV immediate early, HSV thymidine kinase, early and late SV40, LTRs from retrovirus, and mouse metallothionein-I. Exemplary vectors include pWLneo, pSV2cat, pOG44, pXT1, pSG (Stratagene) pSVK3, pBPV, pMSG, and pSVL (Pharmacia). Selectable markers include CAT (chloramphenicol transferase). Preferred vectors also include cytoplasmic vectors, like the T7 vector system. See Wagner et al., U.S. Pat. No. 5,591,601 (Jan. 7, 1997).

The immunogenic peptide(s) encoded by the nucleic acid of the disclosed vaccine platforms is not particularly limited so long as it elicits an immune response to the pathogenic organism (e.g., virus, bacteria, or other microbe) from which it was derived. For example, the immunogenic peptide may be a full length viral, bacterial, or other microbial protein, or it may comprise only a portion of a viral, bacterial, or other microbial protein. In general, the immunogenic peptide will be a protein or immunogenic fragment thereof that is exposed on the surface of the target virus, bacteria, or microbe, such as a viral coat protein, a bacterial membrane protein, or a bacterial cell wall protein. In some embodiments, the vaccine encodes a full length viral, bacterial, or other microbial surface protein. In some embodiments, the vaccine encodes about 50%, about 55%, about 60%, about 65%, about 70%, about 75%, about 80%, about 85%, about 90%, 91%, 92%, 93%, 94%, 95%, 96%, 97%, 98%, or 99% of a viral, bacterial, or other microbial surface protein, so long as the fragment is able to elicit an immune response (i.e., it is an immunogenic fragment).

When the target pathogen of the vaccine is a virus, the immunogenic peptide may be all or a portion of the spike protein (also known as "S protein" or "glycoprotein S"), which is generally responsible for viral entry into a host cell. The spike protein is ideal to serve as an immunogenic peptide because antibodies that develop against this peptide are likely to be neutralizing. The spike protein comprises two functional subunits responsible for binding to the host cell receptor ($S_1$ subunit) and fusion of the viral and cellular membranes ($S_2$ subunit). A vaccine of the present disclosure may encode the entire spike protein, only the $S_1$ subunit, only the $S_2$ subunit, or any immunogenic portion thereof. In some embodiments, the vaccine encodes a full length spike protein. In some embodiments, the vaccine encodes about 50%, about 55%, about 60%, about 65%, about 70%, about 75%, about 80%, about 85%, about 90%, 91%, 92%, 93%, 94%, 95%, 96%, 97%, 98%, or 99% of a viral spike protein, so long as the fragment is able to elicit an immune response (i.e., it is an immunogenic fragment). Other viral proteins that may serve as the immunogenic peptide when the target pathogen is a virus include, but are not limited to, a viral E protein, M protein, or N protein, or any other viral capsid or coat protein. In some embodiments, the vaccine encodes a full length E protein, M protein, N protein, or other viral capsid or coat protein. In some embodiments, the vaccine encodes about 50%, about 55%, about 60%, about 65%, about 70%, about 75%, about 80%, about 85%, about 90%, 91%, 92%, 93%, 94%, 95%, 96%, 97%, 98%, or 99% of an E protein, M protein, N protein, or other viral capsid or coat protein, so long as the fragment is able to elicit an immune response (i.e., it is an immunogenic fragment). In some embodiments, the immunogenic peptide may be derived from a coronavirus, hepatitis A, hepatitis B, hepatitis C, human immunodeficiency virus (HIV), an influenza virus, or a norovirus.

When the target pathogen of the vaccine is a bacteria, the immunogenic peptide may be all or a portion of an outer membrane protein (OMP), such as OmpA or any other exposed surface protein that is immunogenic. For instance, the immunogenic peptide may be a peptide derived from *Acinetobacter baumannii, Bacteroides fragilis, Burkholderia cepacia, Clostridium difficile, Clostridium sordellii,* Enterobacteriaceae sp., *Enterococcus faecalis, Escherichia coli, Klebsiella pneumonia, Staphylococcus aureus* (including methicillin-resistant strains or MRSA, and vancomycin-resistant or VRSA), *Morganella morganii, Mycobacterium abscessus, Pseudomonas aeruginosa, Stenotrophomonas maltophilia, Mycobacterium tuberculosis,* or *Enterococci* sp.

In some embodiments, monocytic cells may to exposed to, and therefore phagocytose, a nucleic acid vaccine as disclosed herein, which comprise more than one expression vector, and the expression vectors may encode the same or different immunogenic peptides. For example, in some embodiments, a vaccine may comprise expression one expression vector that encodes an S1 subunit of a viral spike protein and a second expression vector that encodes an S2 subunit of a viral spike protein. As a further example, in some embodiments, a vaccine may comprise expression one expression vector that encodes a viral spike protein and a second expression vector that encodes a viral E protein, M protein, or N protein. Additionally or alternatively, in some embodiments a given monocytic cell may be exposed to, and therefore phagocytose, more than one of the disclosed nucleic acid vaccines, each of which comprises a different expression vector encoding a different immunogenic peptide. For example, a monocytic cell may phagocytose two different vaccines, one of which comprises an expression vector that encodes a viral spike protein and another of which comprises an expression vector that encodes a viral E protein, M protein, or N protein. Accordingly, in some embodiments, the present disclosure provides monocytic cells (such as antigen presenting cells) that express 1, 2, 3, 4, or 5 or more different immunogenic peptides, as disclosed herein.

Particle-Based Nucleic Acid Vaccine Platform

The present disclosure provides a particle-based nucleic acid vaccine platform for directed entry of a nucleic acid encoding an immunogenic peptide into a monocyte cell (e.g., an antigen presenting cell). A particle-based vaccine according to the present disclosure is generally composed of (i) a base particle (e.g., a yeast cell wall particle or YCWP) that can be phagocytosed by a monocytic cell, (ii) a lysosome-evading component (e.g., a non-infectious virus) attached to the base particle, and (iii) a nucleic acid sequence encoding an immunogenic peptide, which may also be attached to the based particle. The disclosed particle-based vaccines are highly specific for phagocytic cells like monocyte cells, including dendritic cells and macrophages. This pronounced selectivity for monocyte cells renders the particle-based vaccines extremely useful for presenting antigens to elicit an immune response.

The disclosed particle-based platform has demonstrated an ability to deliver its antigenic "payload" directly and specifically into APCs with remarkable efficiencies of greater than 90%. Moreover, because the disclosed platform takes advantage of the avid phagocytosis of particles, such as yeast cell wall particles (YCWPs), of a specific size range with pathogen associated molecular profiles like yeast beta glucan by monocyte cells, the pathway of entry into APCs is through the APC's phagosome. As a result of this mode of entry any molecular "payload" of the YCWPs is exposed to the highly lytic environment within the phagosome's early decedent, the phagolysosome. While exposure of protein antigens to this environment can result in nucleic acid digestion, a DNA vaccine in which a single cleavage site within a coding sequence would render that sequence useless must have a mechanism of escaping the phagosome. This phagolysosome lytic degradation of vaccine DNA sequences established a significant challenge for developing a nucleic acid vaccine. However, recognition of the ability of adenoviruses to escape phagolysosome degradation of viral DNA upon entry into virally infected cells provided a means of overcoming this challenge. As will be described in more detail below, the attachment of a lysosome-evading component (e.g., an enfeebled adenovirus particle) to a base particle, such as a YCWP, allows passage of that "decorated" particle, which can also carry a nucleic acid encoding an immunogenic peptide, through the phagosome or phagolysosome without damage to the nucleic acid.

A. Base Particle

The disclosed particle-based nucleic acid vaccines take advantage of the phagocytic activity of monocyte cells by "looking" like a bacterium. Thus, a preferred size for the base particle is one that approximates the size of the bacterial antigens that monocyte cells typically ingest. Generally, the vector particle will be about 0.5 to about 2.5 microns, or about 0.5 to about 1 micron. Thus, the vector particle may be about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, or about 2.5 microns.

In preferred embodiments, the base particle may be a yeast cell wall particle (YCWP), such as yeast glucan particles. In some embodiments, the base particle may be a bead.

i. Yeast Cell Wall Particle (YCWP)

A YCWP can be prepared from yeast cell wall such that the particle is porous to the delivery of various macromolecules. In one embodiment, the YCWP can be prepared from *Saccharomyces cerevisiae*. In another embodiment, the YCWP can a zymosan particle. In another embodiment, the YCWP approximates the size of microbial structures that cells of the mononuclear phagocyte system and other phagocytic cells typically ingests (e.g., bacteria). In specific embodiments, the YCWP can be about 1-5 μm.

In some embodiments, the YCWP may be prepared by (a) suspending yeast to produce a suspension, (b) incubating the suspension, (c) centrifuging the suspension and removing the supernatant and (d) recovering the resulting YCWP. In some embodiments, steps (a)-(d) are repeated at least 1, 2, 3 or 4 times.

In some embodiments, the YCWP may be prepared by (a) suspending yeast in a solution to produce a first suspension, (b) incubating the first suspension, (c) centrifuging the first suspension and removing the supernatant, (d) suspending the resulting pellet to produce a second suspension, (e) incubating the second suspension, (f) centrifuging the second suspension and removing the supernatant and (g) washing the resulting pellet to recover the YCWP. In some embodiments, the YCWP is sterilized.

In some embodiments, the yeast is suspended in NaOH, including 1M NaOH. In some embodiments, the first suspension is incubated at about 80° C. for about 1 hour or for 1 hour. In some embodiments, the centrifuging is performed at about 2000 times gravity for about 10 minutes, or at 2000 times gravity for 10 minutes. In some embodiments, the pellet is suspended in water, including water at about pH 4.5 or at pH 4.5. In some embodiments, the second suspension is incubated at about 55° C. for about 1 hour or at 55° C. for 1 hour. In some embodiments, the pellet is washed in water at least 1, 2, 3 or 4 times. In some embodiments, the pellet is washed once.

In some embodiments, the YCWP is sterilized using isopropanol and/or acetone following washing of the pellet. In specific embodiments, other known alcohols are appropriate. In some embodiments, the YCWP is allowed to fully dry after sterilization. In some embodiments, the YCWP is resuspended after being allowed to dry. In some embodiments, the YCWP is freeze dried and store at 4° C.

A general flow diagram for preparing YCWPs is provided in FIG. 1.

Figure 2:
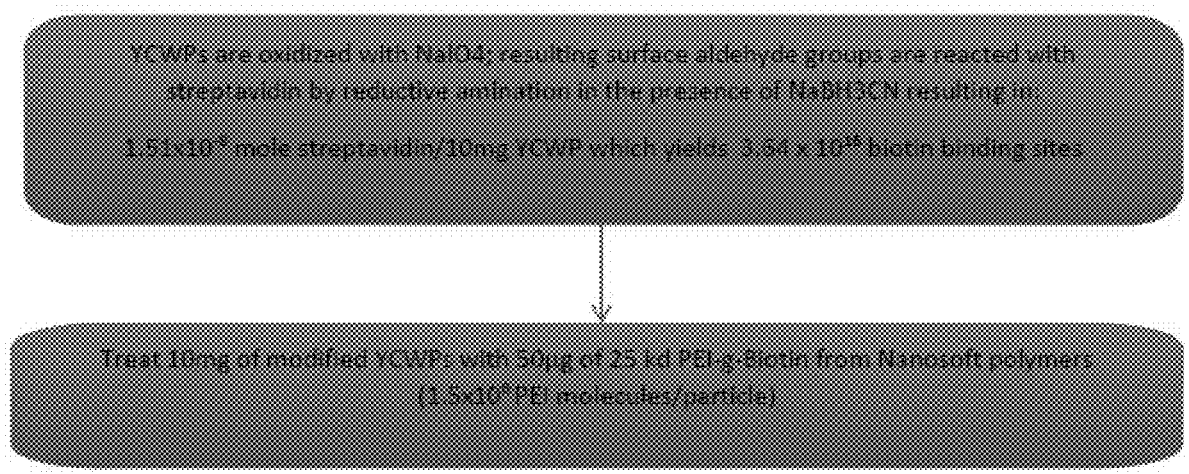
FIG. 2 shows a process flow diagram of treating YCWPs with PEI to create a positively charged external surface.

In order to functionalize a YCWP for attachment of a lysosome-evading component (e.g., an adenovirus) and a nucleic acid encoding an immunogenic peptide, the YCWP can be surface modified with polyethyleneimine (PEI). PEI provides a highly positively charged external surface, onto which a negatively charged nucleic acid (e.g., a nucleic acid encoding an immunogenic peptide) may bind. A general flow diagram showing how a YCWP can be surface modified with PEI is provided in FIG. 2. Briefly, YCWPs may first be surface modified with streptavidin and oxidized with sodium periodate, which allows the surface aldehyde groups of the YCWP to react with streptavidin by reductive amination in the presence of sodium cyanoborohydride. The resulting modified YCWPs thus possess streptavidin on their surfaces. PEI-g-PEG-Biotin can then be used to coat the streptavidin-modified YCWPs with PEI. Contacting these PEI-modified YCWPs with a nucleic acid (e.g., DNA) results in the formation of a nucleic acid/PEI complex on the surface of the particles.

Thus, in some embodiments, the particle-based nucleic acid vaccine may comprise a YCWP surface modified with polyethyleneimine (PEI), which is then bound with Adenovirus 5 Flu vaccine viruses and 2019-nCov_pcDNA3.1(+)-p2A-eGFP DNA plasmids encoding the surface glycoprotein (S protein) of COVID-19 (C19FP).

ii. Bead Particle

In those embodiments when a bead is used as the base particle, several factors must be weighed to determine the ideal bead for a given need. For instance, from the perspective of uptake, the smaller end of the ranges is preferred, because it more closely approximate the size of a bacterium. On the other hand, for manufacturing purposes, slightly larger particles may be preferred, because they may be less likely to stick together.

Furthermore, the bead particle is not limited by shape or material. The bead particle can be of any shape, size, or material that allows the bead vector to be phagocytized by monocytic cells.

In some embodiments, the base particle be selected from any known ferro-magnetic center covered by a polymer coat, such as PEI. For example, beads that can be used as a base particle include, but are not limited to, microbeads, microspheres, and silicate beads. Such beads may be preferred in certain applications because magnetic separation can be employed to separate free from bead-bound components during processing. However, bead particles for use in the disclosed delivery vectors are not limited to a specific type of material and may be made of synthetic materials like polystyrene or other plastics, as well as biological materials.

B. Lysosome-Evading Component In addition to the base particle, a delivery vector of the present disclosure may also comprise a lysosome-evading component, for example, an adenovirus or retrovirus attached or conjugated to the base particle. The role of the lysosome-evading component with respect to the vaccine is to assist the vector in escaping the harsh environment of the lysosome following phagocytosis by a monocyte cell and to deliver the nucleic acid or expression vector that encodes an immunogenic peptide for expression and presentation on the surface of the target monocytic cell.

When a monocytic cell ingests a large antigen, a phagocytic vesicle (phagasome) is formed which engulfs the antigen. Next, a specialized lysosome contained in the monocyte cell fuses with the newly formed phagosome. Upon fusion, the phagocytized antigen is exposed to several highly reactive molecules as well as a concentrated mixture of lysosomal hydrolases. These highly reactive molecules and lysosomal hydrolases digest the contents of the phagosome. By attaching a lysosome-evading component to the particle, the nucleic acid that is attached to the base particle can escape digestion by the materials in the lysosome and enters the cytoplasm of the monocyte intact. Prior systems have failed to recognize the importance of this feature and, thus, obtained much lower levels of expression than the expression systems of the present disclosure. See Falo et al., WO 97/11605 (1997).

Thus, in some embodiments a particle-based vaccine of the present disclosure may comprise one or more lysosome-evading components attached to the surface of a base particle (e.g., a YCWP or bead particle). The lysosome-evading component may be an RNA virus, like a retrovirus, or a DNA virus, like an adenovirus. In some embodiments, the virus may be recombinant and/or non-replicative and/or non-infective, such as an enfeebled virus like an influenza vaccine (e.g., a SEQIRUS® quadrivalent flu vaccine). One of skill in the art will know of commonly used methods to make a virus non-replicative and/or non-infective. Preferred viruses include, but are not limited to, adenovirus (e.g., adenovirus 5 or Ad5), lentivirus (e.g., HIV-derived viruses), and adeno associate virus ("AAV"; e.g., AAV5, AAV9, etc.).

Because viral infection is not essential for expression of the nucleic acid or expression vector encoding an immunogenic peptide within the monocyte cell, the virus can also be replication/infection deficient. For example, one method for producing a replication/infection deficient adenovirus can be achieved by altering the virus fiber protein. Thus, in some embodiments, a virus in which the fiber protein is engineered by specific mutations to allow the fiber protein to bind to an antibody but not to its cognate cellular receptor can be used in the particles of the present disclosure. Another method for producing a replication/infection deficient virus is by intentionally causing denaturation of the viral component responsible for infectivity. In the case of adenovirus, for example, the fiber protein could be disrupted during the preparation of the virus. For HIV, this could include the envelope (env) protein. Thus, in some embodiments, a method for creating an infection deficient virus for attachment to the disclosed bead particles comprises removing the outer membranes of the virus so that only the virus core remains.

In some embodiments, transient expression may be preferred and cytoplasmic viruses, like Sindbis virus, for example, can therefore be employed.

In some embodiments, where no lysosome-evading component is naturally present on the virus, one may be added. For example, in the case of Sindbis or other such viruses, the virus can be engineered to express all or part of the adenovirus penton protein for the purpose of evading the lysosome.

In some embodiments, the lysosome-evading component can include proteins, carbohydrates, lipids, fatty acids, biomimetic polymers, microorganisms and combinations thereof. It is noted that the term "protein" encompasses a polymeric molecule comprising any number of amino acids. Therefore, a person of ordinary skill in the art would know that "protein" encompasses a peptide, which is understood generally to be a "short" protein. In some embodiments, lysosome-evading components include, but are not limited to, specific viral proteins, for example, an adenovirus hexon protein or penton protein. Adenovirus hexon proteins are a type of major coat protein in adenoviruses, and the adenovirus penton protein is a complex formed by the peripentonal hexons and penton base, which enables a virus to evade/disrupt the lysosome/phagosome. Thus, either the intact adenovirus or the isolated hexon or penton protein, or a portion thereof (see, e.g., Bal et al., Eur J Biochem 267:6074-81 (2000)), can be utilized as the lysosome-evading component. In some embodiments, fusogenic peptides derived from N-terminal sequences of the influenza virus hemagglutinin subunit HA-2 may also be used as the lysosome-evading component (Wagner, et al., *Proc. Natl. Acad. Sci. USA,* 89:7934-7938, 1992).

For example, in some embodiments, proteins that can serve as a lysosome-evading component include, but are not limited to, melitin and LL37. Melittin is the principal active component of apitoxin (bee venom) and is a powerful stimulator of phospholipase A2. Melittin is a peptide consisting of 26 amino acids, the sequence and structure of which are shown in FIG. 12. Melittin has multiple known biological functions, including the inhibition of protein kinase C, Ca'/calmodulin-dependent protein kinase II, myosin light chain kinase and Na+/K+-ATPase, but it is also a membrane lytic factor, capable of disrupting or destroying phospholipid membranes. LL37 is a 37 amino acid cationic peptide generated by extracellular cleavage of the C-terminal end of the 18 kDa hCAP18 protein by serine proteases of the kallikrein family in keratinocytes and proteinase 3 in neutrophil. The sequence of LL37 is shown in FIG. 13.

Melittin and/or LL37 can be loaded onto a base particle, such as a YCWP, by known methods, including but not limited to incubating the YCWPs in solution with melittin and/or LL37 and then freeze-drying the composition. In some embodiments, a lysosomal-evading protein (e.g., melittin or LL37) may be attached to the base particle (e.g., YCWP) via any of the following bonds, which are preferred for their ability to be cleaved or are otherwise labile in the phagosome: disulfide, poly-imine (particularly a poly-imine-coated particle and a lytic peptide comprising an aldehyde or polyaldehyde), β-thiopropionate, cis-aconityl, hydrosome, diorthoester, orthoester, vinylether, or phosphoramidate. The foregoing chemical bond are desirable because while the lysosomal-evading protein (e.g., melittin or LL37) is bound to the base particle (e.g., YCWP), it is inactive, but upon cleavage of the chemical bond within the phagosome the lysosomal-evading protein is released and can form pores in the phagosome to allow the particle and nucleic acid to escape. In some embodiments, the lysosomal-evading protein (e.g., melittin or LL37) may be indirectly connected to the base particle (e.g., YCWP) indirectly via a sulfosuccinimidyl 6-[3'(2-pyridyldithio)-propionamido (SPDP) alone or in combination with PEI. SPDP are a unique group of amine- and sulfhydryl-reactive heterobifunctional crosslinkers that can be used to form amine-to-amine or amine-to-sulfhydryl crosslinks among molecules, and the SPDP reagents produce disulfide-containing linkages that can be cleaved later by, for example, reducing agents. Accordingly, SPDP can react with the sulfhydrl group of a cysteine, such as the N-terminal cysteine in the commercially available Cys-LC-LL37 (available from AnaSpec, Inc.; catalog number AS-63692) or the terminal amine group of melittin.

The disclosed delivery particles may comprise about $5.0 \times 10^5$ to about $3.0 \times 10^6$ molecules of melittin and/or LL37 per particle. Thus, the disclosed delivery particles may comprise about $5.0 \times 10^5$, about $5.5 \times 10^5$, about $6.0 \times 10^5$, about $6.5 \times 10^5$, about $7.0 \times 10^5$, about $7.5 \times 10^5$, about $8.0 \times 10^5$, about $8.5 \times 10^5$, about $9.0 \times 10^5$, $9.1 \times 10^5$, about $9.2 \times 10^5$, about $9.3 \times 10^5$, about $9.4 \times 10^5$, about $9.5 \times 10^5$, about $9.6 \times 10^5$, $9.7 \times 10^5$, about $9.8 \times 10^5$, about $9.9 \times 10^5$, about $1.0 \times 10^6$, about $1.1 \times 10^6$, about $1.2 \times 10^6$, about $1.3 \times 10^6$, about $1.4 \times 10^6$, about $1.5 \times 10^6$, about $1.6 \times 10^6$, about $1.7 \times 10^6$, about $1.8 \times 10^6$, about $1.9 \times 10^6$, about $2.0 \times 10^6$, about $2.1 \times 10^6$, about $2.2 \times 10^6$, about $2.3 \times 10^6$, about $2.4 \times 10^6$, about $2.5 \times 10^6$, or about $3.0 \times 10^6$ molecules of melittin and/or LL37 per particle. The amount of melittin and/or LL37 per particle may be at least any of these amounts or more.

Lysosome evading compounds similar to melittin, which are also within the scope of the disclosure, include bombolitin from bumblebee venom (17 amino acid amphiphilic alpha-helix), mastoparan from wasp venom (14 amino acid amphiphilic alpha-helix) and crabrolin from hornet venom (13 amino acid amphiphilic alpha-helix) Argiolas A. and Pisano J. J., 1985, J. Biol. Chem. 260, 1437-1444). Additionally, the lysosome evading component my comprise a cytolytic derivative or analog of melittin, so long as the derivative or analog is able to lyse the lysosome to safely deliver the nucleic acid of interest into the cytoplasm of the target cell. For example, Werkmeister et al. (1993), Biochim. Biophys. Acta 1157: 50-54, discloses the effect of sequence and structural variations on the cytolytic activity of melittin, and is hereby incorporated by reference in its entirety. Thus, other lysosome evading components include melittin analogs and derivatives that contain at least one γ-linked glutamate residue linked via a peptide bond to the epsilon amino group of a lysine (hereinafter "γ-glutamate-masked melittin analog").

Other lysosome evading components include, but are not limited to, biomimetic polymers such as Poly (2-propyl acrylic acid) (PPAAc), which has been shown to enhance cell transfection efficiency due to enhancement of the endosomal release of a conjugate containing a plasmid of interest (see Lackey et al., *Abstracts of Scientific Presentations: The Third Annual Meeting of the American Society of Gene Therapy*, Abstract No. 33, May 31, 2000-Jun. 4, 2000, Denver, Colo.) Examples of other lysosome evading components envisioned by the present invention are discussed by Stayton, et al. *J. Control Release,* 1; 65(1-2):203-20, 2000.

A single base particle may have numerous lysosome-evading components (e.g., viruses, such as an adenovirus, or proteins, such as a penton protein, melittin, or LL37) attached or conjugated to its surface.

Viruses or proteins that are utilized as the lysosome-evading component can be attached to the base particles directly, using conventional methods, or indirectly. See Hammond et al., Virology 254:37-49 (1999). For example, YCWPs can be oxidized with sodium periodate to generate aldehydes, which can be further reacted with adipic acid dihydrazide to form ADH-particles. These ADH-particles can be derivatized with SPDP (succinimidyl 3-(2-pyridyldithio)propionate) crosslinker and reacted with SPDS derivatized streptavidin to form YCWP conjugated with streptavidin, i.e., streptavidin-modified YCWPs. Streptavidin-modified YCWPs can be directly used for conjugation of biotinylated viral particles (e.g., biotinylated adenovirus), biotinylated antibodies (e.g., an anti-hexon protein antibody, such as the adenovirus 5 hexon-specific antibody from Invitrogen: PA1-28357), or they can be further modified with Biotin-polyethyleneimine (PEI). Avidin-modified YCWPs can be saturated with PEI-g-PEG-Biotin to form PEI modified particles, PEI-particles. Adenovirus (and other anionic viruses) can be carried by PEI-particles through charge interactions between the PEI and the anionic charge of the virus coat. Alternatively, if a biotinylated antibody (e.g., an anti-hexon protein antibody) is attached to the streptavidin-modified YCWPs, subsequently contacting/incubating the particles with particles with a virus or protein to which the antibodies can bind will indirectly attach the virus or protein to the particle. Accordingly, in some embodiments, the lysosome-evading component may be a virus, such as an adenovirus 5, that is bound to the base particle (e.g., YCWP) via a biotinylated antibody that binds to adenovirus 5 hexon protein. In some embodiments, the lysosome-evading component may be a hexon protein, melittin, LL37, or the like that is bound to the base particle (e.g., YCWP) via a biotinylated antibody that binds to any one of the recited lysosome-evading proteins.

Thus, in some embodiments, the nucleic acid may escape lysosomal digestion as a result of the particle comprising a lysosome-evading component that is conjugated to the base particle via a biotin-streptavidin linkage. The base particle may be modified to attach a linker comprising streptavidin and the lysosome-evading component may be biotinylated (e.g., a biotinylated virus) or indirectly bound to the particle by an intermediate connection that is biotinylated (e.g., a biotinylated anti-hexon protein antibody).

Indeed, antibody attachment is an efficient way to attach a desired virus to the base particle. One example of antibody attachment encompassed may comprise a single antibody that is chemically affixed to the bead vector particle. The antibody is specific to the component to be attached to the base particle (e.g., a virus or lysosome-evading protein).

In some embodiments, two or more antibodies can be used. In this case, one antibody, which is attached to the base particle, may be specific for a second antibody. The second antibody may be specific to the virus to be attached to the base particle. Thus, the virus-specific antibody binds the virus, and that antibody, in turn, is bound by the antibody attached to the base particle. For instance, a goat- or rabbit-anti-mouse antibody may be bound to the bead and a mouse monoclonal antibody can be used to bind the specific virus. Or, in another alternative format, the two or more antibodies my each be specific for a different viruses or proteins to be attached to the particle, such that the particle is decorated with two or more distinct lysosome-evading components.

In another example of antibody attachment, protein A, or any similar molecule with an affinity for antibodies, may be employed. In this example, the base particle may be coated with protein A, which binds to an antibody, and, in turn is bound to the virus being attached to the base particle.

In some embodiments, attaching viruses to a base particle can also be accomplished by engineering the virus to express certain proteins on its surface. For instance, the HIV env protein might be replaced with the adenovirus penton protein, or a portion thereof. The recombinant virus then could be attached via an anti-penton antibody, with attachment to the base particle mediated, for example, by another antibody or protein A. In some embodiments, a penton protein may also serve as a lysosome evading component.

Virus-Based Nucleic Acid Vaccine Platform

The present disclosure provides a virus-based nucleic acid vaccine platform for directed entry of a nucleic acid encoding an immunogenic peptide into a monocyte cell (e.g., an antigen presenting cell). A virus-based vaccine according to the present disclosure is generally composed of an enfeebled or non-infective virus, such as an adenovirus, that has been surface modified with polylysine such that a nucleic acid encoding an immunogenic protein can bind to the positively charged polylysine via electrostatic interaction with the negatively charge nucleic acid.

Without being bound by theory, it is believed that, as a result of the addition of bundles of nucleic acid to the surface of the poly-lysine modified virus, the disclosed virus-based vaccines may be of a size that encourages phagocytosis by monocytic cells much in the same way that the particle-based vaccines described above.

For the purposes of the virus-based vaccine platform, adenovirus (e.g., adenovirus 4 or adenovirus 5) are a preferred base or core onto which the nucleic acid encoding an immunogenic peptide can be added. Adenoviruses (Ads) are nonenveloped virions 70-90 nm in diameter with a capsid consisting of three main exposed structural proteins, the hexon, fiber, and penton base. Hexon accounts for the majority of the structural components of the capsid, which consists of 240 trimeric hexon capsomeres and 12 pentameric penton bases. The trimeric fiber protein protrudes from the penton base at each of the 12 vertices of the capsid and is a knobbed rod-like structure. A distinct difference in the surface of adenovirus capsids compared to that of most other icosahedral viruses is the presence of the long, thin fiber protein, the primary role of which is to tether the viral capsid to a target cell surface via its interaction with a cellular receptor.

Figure 10:
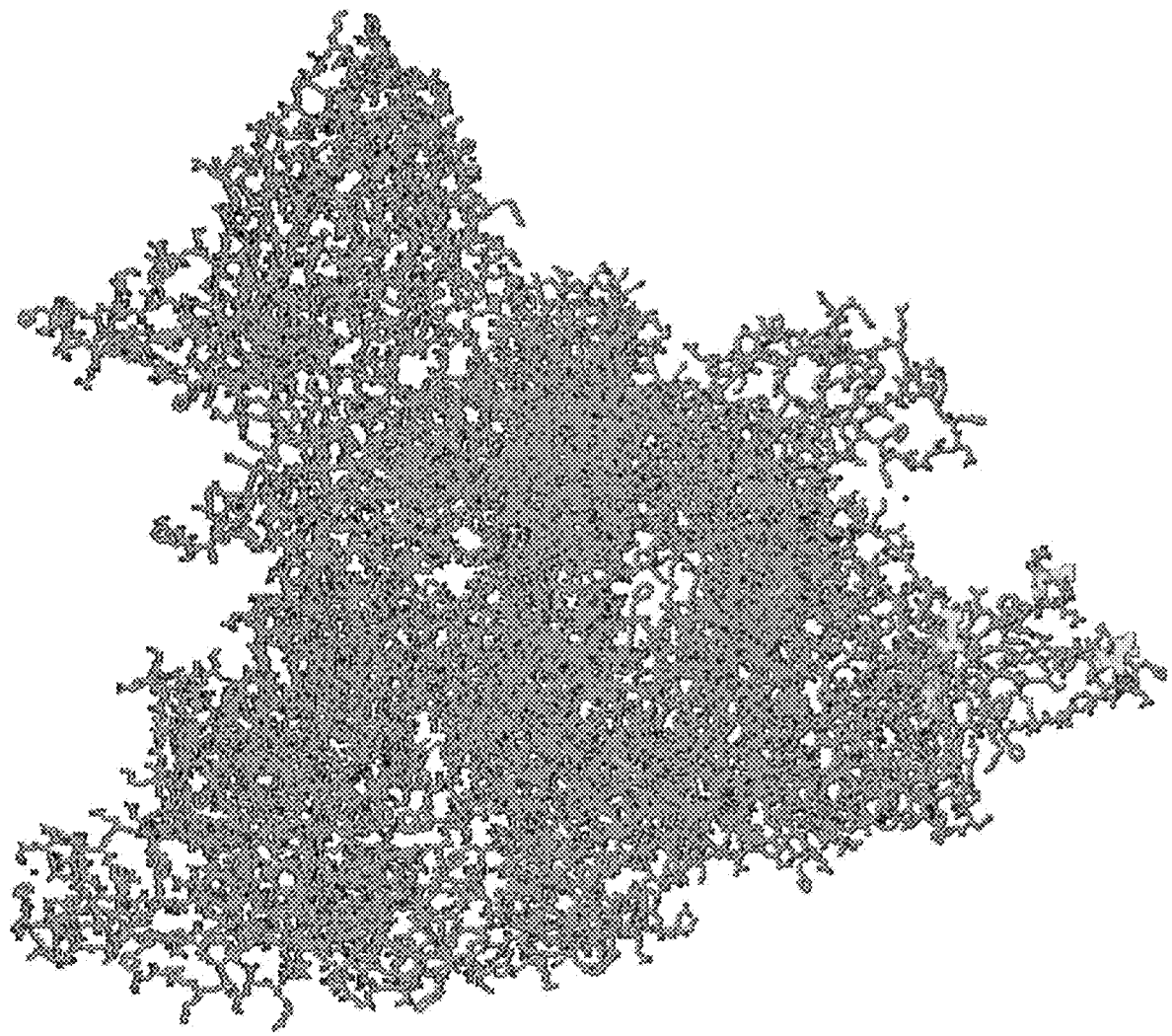
FIG. 10 shows an amino acid map of the knob domain of adenovirus 4 fiber protein with its glutamine residues highlighted. All of the glutamine residues of this protein are localized in the same proximity on the protein surface.
Figure 11:
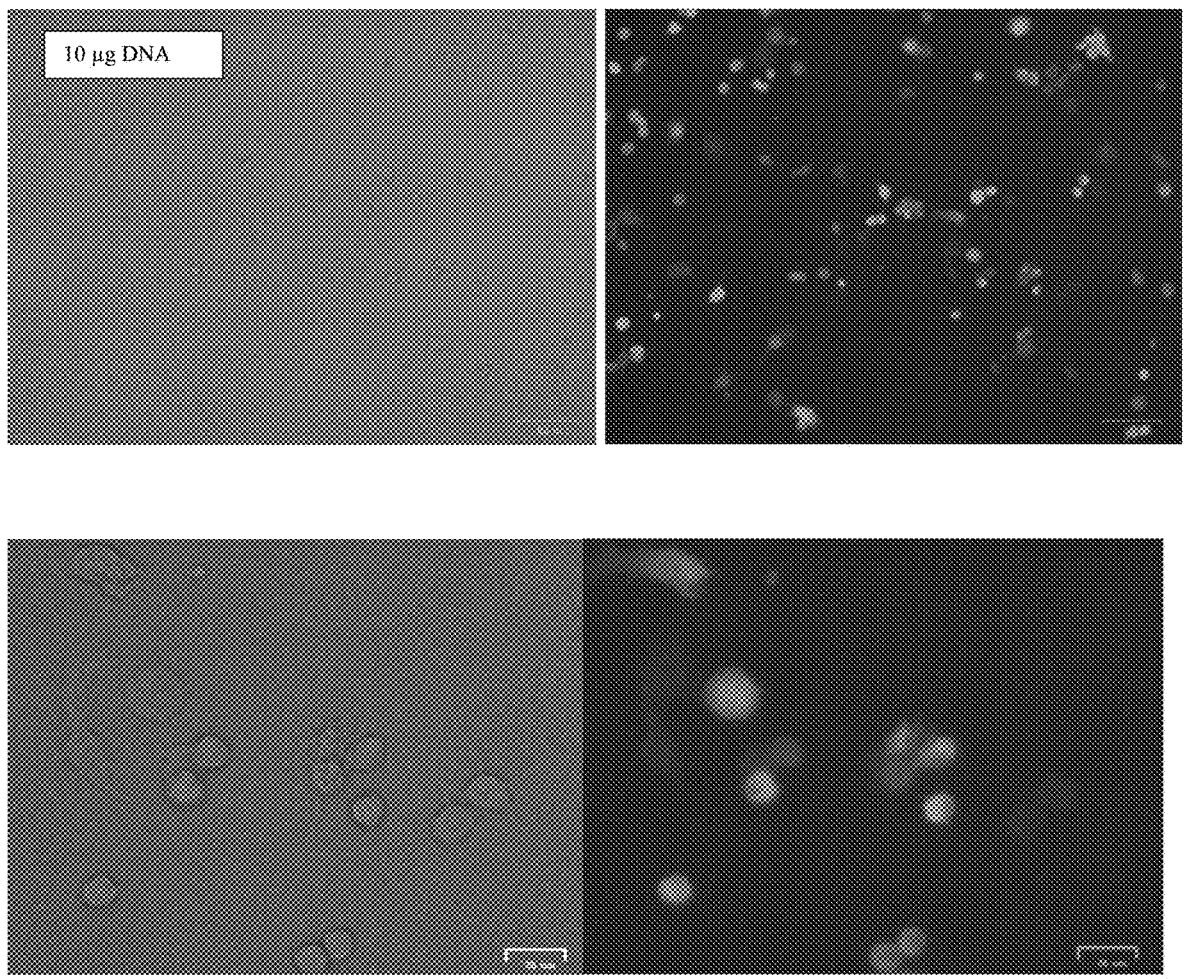
FIG. 11 shows fluorescent micrographs of mouse RAW 264.7 cells transfected with the a virus-based vaccine composed of an Ad5 decorated with polylysine, onto which was bound plasmid DNA encoding green fluorescent protein (GFP) and a spike protein of SARS-CoV-2. The results show that essential every cell present was effectively transfected.
Figure 12:
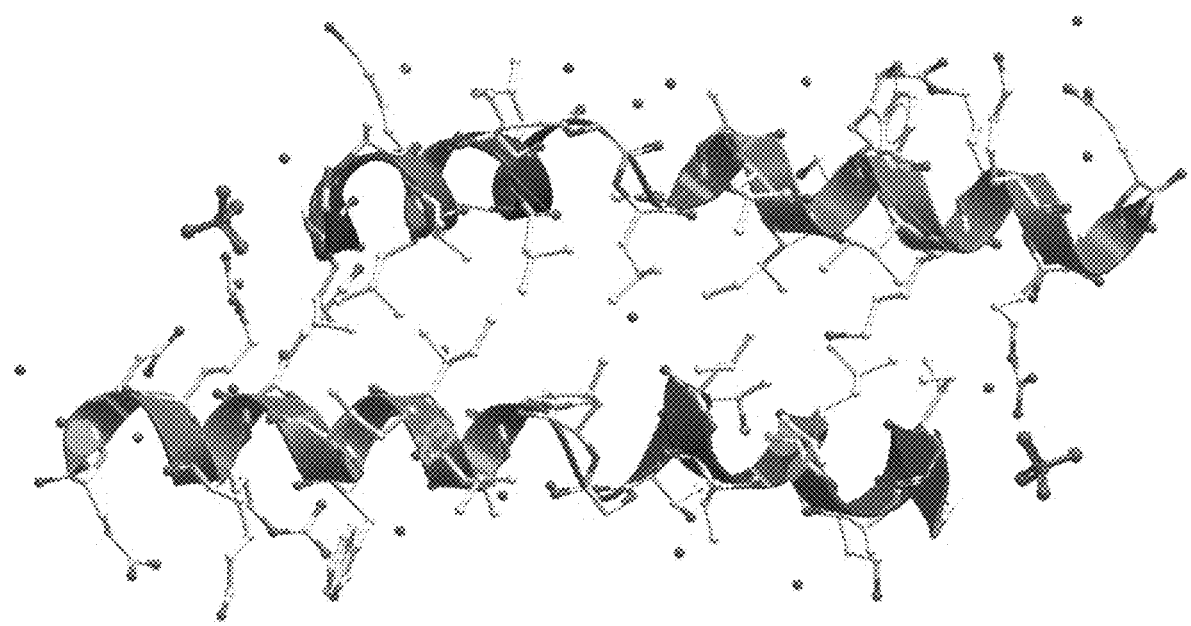
FIG. 12 shows the melittin. 1A shows the amino acid sequence of the peptide, and 1B shows the structure.

The fiber proteins of all human adenovirus serotypes share a common architecture: an N-terminal tail, a central shaft made of repeating sequences, and a C-terminal globular knob domain. The first ~45 residues of the fiber are highly conserved among different serotypes and are responsible for binding to the penton base. As shown in FIG. 10, the knob domain comprises several surface-exposed glutamine residues that provide a functional basis for constructing the disclosed virus-based vaccine platform.

The glutamine residues of the adenovirus fiber knob domain can be functionalized by contacting an isolated adenovirus with transglutaminase. Transglutaminases are enzymes that catalyze the formation of an isopeptide bond between γ-carboxamide groups (—(C=O)NH$_2$) of glutamine residue side chains and the ε-amino groups (—NH$_3$) of lysine residue side chains with subsequent release of ammonia (NH$_3$). Lysine and glutamine residues must be bound to a peptide or a protein so that this cross-linking (between separate molecules) or intramolecular (within the same molecule) reaction can happen. Bonds formed by transglutaminase exhibit high resistance to proteolytic degradation (proteolysis). The reaction is:

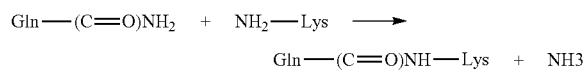

Transglutaminases can also join a primary amine (RNH$_2$) to the side chain carboxyamide group of a protein/peptide bound glutamine residue thus forming an isopeptide bond:

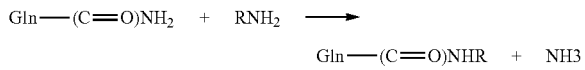

These enzymes can also deamidate glutamine residues to glutamic acid residues in the presence of water:

Thus, incubating adenovirus in the presence of polylysine and transglutaminase results in the polylysine being cross-linked and attached to the exposed glutamine residues of the knob domain of the fiber protein. Upon formation of the polylysine-decorated virus, further incubation with nucleic acid molecules (e.g., DNA), such as an expression vector encoding an immunogenic peptide, results in the binding of the nucleic acids to the polylysine-decorated virus via electrostatic interaction. The resulting virus can function as a vaccine much in the same way as the particle-based platform described above.

While not being bound by theory, it is believed that the decorated virus is phagocytosed by monocytic cells and escapes lysosomal digestion in the same way that an undecorated virus would do so. Once in the cytoplasm of the target monocytic cell, the nucleic acid attached to the surface of the virus via the polylysine can be expressed, such that the immunogenic peptide encoded therein is produced within and subsequently presented on the cell.

While adenovirus may be preferred for this platform, other non-replicative and/or non-infective viruses may additionally be suitable, so long as the virus can be decorated with polylysine. Accordingly, suitable viruses may include, but are not limited to, adenovirus (e.g., adenovirus 5, adenovirus 4), lentivirus (e.g., HIV-derived viruses), and adeno associate virus (e.g., AAV5, AAV9, etc.).

Pharmaceutical Compositions

Pharmaceutical compositions suitable for use in the methods described herein can include the disclosed delivery vectors and a pharmaceutically acceptable carrier or diluent.

In some embodiments, the disclosed delivery vectors may be formulated for parenteral administration by, for example, intradermal, intravenous, intramuscular or subcutaneous injection. Formulations for injection may be presented in unit dosage form, e.g., in ampules or in multi-dose containers, optionally with an added preservative. The compositions may take such forms as suspensions, solutions or emulsions in oily or aqueous vehicles, and may contain formulatory agents such as suspending, stabilizing and/or dispersing agents. The delivery vector may also be formulated using a pharmaceutically acceptable excipient. Such excipients are well known in the art, but typically will be a physiologically tolerable aqueous solution. Physiologically tolerable solutions are those which are essentially non-toxic. Preferred excipients will either be inert or enhancing. Intradermal injection is a preferred route of administration.

In some embodiments, the disclosed vaccines may be formulated to be administered concurrently with another therapeutic agent. In some embodiments, the vaccines may be formulated to be administered in sequence with another therapeutic agent. For example, the vaccine may be administered either before or after the subject has received a regimen of an anti-viral or antibacterial therapy.

Methods of Treatment and Prevention

Provided herein are methods of treating and/or preventing infections and diseases caused by viruses, bacteria, and other pathogenic microbes by administering the disclosed vaccines. More specifically, the disclosure provides for methods of stimulating the immune system to mount an anti-viral or antibacterial response by expressing within a monocytic cell (e.g., an antigen presenting cell) an immunogenic peptide derived from a pathogen (e.g., virus, bacteria, etc.) for which protection from infection is sought. The mechanism of immune stimulation may be multi-faceted and may vary depending on the components of the immunogenic peptide being expressed and the type of monocytic cell expressing the immunogenic peptide.

In some embodiments, the disclosed vaccine may provide to a monocytic cell, such as a macrophage or dendritic cell, a nucleic acid sequence and/or expression vector that encodes at least one immunogenic peptide. In some embodiments, the disclosed vaccines may provide to a monoctyic cell 1, 2, 3, 4, or 5 or more nucleic acid sequences and/or expression vectors that encode 1, 2, 3, 4, or 5 or more different immunogenic peptides. When such an immunogenic peptide is presented on the surface of a monocytic cell, such as an antigen presenting cell, the immune system is stimulated to produce antibodies that bind to the immunogenic peptide and to mount a systemic defense against the pathogen from which the peptide was derived.

For example, in some embodiments, the nucleic acid or expression vector encoding an immunogenic peptide may encode a viral spike protein (also known as "S protein" or "glycoprotein S"), which is generally responsible for viral entry into a host cell. The spike protein is ideal to serve as an immunogenic peptide because antibodies that develop against this peptide are likely to be neutralizing. The spike protein comprises two functional subunits responsible for binding to the host cell receptor ($S_1$ subunit) and fusion of the viral and cellular membranes ($S_2$ subunit). A vaccine of the present disclosure may encode the entire spike protein, only the $S_1$ subunit, only the $S_2$ subunit, or any immunogenic portion thereof. In some embodiments, the vaccine encodes a full length spike protein. In some embodiments, the vaccine encodes only an immunogenic fragment of a viral spike protein. Other viral proteins that may serve as the immunogenic peptide when the target pathogen is a virus include, but are not limited to, a viral E protein, M protein, or N protein, or any other viral capsid or coat protein. In some embodiments, the vaccine encodes a full length E protein, M protein, N protein, or other viral capsid or coat protein, while in some embodiments, the vaccine my encode only an immunogenic fragment of one of these proteins.

Furthermore, when the disclosed vaccine comprises a YCWP as the base particle, the vector can possess even further anti-tumor activity by loading the YCWP with a biological material, such as a tumor lysate. Inclusion of a biological material like a tumor lysate within the YCWP provides a vaccine-like function when the delivery vectors are taken up by an antigen presenting cell (APC) like cells of the mononuclear phagocyte system, including monocytes, macrophages, dendritic cells or immature dendritic cells. In the field of vaccination, cells of the mononuclear phagocyte system are considered "professional" antigen presenting cells and thus, are the ideal target for vaccine delivery. It is well known that presentation of an antigen within an APC is vastly more effective in generating a strong cellular immune response than expression of this same antigen within any other cell type. Accordingly, loading the YWCP with an antigenic biological material like a tumor lysate will result in the presentation of a tumor antigen on an antigen presenting cell via class I MHC and class II MHC molecules, thus dramatically enhancing the immune response elicited by the disclosed delivery vectors.

The disclosed vaccines are highly selective for monocyte cells. It is, therefore, useful for any application involving selectively introducing an expression into a monocyte cell. In some embodiments, the disclosed vectors are administered to treat or prevent an infectious disease, and, in particular, viral or bacterial diseases. In view of the foregoing explanation of the putative mechanism of action, it is believed that the disclosed vaccines may be used to treat or prevent almost any type of infectious disease, which may include, but is not limited to, coronavirus infections (discussed in more detail below), influenza, retroviral infections (e.g., HIV/AIDS), hepatitis A, hepatitis B, hepatitis C, norovirus infections, or infections caused by *Acinetobacter baumannii, Bacteroides fragilis, Burkholderia cepacia, Clostridium difficile, Clostridium sordellii,* Enterobacteriaceae sp., *Enterococcus faecalis, Escherichia coli, Klebsiella pneumonia, Staphylococcus aureus* (including methicillin-resistant strains or MRSA, and vancomycin-resistant or VRSA), *Morganella morganii, Mycobacterium abscessus, Psuedomonas aeruginosa, Stenotrophomonas maltophilia, Mycobacterium tuberculosis,* or *Enterococci* sp. Typical methods of treatment or prevention of a disease or infection (e.g., the foregoing diseases and infections) comprise contacting a monocytic cell with a disclosed vaccine, such that it is phagocytosed by the monocytic cell and the immunogenic is subsequently expressed and presented on the surface of the cell.

As noted above, the vaccines may be injected intradermally, subcutaneously, or systemically (i.e., into the peritoneal of the subject). In some embodiments, the delivery vectors may be administered intradermally proximate a lymph node (e.g., under the arm).

In some embodiments a monocyte cell may be contacted with the disclosed vaccine either in vivo or in vitro. Hence, both in vivo and ex vivo methods of treatment are contemplated herein. In some embodiments, a patient's monocytic cells can be isolated and contacted with the disclosed vaccines in vitro before the cells are returned to the patient. While such embodiments are contemplated in the present disclosure, the disclosed vaccines provide a substantial improvement because they may be used in both in vivo and ex vivo methods. Moreover, altering the route of administration can alter the monocytic cells targeted. For example, in the case of intravenous injection, macrophages may be targeted, and in the case of intradermal and subcutaneous injection.

Dosage regimens can be adjusted to provide the optimum desired response (e.g., production of antibodies against a given pathogen). For example, in some embodiments, a single bolus of vaccine may be administered, while in some embodiments, several divided doses may be administered over time as boosters, or the dose may be proportionally reduced or increased as indicated by the situation. For example, in some embodiments the disclosed vaccines may be administered once or twice weekly by subcutaneous or intradermal injection. In some embodiments, the disclosed delivery vectors may be administered once or twice monthly by subcutaneous or intradermal injection. In some embodiments, the disclosed delivery vectors may be administered once every week, once every other week, once every three weeks, once every four weeks, once every other month, once every three months, once every four months, once every five months, once every six months, once every seven weeks, once every eight weeks, once every three months, once every four months, once every five months, once every six months, or once a year. In some embodiments, a subject may be administered an initial bolus dose and then receive one or more booster doses with a predefined span of time in between each dose (e.g., 1, 2, 3, or 4 week, or 1, 2, 3, 4, 5, 6, 9, or 12 months). In some embodiments, a subject may receive only a single dose (e.g., about $10^8$ particles). In some embodiments, a subject may receive an initial dose followed by one or more subsequent doses of an equal or lesser concentration at a set time after this initial dose, such as 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 or more weeks.

Doses may likewise by adjusted to provide the optimum desired response. For example, in some embodiments, a dose of the disclosed vaccines may comprise $1.0 \times 10^8$ to $1.0 \times 10^{12}$ particles. For example, a single dose may comprise $1.0 \times 10^8$, $1.5 \times 10^8$, $2.0 \times 10^8$, $2.5 \times 10^8$, $3.0 \times 10^8$, $3.5 \times 10^8$, $4.0 \times 10^8$, $4.5 \times 10^8$, $5.0 \times 10^8$, $5.5 \times 10^8$, $6.0 \times 10^8$, $6.5 \times 10^8$, $7.0 \times 10^8$, $7.5 \times 10^8$, $8.0 \times 10^8$, $8.5 \times 10^8$, $9.0 \times 10^8$, $9.5 \times 10^8$, $1.0 \times 10^9$, $1.5 \times 10^9$, $2.0 \times 10^9$, $2.5 \times 10^9$, $3.0 \times 10^9$, $3.5 \times 10^9$, $4.0 \times 10^9$, $4.5 \times 10^9$, $5.0 \times 10^9$, $5.5 \times 10^9$, $6.0 \times 10^9$, $6.5 \times 10^9$, $7.0 \times 10^9$, $7.5 \times 10^9$, $8.0 \times 10^9$, $8.5 \times 10^9$, $9.0 \times 10^9$, $9.5 \times 10^9$, $1.0 \times 10^{10}$, $1.5 \times 10^{10}$, $2.0 \times 10^{10}$, $2.5 \times 10^{10}$, $3.0 \times 10^{10}$, $3.5 \times 10^{10}$, $4.0 \times 10^{10}$, $4.5 \times 10^{10}$, $5.0 \times 10^{10}$, $5.5 \times 10^{10}$, $6.0 \times 10^{10}$, $6.5 \times 10^{10}$, $7.0 \times 10^{10}$, $7.5 \times 10^{10}$, $8.0 \times 10^{10}$, $8.5 \times 10^{10}$, $9.0 \times 10^{10}$, $9.5 \times 10^{10}$, $1.0 \times 10^{11}$, $1.5 \times 10^{11}$, $2.0 \times 10^{11}$, $2.5 \times 10^{11}$, $3.0 \times 10^{11}$, $3.5 \times 10^{11}$, $4.0 \times 10^{11}$, $4.5 \times 10^{11}$, $5.0 \times 10^{11}$, $5.5 \times 10^{11}$, $6.0 \times 10^{11}$, $6.5 \times 10^{11}$, $7.0 \times 10^{11}$, $7.5 \times 10^{11}$, $8.0 \times 10^{11}$, $8.5 \times 10^{11}$, $9.0 \times 10^{11}$, $9.5 \times 10^{11}$, or $1.0 \times 10^{12}$ particles. In some embodiments, the dose may be about $9.5 \times 10^8$, about $9.75 \times 10^8$, about $9.85 \times 10^8$, about $9.95 \times 10^8$, about $1.0 \times 10^9$, about $1.1 \times 10^9$, about $1.15 \times 10^9$, about $1.2 \times 10^9$, about $1.25 \times 10^9$, about $1.3 \times 10^9$, about $1.35 \times 10^9$, about $1.4 \times 10^9$, about $1.45 \times 10^9$, or about $1.5 \times 10^9$ particles.

Furthermore, while the subject of the methods is generally a human patient, the age of the patient is not limited. The disclosed methods are useful for preventing infectious diseases in patients with various levels of risk exposure and prognostic outcomes, across all age groups and cohorts. Thus, in some embodiments, the subject may be a pediatric subject, while in other embodiments, the subject may be an adult subject, while in other embodiments, the subject may be 60, 65, 70, 75, or 80 years of age or older.

In sum, the disclosed methods provide a broad spectrum approach to preventing and treating infectious diseases, such as viral, bacterial, and other microbial diseases, using a platform that relies on expression of an immunogenic peptide by antigen presenting cells. The disclosed nucleic acid vaccine platforms provide a simple and flexible approach that can be readily adapted to elicit an immune response to any type of pathogen.

The following examples are given to illustrate the present disclosure. It should be understood that the invention is not to be limited to the specific conditions or details described in these examples.

Coronaviruses and Coronavirus Infections

The vaccines and pharmaceutical compositions described herein may be administered to a subject to treat or prevent a disease in a subject in need thereof, in particular when the disease is a viral infection, such as a coronavirus infection (e.g., COVID-19). Further disclosed herein are uses of any of the vaccines or pharmaceutical compositions disclosed herein in the manufacture of a medicament for treating or preventing a viral infection, such as a coronavirus infection (e.g., COVID-19).

In some embodiments of the disclosed method and uses, the disease being treated is a viral disease. In some embodiments, the viral disease is caused by an RNA virus. In some embodiments, the RNA virus is a single-stranded RNA virus (ssRNA virus). In some embodiments, the ssRNA virus is a positive-sense single-stranded RNA virus ((+)ssRNA virus). In some embodiments, the (+)ssRNA virus is a coronavirus.

Coronaviruses are a family of viruses (i.e., the coronaviridae family) that cause respiratory infections in mammals and that comprise a genome that is roughly 30 kilobases in length. The coronaviridae family is divided into four genera and the genome encodes 28 proteins across multiple open reading frames, including 16 non-structural proteins.

The coronaviridae family includes both α-coronaviruses or β-coronaviruses, which both mainly infect bats, but can also infect other mammals like humans, camels, and rabbits. β-coronaviruses have, to date, been of greater clinical importance, having caused epidemics including severe acute respiratory syndrome (SARS), Middle East respiratory syndrome (MERS), and COVID-19. The disclosed vaccines and pharmaceutical compositions may be used to treat or prevent diseases caused by β-coronaviruses and α-coronaviruses. Thus, in some embodiments of the disclosed methods and uses the coronavirus is a β-coronavirus, such as severe acute respiratory syndrome coronavirus 2 (SARS-CoV-2) (also known by the provisional name 2019 novel coronavirus, or 2019-nCoV), human coronavirus OC43 (hCoV-OC43), Middle East respiratory syndrome-related coronavirus (MERS-CoV, also known by the provisional name 2012 novel coronavirus, or 2012-nCoV), and severe acute respiratory syndrome-related coronavirus (SARS-CoV, also known as SARS-CoV-1). In some embodiments of the disclosed methods and uses the coronavirus is a α-coronavirus.

Several disease-causing coronaviruses share a high degree of homology across their genomes. Accordingly, the disclosed vaccines and pharmaceutical compositions may provide a broad spectrum treatment or preventative effect for multiple different types of coronavirus, such as MERS-CoV, SARS-CoV-1, and SARS-CoV-2.

In some embodiments of the disclosed methods and uses, the immunogenic peptide encoded by the nucleic acid vaccine may be all or a portion of a structural protein from a coronavirus, such as SARS-CoV-2. In some embodiments, the immunogenic peptide is selected from genome of SARS-CoV-2, which corresponds to the nucleotide sequence of GenBank Accession No. NC_045512.2, and which is incorporated by reference in its entirety. The SARS-COV-2 genome is also shown in Table 1 below.

In some embodiments, the immunogenic peptide may be all or a portion of the spike protein (also known as "S protein" or "glycoprotein S"), which is responsible for viral entry into a host cell. The spike protein is ideal to serve as an immunogenic peptide because antibodies that develop against this peptide are likely to be neutralizing. The spike protein comprises two functional subunits responsible for binding to the host cell receptor ($S_1$ subunit) and fusion of the viral and cellular membranes ($S_2$ subunit). The SARS-COV-2 spike protein (NCBI Reference Sequence: YP_009724390.1) comprises 1273 amino acids shown below.

(SEQ ID NO: 1)
MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPRRARSVASQSIIAYTMSLG

AENSVAYSNNSIAIPTNFTISVTTEILPVSMTKTSVDCTMYICGDSTECS

NLLLQYGSFCTQLNRALTGIAVEQDKNTQEVFAQVKQIYKTPPIKDFGGF

NFSQILPDPSKPSKRSFIEDLLFNKVTLADAGFIKQYGDCLGDIAARDLI

CAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQD

VVNQNAQALNTLVKQLSSNFGAISSVLNDILSRLDKVEAEVQIDRLITGR

LQSLQTYVTQQLIRAAEIRASANLAATKMSECVLGQSKRVDFCGKGYHLM

SFPQSAPHGVVFLHVTYVPAQEKNFTTAPAICHDGKAHFPREGVFVSNGT

HWFVTQRNFYEPQIITTDNTFVSGNCDVVIGIVNNTVYDPLQPELDSFKE

ELDKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCCSC

GSCCKFDEDDSEPVLKGVKLHYT

A vaccine of the present disclosure may encode the entire spike protein (SEQ ID NO: 1), only the $S_1$ subunit, only the $S_2$ subunit, or any immunogenic portion thereof. In some embodiments, the vaccine encodes SEQ ID NO: 1. In some embodiments, the vaccine encodes about 50%, about 55%, about 60%, about 65%, about 70%, about 75%, about 80%, about 85%, about 90%, 91%, 92%, 93%, 94%, 95%, 96%, 97%, 98%, or 99% of SEQ ID NO: 1, so long as the fragment is able to elicit an immune response (i.e., it is an immunogenic fragment).

The vaccines of the present disclosure may be used to treat or prevent an infectious disease in a subject in need thereof. In some embodiments, a method of treating or preventing a disease in a subject in need thereof comprises administering to the subject any of the nucleic acid vaccines disclosed herein. In some embodiments, a method of treating or preventing a disease in a subject in need thereof comprises administering to the subject any of the pharmaceutical compositions disclosed herein.

In some embodiments of the disclosed methods and uses, the disease is a respiratory disease. In some embodiments, the respiratory disease is a viral infection. In some embodiments, the respiratory disease is viral pneumonia. In some embodiments, the respiratory disease is an acute respiratory infection. In some embodiments, the respiratory disease is coronavirus disease 2019 (COVID-19). In some embodiments, the respiratory disease can include one or more symptoms selected from coughing, sore throat, runny nose, sneezing, headache, fever, shortness of breath, myalgia, abdominal pain, fatigue, difficulty breathing, persistent chest pain or pressure, difficulty waking, loss of smell and taste, muscle or joint pain, chills, nausea or vomiting, nasal congestion, diarrhea, hemoptysis, conjunctival congestion, sputum production, chest tightness, and palpitations. In some embodiments, the respiratory disease can include complications selected from sinusitis, otitis media, pneumonia, acute respiratory distress syndrome, disseminated intravascular coagulation, pericarditis, and kidney failure.

In some embodiments, the subject is a mammal. In some embodiments, the subject is a human. In some embodiments, the subject is a non-human primate. In some embodiments, the subject is a cat, dog, cow, pig, horse, sheep, goat, or rodent. In some embodiments in which the subject is a human, the subject may be at least 40 years old, at least 45 years old, at least 50 years old, at least 55 years old, at least 60 years old, at least 65 years old, at least 70 years old, at least 75 years old, or at least 80 years old or older. In some embodiments, the human subject is a pediatric subject (i.e., less than 18 years old).

The vaccines of the present disclosure may be given in any forms suitable for administration, which generally comprises an injection. Preferably, the disclosed vaccines are administered intradermally, intramuscularly, or subcutaneously. In some embodiments, the vaccines are administered via intradermal injection.

In some embodiments, the present disclosure provides methods of treating or preventing a coronavirus infection, comprising administering to a subject in need thereof a therapeutically effective amount of one or more of the nucleic acid vaccines or a pharmaceutical composition as disclosed herein. In some embodiments, the coronavirus infection is selected from the group consisting of Middle East Respiratory Syndrome (MERS), Severe Acute Respiratory Syndrome (SARS), and COVID-19. In some embodiments, the subject has been treated with one or more additional coronavirus treatment agents. In some embodiments, the subject is concurrently treated with one or more additional coronavirus treatment agents.

Actual dosage levels of the nucleic acid vaccines in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular vaccine, the route of administration, the time of administration, the duration of the treatment, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the vaccines of the disclosure employed in the pharmaceutical composition at levels lower than that required in order to achieve the desired therapeutic effect and gradually increase the dosage until the desired effect is achieved.

TABLE 1

Genome Sequence of SARS-CoV-2

| SEQ ID NO: | Description | Sequence |
|---|---|---|
| 2 | SARS-CoV-2 | attaaaggtttataccttcccaggtaacaaaccaaccaactttcgatctcttgtagatctgttctctaaacgaactttaaaatctgtgtggctgtcactcggctgcatgcttagtg |
| | genome | cactcacgcagtataattaataactaattactgtcgttgacaggacacgagtaactcgtctatcttctgcaggctgcttacggtttcgtccgtgttgcagccgatcatcagca |
| | Genbank | catctaggtttcgtccgggtgtgaccgaaaggtaagatggagagccttgtccctggtttcaacgagaaaacacacgtccaactcagtttgcctgttttacaggttcgcgac |
| | Acccssion No. | gtgctcgtacgtggctttggagactccgtggaggaggtcttatcagaggcacgtcaacatcttaaagatggcacttgtggcttagtagaagttgaaaaaggcgttttgcct |
| | NC_045512.2 | caacttgaacagccctatgtgttcatcaaacgttcggatgctcgaactgcacctcatggtcatgttatggttgagctggtagcagaactcgaaggcattcagtacggtcgta |
| | | gtggtgagacacttggtgtccttgtccctcatgtgggcgaaataccagtggcttaccgcaaggttcttcttcgtaagaacggtaataaaggagctggtggccatagttacg |
| | | gcgccgatctaaagtcatttgacttaggcgacgagcttggcactgatccttatgaagattttcaagaaaactggaacactaaacatagcagtggtgttacccgtgaactcat |
| | | gcgtgagcttaacggaggggcatacactcgctatgtcgataacaacttctgtggccctgatggctaccctcttgagtgcattaaagaccttctagcacgtgctggtaaagc |
| | | ttcatgcactttgtccgaacaactggactttattgacactaagaggggtgtatactgctgccgtgaacatgagcatgaaattgcttggtacacggaacgttctgaaaagagc |
| | | tatgaattgcagacaccttttgaaattaaattggcaaagaaatttgacaccttcaatggggaatgtccaaattttgtatttcccttaaattccataatcaagactattcaaccaag |
| | | ggttgaaaagaaaaagcttgatggctttatgggtagaattcgatctgtctatccagttgcgtcaccaaatgaatgcaaccaaatgtgcctttcaactctcatgaagtgtgatc |
| | | attgtggtgaaacttcatggcagacgggcgattttgttaaagccacttgcgaattttgtggcactgagaatttgactaaagaaggtgccactacttgtggttacttaccccaa |
| | | aatgctgttgttaaaatttattgtccagcatgtcacaattcagaagtaggacctgagcatagtcttgccgaataccataatgaatctggcttgaaaaccattcttcgtaagggt |
| | | ggtcgcactattgcctttggaggctgtgtgttctcttatgttggttgccataacaagtgtgcctattgggttccacgtgctagcgctaacataggttgtaaccatacaggtgttg |
| | | ttggagaaggttccgaaggtcttaatgacaaccttcttgaaatactccaaaaagagaaagtcaacatcaatattgttggtgactttaaacttaatgaagagatcgccattattt |
| | | tggcatctttttctgcttccacaagtgcttttgtggaaactgtgaaaggtttggattataaagcattcaaacaaattgttgaatcctgtggtaattttaaagttacaaaaggaaaa |
| | | gctaaaaaaggtgcctggaatattggtgaacagaaatcaatactgagtcctctttatgcatttgcatcagaggctgctcgtgttgtacgatcaatttctcccgcactcttgaa |
| | | actgctcaaaattctgtgcgtgttttacagaaggccgctataacaatactagatggaatttcacagtattcactgagactcattgatgctatgatgttcacatctgatttggcta |
| | | ctaacaatctagttgtaatggcctacattacaggtggtgttgttcagttgacttcgcagtggctaactaacatctttggcactgtttatgaaaaactcaaacccgtccttgattg |
| | | gcttgaagagaagtttaaggaaggtgtagagtttcttagagacggttgggaaattgttaaatttatctcaacctgtgcttgtgaaattgtcggtggacaaattgtcacctgtgc |
| | | aaaggaaattaaggagagtgttcagacattattaagcttgtaaataaatttttggattgtgtgctgactctatcattattggtggagctaaacttaaagccttgaatttaggtg |
| | | aaacatttgtcacgcactcaaagggattgtacagaaagtgtgttaaatccagagaagaaactggcctactcatgcctctaaaagccccaaaagaaattatcttcttagagg |
| | | gagaaacacttcccacagaagtgttaacagaggaagttgtcttgaaaactggtgatttacaaccattagaacaacctactagtgaagctgttgaagctccattggttggtac |
| | | accagtttgtattaacgggcttatgttgctcgaaatcaaagacacagaaaagtactgtgcccttgcacctaatatgatggtaacaaacaataccttcacactcaaaggcggt |
| | | gcaccaacaaaggttacttttggtgatgacactgtgatagaagtgcaaggttacaagagtgtgaatatcacttttgaacttgatgaaaggattgataaagtacttaatgagaa |
| | | gtgctctgcctatacagttgaactcggtacagaagtaaatgagttcgcctgtgttgtggcagatgctgtcataaaaactttgcaaccagtatctgaattacttacaccactgg |
| | | gcattgatttagatgagtggagtatggctacatactacttatttgatgagtctggtgagtttaaattggcttcacatatgtattgttctttctaccctccagatgaggatgaagaa |
| | | gaaggtgattgtgaagaagaagagtttgagccatcaactcaatatgagtatggtactgaagatgattaccaaggtaaacctttggaatttggtgccacttctgctgctatca |
| | | acctgaagaagagcaagaagaagattggttagatgatgatagtcaacaaactgttggtcaacaagacggcagtgaggacaatcagacaactactattcaaacaattgtt |
| | | gaggttcaacctcaattagagatggaacttacaccagttgttcagactattgaagtgaatagttttagtggttatttaaaacttactgacaatgtatacattaaaaatgcagaca |
| | | ttgtggaagaagctaaaaaggtaaaaccaacagtggttgttaatgcagccaatgtttaccttaaacatggaggaggtgttgcaggagccttaaataaggctactaacaatg |
| | | ccatgcaagttgaatctgatgattacatagctactaatggaccacttaaagtgggtggtagttgtgttttaagcggacacaatcttgctaaacactgtcttcatgttgtcggcc |
| | | caaatgttaacaaaggtgaagacattcaacttcttaagagtgcttatgaaaattttaatcagcacgaagttctacttgcaccattattatcagctggtattttttggtgctgaccct |
| | | atacattattaagagtttgtgtagatactgttcgcacaaatgtctacttagctgtctttgataaaaatctctatgacaaacttgtttcaagcttttggaaatgaagagtgaaaag |
| | | caagttgaacaaaagatcgctgagattcctaaagaggaagttaagccatttataactgaaagtaaaccttcagttgaacagagaaaacaagatgataagaaaatcaaagc |
| | | ttgtgttgaagaagttacaacaactaggaagaaactaagttcctcacagaaaacttgttactttatattgacattaatggcaatcttcatccagattctgccactcttgttagtg |
| | | acattgacatcactttcttaaagaaagatgaccatatatagtgggtgatgttgttcaagagggtgttttaactgctgtggttatacctactaaaaaggctggtggcactactg |
| | | aaatgctagcgaaagctttgagaaaagtgccaacagacaattatataaccacttacccgggtcagggtttaaatggttacactgtagaggaggcaaagacagtgcttaaa |
| | | aagtgtaaaagtgccttttacattctaccatctattatctctaatgagaagcaagaaattcttggaactgtttcttggaatttgcgagaaatgcttgcacatgcagaagaaaca |
| | | cgcaaattaatgcctgtctgtgtggaaactaaagccatagtttcaactatacagcgtaaatataagggtattaaaatacaagagggtgtggttgattatggtgctagattttac |
| | | ttttacaccagtaaaacaactgtagcgtcacttatcaacacacttaacgatctaatgaaactcttgttacaatgccacttggctatgtaacacatggcttaaatttggaagaa |
| | | gctgctcggtatatgagatctctcaaagtgccagctacagtttctgtttcttcacctgatgctgttacagcgtataatggttatcttacttcttcttctaaaacacctgaagaacat |
| | | tttattgaaaccatctcacttgctggttcctataaagattggtcctattctggacaatctacacaactaggtatagaatttcttaagagaggtgataaaagtgtatattacactag |
| | | taatcctaccacattccacctagatggtgaagttatcacctttgacaatcttaagacacttattattgagagaagtgaggactattaaggtgtttacaacagtagacaacatt |
| | | aacctccacacgcaagttgtggacatgtcaatgacatatggacaacagtttggtccaacttatttggatggagctgatgttactaaaataaaacctcataattcacatgaag |
| | | gtaaaacattttatgttttacctaatgatgacactctacgtgttgaggcttttgagtactaccacacaactgatcctagttttctgggtaggtacatgtcagcattaaatcacact |

TABLE 1-continued

Genome Sequence of SARS-CoV-2

| SEQ ID NO: | Description | Sequence |
|---|---|---|
| | | aaaaagtggaaatacccacaagttaatggtttaacttctattaaatgggcagataacaactgttatcttgccactgcattgttaacactccaacaaatagagttgaagtttaat<br>ccacctgactacaagatgcttattacagagcaagggctggtgaagctgctaacttttgtgcacttatcttagcctactgtaataagacagtaggtgagttaggtgatgttag<br>agaaacaatgagttacttgtttcaacatgccaatttagattcttgcaaaagagtcttgaacgtggtgtgtaaaacttgtggacaacagcagacaacccttaagggtgtagaa<br>gctgttatgtacatgggcacactttcttatgaacaatttaagaaaggtgttcagataccttgtacgtgtggtaaacaagctacaaaatatctagtacaacaggagtcaccttttt<br>gttatgatgtcagcaccacctgctcagtatgaacttaagcatggtacatttacttgtgctagtgagtacactggtaattaccagtgtggtcactataaacatataacttctaaag<br>aaactttgtattgcatagacggtgattacttacaaagtcctcagaatacaaaggtcctattacggatgttttctacaaagaaaacagttacacaacaaccataaaaccagtta<br>cttataaattggatggtgttgtttgtacagaaattgaccctaagttggacaattattataagaaagacaattcttatttcacagagcaaccaattgatcttgtaccaaaccaacc<br>atatccaaacgcaagcttcgataattttaagtttgtatgtgataatatcaaatttgctgatgatttaaaccagttaactggttataagaaacctgcttcaagagagcttaaagtta<br>catttttccctgacttaaatggtgatgtggtggctattgattataaacactacacaccctcttttaagaaaggagctaaattgttacataaacctattgtttggcatgttaacaatg<br>caactaataaagccacgtataaaccaaatacctggtgtatacgttgtctttggagcacaaaaccagttgaaacatcaaattcgtttgatgtactgaagtcagaggacgcgc<br>agggaatggataatcttgcctgcgaagatctaaaaccagtctctgaagaagtagtggaaaatcctaccatacagaaagacgttcttgagtgtaatgtgaaaactaccgaa<br>gttgtaggagacattatacttaaaccagcaaataatagtttaaaaattacagaagaggttggccacacagatctaatggctgcttatgtagacaattctagtcttactattaag<br>aaacctaatgaattatctagagtattaggtttgaaaacccttgctactcatggtttagctgctgttaatagtgtcccttgggatactatagctaattatgctaagccttttcttaaca<br>aagttgttagtacaactactaacatagttacacggtgtttaaaccgtgtttgtactaattatatgccttatttattactttattgctacaattgtgtacttttactagaagtacaaattc<br>tagaattaaagcatctatgccgactactatagcaaagaatactgttaagagtgtcggtaaattttgtctagaggcttcatttaattatttgaagtcacctaattttctaaactgat<br>aaatattataatttggtttttactattaagtgtttgcctaggttattaatctactcaaccgctgattaggtgttttaatgtctaatttaggcatgccttcttactgtactggttacaga<br>gaaggctatttgaactctactaatgtcactattgcaacctactgtactggttctataccttgtagtgtttgtcttagtggtttagattattagacacctatccttattagaaactata<br>caaattaccatttcatatttaaatgggatttaactgatttggcttagttgcagagtggtttttggcatatattatttcactaggtttttctatgtacttggattggctgcaatcatgc<br>aattgtttttcagctattttgcagtacattttattagtaattcttggcttatgtggttaataattaatcttgtacaaatggccccgatttcagctatggttagaatgtacatcttctttgc<br>atcattttattatgtatggaaaagttatgtgcatgttgtagacggttgtaattcatcaacttgtatgatgtgttacaaacgtaatagagcaacaagagtcgaatgtacaactattg<br>ttaatggtgttagaaggtcctttatgtctatgctaatggaggtaaaggcttttgcaaactacacaattggaattgtgttaattgtgatacattctgtgctggtagtacatttattag<br>tgatgaagttgcgagagacttgtcactacagtttaaaagaccaataaatcctactgaccagtcttcttacatcgttgatagtgttacagtgaagaatggttccatccatctttac<br>tttgataaagctggtcaaaagacttatgaaagacattctactctcattttgttaacttagacaacctgagagctaataacactaaaggttcattgcctattaatgttatagtttttg<br>atggtaaatcaaaatgtgaagaatcatctgcaaaatcagcgtagtttactacagtcagcttatgtgtcaacctatactgttactagatcaggcattagtgtctgatgttggtga<br>tagtgcggaagttgcagttaaaatgtttgatgcttacgttaatacgttttcatcaacttttaacgtaccaatggaaaaactcaaaacactagttgcaactgcagaagctgaact<br>tgcaaagaatgtgtccttagacaatgtcttatctactttatttcagcagctcggcaagggtttgttgattcagatgtagaaactaaagatgttgttgaatgtcttaaattgtcaca<br>tcaatctgacatagaagttactggcgatagttgtaataactatatgctcacctataacaaagttgaaaacatgacaccccgtgaccttggtgcttgtattgactgtagtgcgc<br>gtcatattaatgcgcaggtagcaaaaagtcacaacattgctttgatatggaacgttaaagatttcatgtcattgtctgaacaactacgaaaacaaatacgtagtgctgctaaa<br>aagaataacttacctttaagttgacatgtgcaactactagacaagttgttaatgttgtaacaacaaagatagcacttaagggtggtaaaattgttaataattggttgaagcagt<br>taattaaagttacacttgtgttcctttttgttgctgctattttctatttaataacacctgttcatgtcatgtctaaacatactgacttttcaagtgaaatcataggatacaaggctattg<br>atggtggtgtcactcgtgacatagcatctacagatacttgttttgctaacaaacatgctgattttgacacatggtttagccagcgtggtggtagttatactaatgacaaagctt<br>gcccattgattgctgcagtcataacaagagaagtgggttttgtcgtgcctggtttgcctggcacgatattacgcacaactaatggtgacttttttgcatttcttacctagagtttttt<br>agtgcagttggtaacatctgttacacaccatcaaaacttatagagtacactgactttgcaacatcagcttgtgttttggctgctgaatgtacaatttttaaagatgcttctggtaa<br>gccagtaccatattgttatgataccaatgtactagaaggttctgttgcttatgaaagtttacgccctgacacacgttatgtgctcatggatggctctattattcaatttcctaaca<br>cctaccttgaaggttctgttagagtggtaacaacttttgattctgagtactgtaggcacggcacttgtgaaagatcagaagctggtgtttgtgtatctactagtggtagatggg<br>tacttaacaatgattattacagatattaccaggagttttctgtggtgtagatgctgtaaatttacttactaatatgtttacaccactaattcaacctattggtgattggacatatca<br>gcatctatagtagaggtggtattgtagctatcgtagtaacatgccttgcctactattttatgaggtttagaagagcttttggtgaatacagtcatgtagttgcctttaatactttac<br>tattccttatgtcattcactgtactagtttaacaccagtttactcattcttacctggtgtttattctgttatttacttgtacttgacattttatcttactaatgatgtttctttttttagcacata<br>ttcagtggatggttatgttcacacctttagtacctttctggataacaattgcttatatcatttgtatttccacaaagcatttctattggttctttagtaattacctaaagagacgtgta<br>gtattaatggtgtttcctttagtacttttgaagaagctgcgctgtgcaccttttttgttaaataaagaaatgtatctaaagttgcgtagtgatgtgctattacctcttacgcaatata<br>atagatacttagctctttataataagtacaagtattttagtggagcaatggatacaactagctacagagaagctgcttgttgtcatctcgcaaaggctctcaatgacttcagta<br>actcaggttctgatgttattaccaaccaccacaaacctctatcacctcagctgttttgcagagtggttttagaaaaatggcattcccatctggtaaagttgagggttgtatggt<br>acaagtaacttgtggtacaactacacttaacggtattggcttgatgacgtagtttactgtccaagacatgtgatctgcacctctgaagacatgcttaaccctaattatgaaga<br>tttactcattcgtaagtctaatcataatttcttggtacaggctggtaatgttcaactcagggttattggacattctatgcaaaattgtgtacttaagcttaaggttgatacagccaa<br>tcctaagacacctaagtataagtttgttcgcattcaaccaggacagactttttcagtgttagcttgttacaatggttcaccatctggtgtttaccaatgtgctatgaggcccaatt<br>tcactattaagggttcattccttaatggttcatgtggtagtgttggttttaacatagattatgactgtgtctcttttttgttacatgcaccatatggaattaccaactggagttcatgct<br>ggcacagacttagaaggtaacttttatggaccttttgttgacaggcaaacagcacaagcagctggtacggacacaactattacagttaatgttttagcttggttgtacgctgc<br>tgttataaatggagacaggtggtttctcaatcgatttaccacaactcttaatgactttaaccttgtggctatgaagtacaattatgaacctctaacacaagaccatgttgacata |

TABLE 1-continued

Genome Sequence of SARS-CoV-2

SEQ ID
NO: Description  Sequence ctaggacctcttctgctcaaactgaattgcctgttctcaaactgaattgcctgttcttagatatgtgtcttcattaaagaattactgcaaatgtaatgaatgtagtgaatgactgaccatattggtagtgcttattga
agatgaattacaccttgatgtgtagaacaatgtcaggtgttactt TABLE 1-continued Genome Sequence of SARS-CoV-2

| SEQ ID NO: | Description | Sequence |
|---|---|---|
| | | atgtcatatcaacatcacataaattagtcttgtctgttaatccgtatgtttgcaatgctccaggttgtgatgtcacagatgtgactcaactttacttaggaggtatgagctattatt<br>gtaaatcacataaaccacccattagttttccattgtgtgctaatggacaagtttttggtttatataaaaatacatgtgttggtagcgataatgttactgactttaatgcaattgcaa<br>catgtgactggacaaatgctggtgattacattttagctaacacctgtactgaaagactcaagattttgcagcagaaacgctcaaagctactgaggagacatttaaactgtct<br>tatggtattgctactgtacgtgaagtgctgtctgacagagaattacatctttcatgggaagttggtaaacctagaccaccacttaaccgaaattatgtattactggttatcgtg<br>taactaaaaacagtaaagtacaaataggagagtacacctttgaaaaaggtgactatggtgatgctgttgtttaccgaggtacaacaacttacaaattaaatgttggtgattat<br>tttgtgctgacatcacatacagtaatgccattaagtgcacctacactagtgccacaagagcactatgttagaattactggcttatacccaacactcaatatctcagatgagttt<br>tctagcaatgttgcaaattatcaaaaggttggtatgcaaaagtattctacactccagggaccacctggtactggtaagagtcattttgctattggcctagctctctactaccctt<br>ctgctcgcatagtgtatacagcttgctctcatgccgctgttgatgcactatgtgagaaggcattaaaatatttgcctatagataaatgtagtagaattatacctgcacgtgctc<br>gtgtagagtgttttgataaattcaaagtgaattcaacattagaacagtatgtatttgtactgtaaatgcattgcctgagacgacagcagatatagttgtctttgatgaaatttca<br>atggccacaaattatgatttgagtgttgtcaatgccagattacgtgctaagcactatgtgtacattggcgaccctgctcaattacctgcaccacgcacattgctaactaaggg<br>cacactagaaccagaatatttcaattcagtgtgtagacttatgaaaactataggtccagacatgttcctcggaacttgtcggcgttgtcctgctgaaattgttgacactgtgag<br>tgattggtttatgataataagcttaaagcacataaagacaaatcagctcaatgattaaaatgttttataagggtgttatcacgcatgatgtttcatctgcaattaacaggccac<br>aaataggcgtggtaagagaattccttacacgtaaccctgcttggagaaaagctgtctttatttcaccttataattcacagaatgctgtagcctcaaagattttgggactaccaa<br>ctcaaactgttgattcatcacagggctcagaatatgactatgtcatattcactcaaaccactgaaacagctcactcttgtaatgtaaacagatttaatgttgctattaccagagc<br>aaaagtaggcatactttgcataatgtctgatagagacctttatgacaagttgcaatttacaagtcttgaaattccacgtaggaatgtggcaactttacaagctgaaaatgtaac<br>aggactctttaaagattgtagtaaggtaatcactgggttacatcctacacaggcacctacacacctcagtgttgacactaaattcaaaactgaaggtttatgtgttgacatac<br>ctggcatacctaaggacatgacctatagaagactcatctctatgatgggttttaaaatgaattatcaagttaatggttaccctaacatgtttatcacccgcgaagaagctataa<br>gacatgtacgtgcatggattggcttcgatgtcgaggggtgtcatgctactagagaagctgttggtaccaatttacctttacagctaggtttttctacaggtgttaacctagttg<br>ctgtacctacaggttatgttgatacacctaataatacagatttttccagagttagtgctaaaccaccgcctggagatcaatttaaacacctcataccacttatgtacaaaggac<br>ttccttggaatgtagtgcgtataaagattgtacaaatgttaagtgacacacttaaaaatctctctgacagagtcgtatttgtcttatgggcacatggctttgagttgacatctatg<br>aagtattttgtgaaaataggacctgagcgcacctgttgtctatgtgatagacgtgccacatgatttccactgcttcagacacttatgcctgttggcatcattctattggatttga<br>ttacgtctataatccgtttatgattgatgttcaacaatggggttttacaggtaacctacaaagcaaccatgatctgtattgtcaagtccatggtaatgcacatgtagctagttgtg<br>atgcaatcatgactaggtgtctagctgtccacgagtgattgttaagcgtgttgactggactattgaatatcctataattggtgatgaactgaagattaatgcggcttgtagaa<br>aggttcaacacatggttgttaaagctgcattattagcagacaaattcccagttcttcacgacattggtaaccctaaagctattaagtgtgtacctcaagctgatgtagaatgg<br>aagttctatgatgcacagccttgtagtgacaaagcttataaaatagaagaattattctattcttatgccacacattctgacaaattcacagatggtgtatgcctattttggaattg<br>caatgtcgatagatatcctgctaattccattgtttgtagatttgacactagagtgctatctaaccttaacttgcctggttgtgatggtggcagtttgtatgtaaataaacatgcatt<br>ccacacaccagcttttgataaaagtgatttgttaatttaaaacaattaccatttttctattactctgacagtccatgtgagtctcatggaaaacaagtagtgtcagatatagatta<br>tgtaccactaaagtctgctacgtgtataacacgttgcaatttaggtggtgctgtctgtagacatcatgctaatgagtacagattgtatctcgatgcttataacatgatgatctca<br>gctggctttagcttgtgggtttacaaacaatttgatacttataacctctggaacacttttacaagacttcagagtttagaaaatgtggcttttaatgttgtaaataagggacacttt<br>gatggacaacagggtgaagtaccagtttctatcattaataacactgtttacacaaaagttgatggtgttgatgtagaattgtttgaaaataaaacaacattacctgttaatgtag<br>catttgagctttgggctaagcgcaacattaaaccagtaccagaggtgaaaatactcaataatttgggtgtggacattgctgctaatactgtgatctgggactacaaaagag<br>atgaccagcacatatatctactattggtgtttgttctatgactgacatagccaagaaaccaactgaaacgatttgtgcaccactcactgtattttttgatggtagagttgatggt<br>caagtagacttatttagaaatgcccgtaatggtgttcttattacagaaggtagtgttaaaggtttacaaccatctgtaggtcccaaacaagctagtcttaatggagtcacatta<br>attggagaagccgtaaaaacacagttcaattattataagaaagttgatggtgttgtccaacaattacctgaaacttactttactcagagtagaaatttacaagaatttaaaccc<br>aggagtcaaatggaaattgatttcttagaattagctatggatgaattcattgaacggtataaattagaaggctatgccttcgaacatatcgtttatggagattttagtcatagtc<br>agttaggtggtttacatctactgattggactagctaaacgt-tttaaggaatcaccttttgaattagaagattttattcctatggacagtacagttaaaaactatttcataacagatg<br>cgcaaacaggttcatctaagtgtgtgtgttctgttattgatttattacttgatgattttgttgaaataataaaatcccaagatttatctgtagtttctaaggttgtcaaagtgactatt<br>gactatacagaaatttcatttatgctttggtgtaaagatggccatgtagaaacattttacccaaaattacaatctagtcaagcgtggcaaccgggtgttgctatgcctaatatt<br>acaaaatgcaaagaatgctattagaaaagtgtgaccttcaaaattatggtgatagtgcaacattacctaaaggcataatgatgaatgtcgcaaaatatactcaactgtgtca<br>atatttaaacacattaacattagagtaccctataatatgagagttatacattttggtgctggttctgataaaggagttgcaccaggtacagctgttttaagacagtggttgccta<br>cgggtacgctgcttgtcgattcagatcttaatgactttgtctctgatgcagattcaactttgattggtgattgtgcaactgtacatacagctaataaatgggatctcattattagt<br>gatatgtacgaccctaagactaaaaatgttacaaaagaaaatgactctaaagagggtttttttcacttacatttgtgggtttatacaacaaaagctagctcttggaggttccgtg<br>gctataaagataacagaacattcttggaatgctgatctttataagctcatgggacacttcgcatggtggacagcctttgttactaatgtgaatgcgtcatcatctgaagcatttt<br>taattggatgtaattatcttggcaaaccacgcgaacaaatagatggttatgtcatgcatgcaaattacatattttggaggaatacaaatccaattcagttgtcttcctattattat<br>ttgacatgagtaaatttccccttaaattaaggggtactgctgttatgtattaaaagaaggtcaaatcaatgatatgattttatctcttcttagtaaaggtagacttataattagag<br>aaaacaacagagttgttatttctagtgatgttcttgttaacaactaaacgaacaatgtttgtttttcttgttttattgccactagtctctagtcagtgtgttaatcttacaaccagaac<br>tcaattaccccctgcatacactaattctttcacacgtggtgtttattaccctgacaaagttttcagatcctcagttttacattcaactcaggacttgttcttacctttcttttccaatgt<br>tacttggttccatgctatacatgtctctgggaccaatggtactaagaggtttgataaccagtcctaccatttaatgatggtgtttattttgcttccactgagaagtctaacataat |

TABLE 1-continued

Genome Sequence of SARS-CoV-2

| SEQ ID NO: | Description | Sequence |
|---|---|---|
| | | aagaggctggattttttggtactactttagattcgaagacccagtccctacttattgttaataacgctactaatgttgttattaaagtagtgaatttcaattttgtaatgatccatttttt |
| | | gggtgtttattaccacaaaaacaacaaaagttggatggaaagtgagttcagagtttattctagtgcgaataattgcacttttgaatatgtctctcagccttttcttatggaccttg |
| | | aaggaaaacagggtaatttcaaaaatcttagggaatttgtgtttaagaatattgatggttattttaaaatatattctaagcacacgcctattaatttagtgcgtgatctccctcag |
| | | ggtttttcggctttagaaccattggtagatttgccaataggtattaacatcactaggtttcaaactttacttgctttacatagaagttatttgactcctggtgattcttcttcaggttg |
| | | gacagaggtgctgcagcttattatgtgggttatcttcaacctaggacttttctattaaaatataatgaaaatggaaccattacagatgctgtagactgtgcacttgaccctctc |
| | | tcagaaacaaagtgtacgttgaaatccttcactgtagaaaaaggaatctatcaaacttctaactttagagtccaaccaacagaatctattgttagatttcctaatattacaaact |
| | | tgtgccatttggtgaagtttttaacgccaccagatttgcatctgtttatgcttggaacaggaagagaatcagcaactgtgttgctgattattctgtcctatataattccgcatcat |
| | | tttccacttttaagtgttatggagtgtctcctactaaattaaatgatctctgctttactaatgtctatgcagattcatttgtaattagaggtgatgaagtcagacaaatcgctccag |
| | | ggcaaactggaaagattgctgattataattataaattaccagatgattttacaggctgcgttatagcttggaattctaacaatcttgattctaaggttggtggtaattataattac |
| | | ctgtatagattgtttaggaagtctaatctcaaaccttttgagagagatatttcaactgaaatctatcaggccggtagcacaccttgtaatggtgttgaaggttttaattgttacttt |
| | | cattacaatcatatggtttccaacccactaatggtgttggttaccaaccatacagagtagtagtactttcttttgaacttctacatgcaccagcaactgtttgtggacctaaaaa |
| | | gtctactaatttggttaaaaacaaatgtgtcaatttcaacttcaatggtttaacaggcacaggtgttcttactgagtctaacaaaaagtttctgcctttccaacaatttggcagag |
| | | acattgctgacactactgatgctgtccgtgatccacagacacttgagattcttgacattacaccatgttatttggtggtgtcagtgttataacaccaggaacaaatacttctaa |
| | | ccaggttgctgttctttatcaggatgttaactgcacagaagtccctgttgctattcatgcagatcaacttactcctacttggcgtgtttattctacaggttctaatgtttttcaaaca |
| | | cgtgcaggctgtttaataggggctgaacatgtcaacaactcatatgagtgtgacatacccattggtgcaggtatatgcgctagttatcagactcagactaattctcctcggc |
| | | gggcacgtagtgtagctagtcaatccatcattgcctacactatgtcacttggtgcagaaaattcagttgcttactctaataactctattgccatacccacaaattttactattagt |
| | | gttaccacagaaattctaccagtgtctatgaccaagacatcagtagattgtacaatgtacatttgtggtgattcaactgaatgcagcaatatttgttgcaatatggcagtttttg |
| | | tacacaattaaaccgtgattaactggaatagctgttgaacaagacaaaaacacccaagaagtttttgcacaagtcaaacaaatttacaaaacaccaccaattaaagatttt |
| | | ggtggttttaatttttcacaaatattaccagatccatcaaaaccaagcaagaggtcatttattgaagatctacttttcaacaaagtgacacttgcagatgctggcttcatcaaac |
| | | aatatggtgattgccttggtgatattgctgctagagacctcatttgtgcacaaaagtttaacggccttactgttttgccacctttgctcacagatgaaatgattgctcaatacact |
| | | tctgcactgttagcgggtacaatcacttctggttggacctttggtgcaggtgctgcattacaaataccatttgctatgcaaatggcttataggtttaatggtattggagttacac |
| | | agaatgttactatgagaaccaaaaattgattgccaaccaatttaatagtgctattggcaaaattcaagactcactttcttccacagcaagtgcacttggaaaacttcaagatg |
| | | tggtcaaccaaaatgcacaagctttaaacacgcttgttaaacaacttagctccaattttggtgcaatttcaagtgttttaaatgatatcctttcacgtcttgacaaagttgaggct |
| | | gaagtgcaaattgataggttgatcacaggcagacttcaaagtttgcagacatatgtgactcaacaattaattagagctgcagaaatcagagcttctgctaatcttgctgctac |
| | | taaaatgtcagagtgtgtacttggacaatcaaaaagagttgattttgtggaaagggctatcatcttatgtccttccctcagtcagcacctcatggtgtagtcttcttgcatgtg |
| | | acttatgtccctgcacaagaaaagaacttcacaactgctcctgccatttgtcatgatggaaaagcacactttcctcgtgaaggtgtctttgtttcaaatggcacacactggttt |
| | | gtaacacaaaggaatttttatgaaccacaaatcattactacagacaacacatttgtgtaggtaactgtgatgttgtaataggaattgtcaacaacacagtttatgatcctttgc |
| | | aacctgaattagactcattcaaggaggagttagataaatattttaagaatcatacatcaccagatgttgatttaggtgacatctctggcattaatgcttcagttgtaaacattca |
| | | aaaagaaattgaccgcctcaatgaggttgccaagaatttaaatgaatctctcatcgatctccaagaacttggaaagtatgagcagtatataaaatggccatggtacatttgg |
| | | ctaggttttatagctggcttgattgccatagtaatggtgacaattatgattgctgtatgaccagttgctgtagttgtctcaagggctgttgttcttgtggatcctgctgcaaattt |
| | | gatgaagacgactctgagccagtgctcaaaggagtcaaattacattacacataaacgaacttatggatttgtttatgagaatcttcacaattggaactgtaactttgaagcaa |
| | | ggtgaaatcaaggatgctactccttcagattttgttcgcgctactgcaacgataccgatacaagcctcactccctttcggatggcttattgttggcgttgcacttcttgctgtttt |
| | | tcagagcgcttccaaaatcataaccctcaaaaagagatggcaactagcactctccaagggtgttcactttgtttgcaacttgctgttgttgtttgtaacagtttactcacacctt |
| | | ttgctcgttgctgctggccttgaagccccttttctctatctttatgattagtctacttcttgcagagtataaactttgtaagaataataatgaggctttggctttgctggaaatgcc |
| | | gttccaaaaacccattactttatgatgccaactattttattgctggcatactaattgttacgactattgtataccttacaatagtgtaacttcttcaattgtcattacttcaggtgatg |
| | | gcacaacaagtcctatttctgaacatgactaccagattggtggttatactgaaaaatgggaatctggagtaaaagactgtgttgtattacacagttacttcacttcagactatt |
| | | accagagtactcaactcaattgagtacagacactggtgttgaacatgttaccttcttcatctacaataaaattgttgatgagcctgaagaacatgtccaaattcacacaatcg |
| | | acggttcatccggagttgttaatccagtaatggaaccaatttatgatgaaccgacgacgactactagcgtgcctttgtaagcacaagctgatgagtacgaacttatgtactc |
| | | attcgtttcggaagagacaggtacgttaatagttaatagcgtacttctttttcttgattcgtggtattcttgctagttacactagccatccttactgcgcttcgattgtgtgcgtac |
| | | tgctgcaatattgttaacgtgagtcttgtaaaaccttctttttacgtttactctcgtgttaaaaatctgaattcttctagagttcctgatcttctggtctaaacgaactaaatattatatt |
| | | agtttttctgtttggaactttaattttagccatggcagattccaacggtactattaccgttgaagagcttaaaaagctccttgaacaatggaacctagtaataggtttcctattcct |
| | | tacatggatttgtcttctacaatttgcctatgccaacaggaataggtttttgtatataattaagttaattttcctaggctgttatggccagtaactttagcttgttttgtgcttgctgct |
| | | gtttacagaataaattggatcaccggtggaattgctatcgcaatggcttgtcttgtaggcttgatgtggctcagctacttcattgcttctttcagactgtttgcgcgtacgcgttc |
| | | catgtggtcattcaatccagaaactaacattcttctcaacgtgccactccatggcactattctgaccagaccgcttctagaaagtgaactcgtaatcggagctgtgatccttc |
| | | gtggacatcttcgtattgctggacaccatctaggacgctgtgacatcaaggacctgcctaaagaaatcactgttgctacatcacgaacgctttcttattacaaattgggagct |
| | | tcgcagcgtgtagcaggtgactcaggttttgctgcatacagtcgctacaggattggcaactataaattaaacacagaccattccagtagcagtgacaatattgattgcttgt |
| | | acagtaagtgacaacagatgtttcatctcgttgactttcaggttactatagcagagatattactaattattatgaggacttttaaagtttccatttggaatcttgattacatcataaa |
| | | cctcataattaaaaatttatctaagtcactaactgagaataaatattctcaattagatgaagagcaaccaatggagattgattaaacgaacatgaaaattattattcttggcac |

TABLE 1-continued

| Genome Sequence of SARS-CoV-2 | | |
|---|---|---|
| SEQ ID NO: | Description | Sequence |
| | | tgataacactcgctacttgtgagctttatcactaccaagagtgtgttagaggtacaacagtacttttaaaagaaccttgctcttctggaacatacgagggcaattcaccatttc<br>atcctctagctgataacaaatttgcactgacttgattagcactcaatttgcttttgcttgtcctgacggcgtaaaacacgtctatcagttacgtgccagatcagtttcacctaaa<br>ctgttcatcagacaagaggaagttcaagaactttactaccaatttttcttattgttgcggcaatagtgtttataacactttgcttcacactcaaaagaaagacagaatgattga<br>actttcattaattgacttctatttgtgctttttagcctttagctattccttgttttaattatgcttattatcttttggttctcacttgaactgcaagatcataatgaaacttgtcacgccta<br>aacgaacatgaaatttcttgttttcttaggaatcatcacaactgtagctgcatttcaccaagaatgtagtttacagtcatgtactcaacatcaaccatatgtagttgatgacccgt<br>gtcctattcacttctattctaaatggtatattagagtaggagctagaaaatcagcacctttaattgaattgtgcgtggatgaggctggttctaaatcacccattcagtacatcga<br>tatcggtaattatacagtttcctgtttaccttttacaattaattgccaggaacctaaattgggtagtcttgtagtgcgttgttcgttctatgaagactttttagagtatcatgacgttc<br>gtgttgttttagatttcatctaaacgaacaaactaaaatgtctgataatggaccccaaaatcagcgaaatgcaccccgcattacgtttggtggaccctcagattcaactggca<br>gtaaccagaatggagaacgcagtggggcgcgatcaaaacaacgtcggccccaaggtttacccaataatactgcgtcttggttcaccgctctcactcaacatggcaagg<br>aagaccttaaattccctcgaggacaaggcgttccaattaacaccaatagcagtccagatgaccaaattggctactaccgaagagctaccagacgaattcgtggtggtga<br>cggtaaaatgaaagatctcagtccaagatggtatttctactacctaggaactgggccagaagctggacttccctatggtgctaacaaagacggcatcatatgggttgcaa<br>ctgagggagccttgaatacaccaaaagatcacattggcacccgcaatcctgctaacaatgctgcaatcgtgctacaacttcctcaaggaacaacattgccaaaaggcttc<br>tacgcagaagggagcagaggcggcagtcaagcctcttctcgttcctcatcacgtagtcgcaacagttcaagaaattcaactccaggcagcagtaggggaacttctcctg<br>ctagaatggctggcaatggcggtgatgctgctcttgctttgctgctgcttgacagattgaaccagcttgagagcaaaatgtctggtaaaggccaacaacaacaaggccaa<br>actgtcactaagaaatctgctgctgaggcttctaagaagcctcggcaaaaacgtactgccactaaagcatacaatgtaacacaagctttcggcagacgtggtccagaac<br>aaacccaaggaaattttggggaccaggaactaatcagacaaggaactgattacaaacattggccgcaaattgcacaatttgcccccagcgcttcagcgttcttcggaatg<br>tcgcgcattggcatggaagtcacaccttcgggaacgtggttgacctacacaggtgccatcaaattggatgacaaagatccaaatttcaaagatcaagtcattttgctgaat<br>aagcatattgacgcatacaaaacattcccaccaacagagcctaaaaaggacaaaaagaagaaggctgatgaaactcaagccttaccgcagagacagaagaaacagc<br>aaactgtgactcttcttcctgctgcagatttggatgatttctccaaacaattgcaacaatccatgagcagtgctgactcaactcaggcctaaactcatgcagaccacacaag<br>gcagatgggctatataaacgttttcgcttttccgtttacgatatatagtctactcttgtgcagaatgaattctcgtaactacatagcacaagtagatgtagttaactttaatctcac<br>atagcaatattaatcagtgtgtaacattagggaggacttgaaagagccaccacattttcaccgaggccacgcggagtacgatcgagtgtacagtgaacaatgctaggg<br>agagctgcctatatggaagagccctaatgtgtaaaattaattttagtagtgctatccccatgtgattttaatagcttcttaggagaatgacaaaaaaaaaaaaaaaaaaaaa<br>aaaaaaaaaaa |

EXAMPLES

Example 1—Manufacturing of Vaccine Particles for COVID-19

In various embodiments of the disclosed particles could be used to treat or prevent any infectious disease caused by a virus, bacteria, or other pathogenic microbe. Indeed, the flexibility of the disclosed nucleic acid vaccine platform sets the disclosed particles apart from previous nucleic acid-based vaccines. The present example relates specifically to the preparation of a COVID-19 vaccine, but those of skill in the art will understand that the following manufacturing techniques could be applied to any other virus, bacteria, or pathogenic microbe for which a vaccine is desired.

With all inputs readily available, a COVID-19 YCWP vaccine takes only hours to manufacture and can be manufactured on a large scale with ease. The manufacturing of the vaccine can be divided into three phases: (1) making of the YCWPs (see FIG. 1); (2) treating the YCWPs with polyethylenimine (PEI) (see FIG. 2); and (3) loading the surface of the YCWPs with COVID-19 plasmid and flu virus vaccine for the final product formulation (see FIG. 3).

Manufacturing YCWP

Yeast cell wall particles (YCWP) were made from Fleishmans Baker's yeast through a series of steps.

The contents of the yeast were dissolved in 1M NaOH, the resulting undissolved yeast cell walls were recovered and washed extensively in water, isopropanol, acetone, and finally freeze dried in 1×PBS.

YCWP were prepared by suspending *Saccharomyces cerevisiae* (100 g of Fleishmans Baker's yeast, AB Mauri Food Inc., Chesterfield, Mo.) in 1 L of 1 M NaOH and heating to 90° C. for one hour. The insoluble material containing the yeast cell walls was collected by centrifugation at 2000×g for 10 minutes. This insoluble material was then suspended in 1 L of water, brought to pH 4-5 with HCl, then incubated at 75° C. for one hour. The insoluble residue was again collected by centrifugation and washed once with 1 L of water, four times with 200 mL of isopropanol, and twice with 200 mL of acetone. The resulting slurry was dried at room temperature in a sterile hood to produce 12.4 g of a fine, slightly off-white powder.

The powder composed of dry YCWP was carefully weighed and suspended in sterile distilled water at a concentration of 10 mg/ml, and 1 ml aliquots were placed in sterile Eppendorf tubes, frozen at −60° C., and freeze-dried at 0.012 mBar. Because the boiling point of isopropanol and acetone is considerably below that of water, any possible contamination by these solvents was removed under these high vacuum conditions and physically assured by the loss of water.

Furthermore, each batch of YCWP is tested to assure their non-viability by seeding an aliquot onto agar plates containing CMC Yeast growth media (Invitrogen, Inc.) and the batch is only be released for use in vaccine manufacture if no yeast colonies appear after one full week of incubation.

The prepared YCWP will be placed in CMC yeast growth media (Invitrogen, Inc.) and monitored for growth over 7 days. All prior testing has never shown any viable and proliferating yeast after the extensive YCWP production procedures outlined above. Un-manipulated *Saccharomyces cerevisiae* is used as a parallel positive control.

Treating YCWPs with PEI

YCWPs were oxidized with sodium periodate. Next, the YCWPs were reacted with streptavidin by reductive amination in the presences of sodium cyanoborohydride to equal 1 mg streptavidin/10 mg YCWP.

50 μg of 25 kd PEI-g-PEG-Biotin was used to coat 10 mg of streptavidin modified particles with PEI.

Loading the Surface of the YCWPs with COVID-19 Plasmid and Flu Virus 10 mg of PEI coated YCWPs were mixed with 20 μg of the plasmid pRFP-C-RS shRNA in PBS for 30 minutes at 15° C. to 25° C. Next recombinant GFP adenoviral particles were added in PBS and incubated at 15° C. to 25° C. for 30 minutes. Single use aliquots were then set aside.

Purification of Flu Vaccine Virus Particles

Flu vaccine was as a source of adenovirus particles. Flu vaccine virus particles were purified with a PUREVIRUS™ Adenovirus Purification Kit from Cell Biolab and concentrated with Amicon Centrifugal Filter Units with a 100 kd molecular cutoff.

Toxicology

No adverse effects of the COVID-19 YCWP-DNA vaccine are expected since trials using a similar particle technology have shown remarkable safety in prior clinical trials in melanoma patients. The reason for such a safety profile lies in the fact that these particles are specifically and selectively taken up by antigen presenting cells (APCs) and do not expose other cells nor accessory tissues to their composition, and any adjuvant effects of the beta glucan composition of the YCWPs is selectively experienced only by these APCs, which are terminally differentiated cells. This cell specific adjuvant effect is unique to the YCWP technology.

Sterility Testing

In-process sterility testing and final product sterility testing are assessed by different methods. The in-process sterility testing, can be performed in-house and assesses aerobic and anaerobic microbial contamination. The results for in-process are available after a five-day incubation period.

The final product sterility testing is performed according to the USP<71>direct inoculation sterility test method including a 14 day incubation is performed at a contract testing laboratory approved by the agency. In-process sterility testing is used to assess all steps of the manufacturing process to screen for and isolate any contamination. However, all final product sterility test results will be available before lot release and shipping.

Endotoxin Testing

Endotoxin testing is performed on the final product. It has been shown that YCWP will cause low-level positive endotoxin test results; therefore, the limits have been increased to accommodate these low level false positives.

Additionally, sterile empty YCWP are run as a negative control in all assays. Only results that are 20% above the negative control will be considered positive. The increased upper limit for the endotoxin assay readout is not meant to permit a higher endotoxin level in the final product, which is well below the 5 EU/kg body weight limit. Instead, the increased limit is to account for a known and well-established low level false positive result with this assay due to the beta glucan in the denuded yeast cell wall. Therefore, empty, un-manipulated and sterile YCWP are used as a control for the endotoxin assay to set an appropriate release limit for the final vaccine.

Example 2—Efficient and Effective Delivery of DNA by YCWPs into APCs in Culture Recombinant adenovirus encoding the GFP gene was constructed with the VIRAPOWER™ Adenoviral Gateway™ Expression system. The GFP gene sequence was cloned into the destination vector pAd/CMV/V5-DEST under the control of a CMV promoter as shown in the vector map shown in FIG. 4.

This genetic construction was transfected into 293A cells for recombinant adenovirus packaging. Recombinant adenoviral particles were purified with a PUREVIRUS™ Adenovirus Purification Kit from Cell Biolab and concentrated with Amicon Centrifugal Filter Units with a 100 kd molecular cutoff.

Plasmid DNA of the pRFP-C-RS shRNA plasmid (cat #TR30014) from Origen, as shown in the plasmid map in FIG. 5 was prepared by standard procedures. This plasmid was constructed such that the turbo RFP (red fluorescence protein) gene is driven by a CMV promoter.

YCWPs were modified to contain a highly positively charged external surface by reaction with polyethyleneimine (PEI). First YCWPs were surface modified with streptavidin. Briefly, YCWPs were first oxidized with sodium periodate and then the resulting surface aldehyde groups were reacted with streptavidin (Promega) by reductive amination in the presence of sodium cyanoborohydride. The resulting modified YCWPs contained about 1 mg streptavidin/10 mg YCWP ($1.51 \times 10^{-8}$ mole streptavidin/10 mg particle, about $3.64 \times 10^{16}$ biotin binding sites). 50 µg of 25 kd PEI-g-PEG-Biotin (2 nM, about $1.2 \times 10^{15}$ molecules; shown in Formula I below) from Nanosoft polymers was used to coat 10 mg of streptavidin modified particles with PEI, which is about $1.5 \times 10^6$ PEI molecules/particle.

Formula I 10 mg of PEI coated particles were mixed with 20 µg of the plasmid pRFP-C-RS shRNA in PBS for 30 minutes at 15° C. to 25° C. to form the DNA/PEI complex on the surface of the particle. This gives a N/P ratio around 20. After the PEI/DNA complex was formed, $4 \times 10^{11}$ or $8 \times 10^{11}$ recombinant GFP adenoviral particles in PBS were added into the mixture and incubated for another 30 minutes at 15° C. to 25° C. This is equivalent to about 500 to 1000 viruses per YCWP.

For cell transfection, mouse RAW 264.7 cells and human THP-1 cells were used. The plasmid DNA/Ad5 virus/YCWPs were added to these cultures at a ratio of about 2 particles per cell. Red and green fluorescence were observed 24 hours after transfection by fluorescence microscopy. Cells fluorescing green show the presence of functioning Ad5 GFP indicating effective escape and phagosome release of the bound viruses, while red fluorescing cells show the presence and functionality of the plasmid DNA attached to the YCWPs. FIG. 6 shows representative images of fluorescing cells.

Example 3—Efficient and Effective Delivery of a COVID-19 Surface Glycoprotein S Encoding Plasmid into APCs in Culture Via an Ad5/RFP-COVID-19-GFP Plasmid/-YCWP The basic procedure for the formation of this particulate vector was the same as that described above for the vector described above. Ad5/RFP (Ad-RFP), the virus used in this particle vector, was from Vector biolab and is a recombinant human type 5 adenovirus expressing Red Fluorescent Protein (RFP) under the control of a CMV promoter. The plasmid, 2019-nCov_pcDNA3.1(+)-P2A-eGFP, is from Genscript. The COVID-19 surface glycoprotein is under the control of a CMV promoter with the GFP gene sequence fused in frame via P2A sequence for tracking. A map of the plasmid encoding a COVID-19 surface glycoprotein S is shown in FIG. 7.

Figure 8:
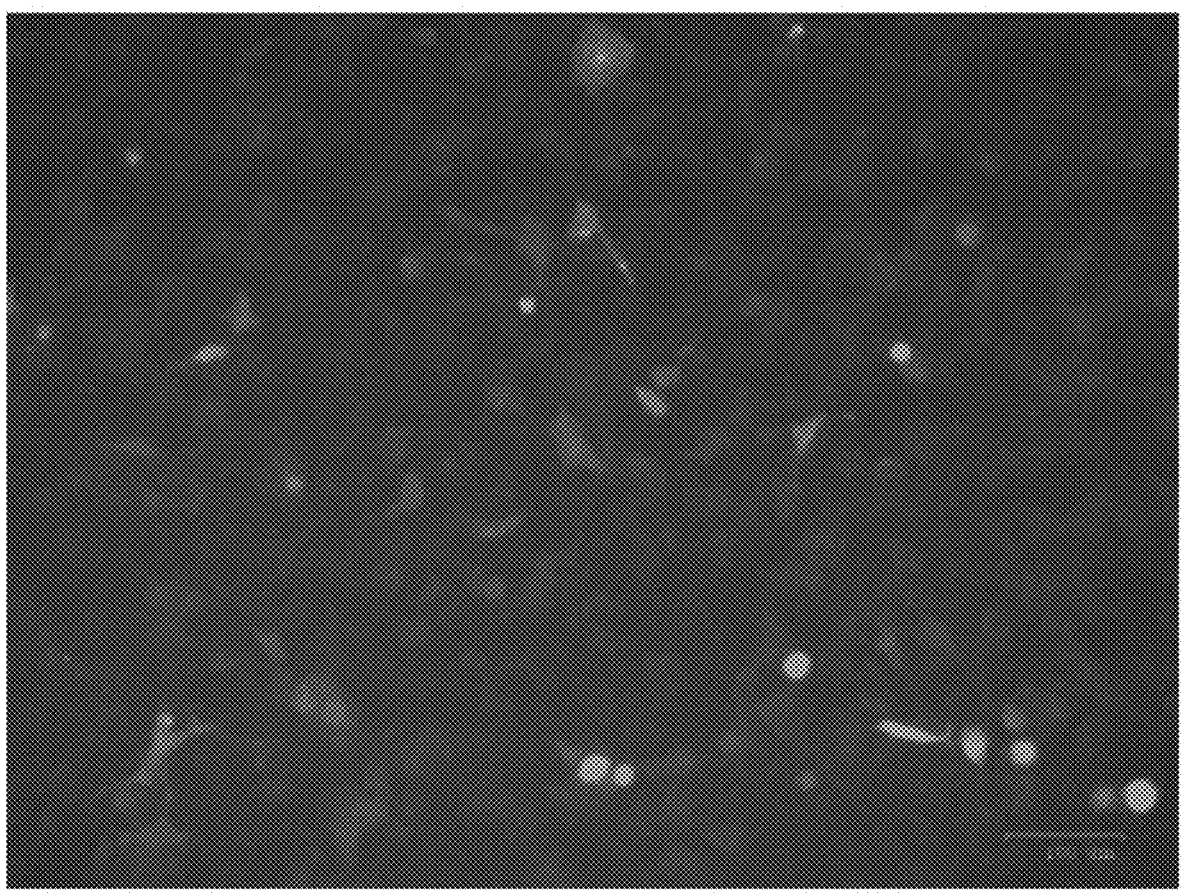
FIG. 8 shows mouse RAW 264.7 cells that were transfected with Ad5/RFP-COVID-19-GFP plasmid/-YCWPs and expressing COVID-19 S protein.

Mouse RAW 264.7 cells were transfected with Ad5/RFP-COVID-19-GFP plasmid/-YCWPs. The green color shows the expression of not only the green fluorescent protein but also the COVID-19 S protein, since both proteins are driven off the same promoter. The percentage of cells showing green fluorescence reflects the COVID-19 S protein transfection efficiency, as exemplified by FIG. 8.

Example 4—In Vitro Testing of DNA-YCWP Vaccines 10 mg of streptavidin modified yeast particles were mixed with 2 µl of protein A/G biotin (1 mg/ml)(MBL: JM-6508-1), 2 µl of adenovirus type 5 Hexon antibody (4 mg/ml) (Invitrogen: PA1-28357) and 100 µg of Biotin-PEI (branched 25 KD) (Nanosoft polymers: 12674-25k-1000-10). The mixture was rotated at RT for two hours.

The mixture was washed 3× with PBS by centrifugation at 500×g for 5 minutes and resuspended in 1 ml PBS (gently sonicate if aggregates appear). About $10^{12}$ viral particles were added to the mixture and rotated for another 2 hours. The viral particles included the commercially available Seqirus quadrivalent vaccine, which was attached to the YCWP via the anti-hexon antibody. The results showed that the Seqirus quadrivalent vaccine, which is a flu vaccine made of enfeebled virus particles, was equally as effective as a research adenovirus.

At the end of incubation, 100 µl of the mixture (1 mg particles equivalent to about 20 PEI) were mixed with different amount of plasmid DNA (5, 10, 15, 20, 25 µg) and incubated for 30 minutes. 10 µl of the mixture were used for transfection of a well in a 12-well plate.

FIG. 9 shows that the transfection was successful, with >99% of cells contacted with the vaccine.

Example 5—Vaccination of Mice with YCWPs Containing Attached Ad5GFP Virus and a COVID-19 Surface Glycoprotein S Encoding DNA Plasmid C57B mice were divided into four treatment groups:
1. DNA-YCWP vaccine comprising (i) a commercially available Seqirus quadrivalent influenza vaccine as the lysosome-evading component, and (ii) a plasmid encoding SARS-CoV-2 glycoprotein S (i.e., spike protein);
2. DNA-YCWP vaccine comprising (i) a non-infectious adenovirus as the lysosome-evading component, and (ii) a plasmid encoding SARS-CoV-2 glycoprotein S (i.e., spike protein);

3. Protein-YCWP vaccine comprising (i) a non-infectious adenovirus as the lysosome-evading component, and (ii) a SARS-CoV-2 glycoprotein S (i.e., spike protein) loaded within the YCWP; and
4. A control group.

Four mice were included within each treatment group. The mice received intradermal vaccinations of $10^6$ vaccine particles suspended in PBS near an inguinal lymph node.

The mice were bled one week after administration, and serum was isolated. The serum was assess for the presence of anti-glycoprotein S antibodies using an enzyme-linked immunosorbent assay (ELISA). More specifically, ELISA plates were coated with recombinant surface glycoprotein (S protein) of COVID-19 at a concentration of 0.4 μg/ml in PBS at 4° C. overnight. Plates were washed and blocked with PBS containing 0.05% Tween 20, 0.5% of BSA for 1 h at 37° C. Diluted serum samples were then added and incubated at 4° C. overnight. After washing, goat anti-mouse immunoglobulins conjugated to HRP (1:1000) were added, and plates were incubated for one hour at 37° C. Finally, plates were washed and developed with 3,3',5,5'-tetramethylbenzidine. The reaction was stopped by adding 50 μl of 2.5M H2504 and the OD450 nm was measured. Cutoff values were determined as average OD450 of sera from mice immunized without plasmid DNA at dilutions 100 to 200 plus 3 STDV. End-point titer was as the dilution at which OD450 of the serum sample falls below the cut-off.

For each treatment group receiving a vaccine, antibodies were detected in the serum up to a dilution of 1:200. Moreover, antibodies were detected in a comparable amount in both the DNA vaccines and the protein vaccine. This result was, in and of itself, remarkable, as protein vaccines generally elicit a more robust immune response than DNA vaccines. Moreover, the fragment of the glycoprotein S that was encoded by the plasmid is the portion of the protein that binds to the receptor on the cells it infects, which suggests that the antibodies elicited by the vaccine are likely to be neutralizing antibodies.

Example 6—Determination of Specific Cellular Immune Responses in Mice Vaccinated with YCWPs Containing Attached Ad5GFP Virus and a COVID-19 Surface Glycoprotein S Encoding DNA Plasmid ELISPOT assays will be used for monitoring specific cellular immune responses:

Mice will be sacrificed 21 days post prime, or 14 days post boost immunization. Spleen cells will be collected, and cellular immune responses will be measured by single or Dual-color ELISPOT kits from R&D System. The following kits will be used:

1. Mouse IFN-gamma ELISpot Kit (cat #: EL485); Mouse Granzyme B ELISpot Kit (cat #: EL1865);
2. Mouse TNF-alpha ELISpot Kit (cat #: EL410); Mouse IFN-gamma/Granzyme B Dual-Color ELISpot Kit (cat #: ELD5819); and
3. Mouse IFN-gamma/IL-2 Dual-Color ELISpot Kit (cat #: ELD5006).

Briefly, a total of $2.5\times10^5$ splenocytes per well will be plated and stimulated for 20 h with recombinant COVID-19 S protein at a concentration of 10 μg/ml. The costimulatory anti-CD28 antibody will also be added to the cells during the incubation to stimulate production of IL-2 to synchronize it with secretion of INF-α. The plates will be processed according to manufacturer's protocol. If necessary, intracellular IFN-gamma staining can be performed by flow cytometric analysis, which can be combined with CD4 and CD8 surface maker staining to further analyze the percentages of CD4 and CD8 population.

Example 7—Polylysine/Adenovirus/Covid-19 S Gene Plasmid Transfection of Mouse Raw 264.7 Cells Around $5\times10^{11}$ adenovirus particles (Ad5/LacZ) were linked to 100 μg of polylysine polymer by transglutaminase in 1 ml of buffer at 37° C. for 1.5 hours. After buffer exchange, about 1.5 μg of polylysine/adenovirus complex was mixed with 10 μg of plasmid DNA and incubate at room temperature for 30 minutes in rotation in a 100/100 volume. The plasmid DNA encoded both green fluorescent protein (GFP) and SARS-CoV-2 S protein (i.e., spike protein).

Following incubation of the polylysine/adenovirus complex with the DNA, 10 μl of the vaccine composed of polylysine-decorated adenovirus bound by plasmid DNA was added into a well of a 12 well plate with RAW cells.

FIG. 11 shows that the transfection was successful, with >99% of cells contacted with the vaccine.

One skilled in the art readily appreciates that the present disclosure is well adapted to carry out the objects and obtain the ends and advantages mentioned, as well as those inherent therein. Modifications therein and other uses will occur to those skilled in the art. These modifications are encompassed within the spirit of the disclosure and are defined by the scope of the claims, which set forth non-limiting embodiments of the disclosure.

What is claimed:

1. A SARS-CoV-2 vaccine comprising: (i) a yeast cell wall particle (YCWP) that is surface-modified with polyethyleneimine (PEI), (ii) a lysosome-evading component attached to the YCWP, and (iii) a deoxyribonucleic acid (DNA) sequence encoding a viral spike protein of SARS-CoV-2 or an immunogenic fragment thereof, wherein the nucleic acid is attached to the YCWP via a complex formed between the PEI and the nucleic acid, wherein intradermal administration of the SARS-CoV-2 vaccine to a human subject elicits an immunogenic response.

2. The SARS-CoV-2 vaccine of claim 1, wherein the lysosome-evading component is a non-infectious virus.

3. The SARS-CoV-2 vaccine of claim 2, wherein the non-infectious virus is an adenovirus.

4. The SARS-CoV-2 vaccine of claim 1, wherein the lysosome-evading component is a quadrivalent influenza vaccine.

5. The SARS-CoV-2 vaccine of claim 1, wherein the lysosome-evading component is a protein.

6. The SARS-CoV-2 vaccine of claim 5, wherein the protein is a hexon protein, a penton protein, melittin, or LL37.

7. The SARS-CoV-2 vaccine of claim 1, wherein the nucleic acid encoding the viral spike protein of SARS-CoV-2 or an immunogenic fragment thereof is comprised within an expression vector or plasmid.

8. The SARS-CoV-2 vaccine of claim 1, wherein the viral spike protein of SARS-CoV-2 comprises SEQ ID NO: 1 or an immunogenic fragment thereof.

9. The SARS-CoV-2 vaccine of claim 1, wherein the lysosome-evading component is attached to the YCWP by an antibody.

10. The SARS-CoV-2 vaccine of claim 1, wherein the YCWP further surface modified with succinimidyl 3-(2-pyridyldithio)propionate (SPDP).

11. The SARS-CoV-2 vaccine of claim 10, wherein melittin or LL37 are crosslinked to the YCWP by the SPDP.

12. A vaccine comprising: (i) yeast cell wall particle (YCWP) that is surface modified with polyethyleneimine (PEI), (ii) an adenovirus attached to the YCWP, and (iii) a deoxyribonucleic acid (DNA) sequence encoding a SARS-CoV-2 viral spike protein or an immunogenic fragment thereof, wherein the adenovirus and the nucleic acid is attached to the YCWP by forming a complex with the PEI, wherein intradermal administration of the vaccine to a human subject elicits an immunogenic response.

13. The vaccine of claim 12, wherein the adenovirus is attached to the YCWP indirectly via an anti-hexon protein antibody.

14. The vaccine of claim 12, wherein the adenovirus is non-infectious and non-replicative.

15. The vaccine of claim 12, wherein the viral spike protein comprises SEQ ID NO: 1.

16. A method of reducing a risk of infection from coronavirus disease 2019 (COVID-19) in a human subject comprising, administering to the human subject a vaccine comprising: (i) yeast cell wall particle (YCWP) that is surface modified with polyethyleneimine (PEI), (ii) a non-infectious and non-replicative adenovirus attached to the YCWP, and (iii) a deoxyribonucleic acid (DNA) sequence encoding a viral spike protein from SARS-CoV-2 or an immunogenic fragment thereof.

17. The method of claim 16, wherein the adenovirus is attached to the YCWP indirectly via an anti-hexon protein antibody.

18. The method of claim 16, wherein the viral spike protein comprises SEQ ID NO: 1.

19. The method of claim 16, wherein the vaccine is administered intradermally.

* * * * *

SEQUENCE LISTING

```
<160> NUMBER OF SEQ ID NOS: 5

<210> SEQ ID NO 1
<211> LENGTH: 1273
<212> TYPE: PRT
<213> ORGANISM: Severe acute respiratory syndrome coronavirus 2

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
```

```
                35                  40                  45
His Ser Thr Gln Asp Leu Phe Leu Pro Phe Phe Ser Asn Val Thr Trp
 50                  55                  60

Phe His Ala Ile His Val Ser Gly Thr Asn Gly Thr Lys Arg Phe Asp
 65                  70                  75                  80

Asn Pro Val Leu Pro Phe Asn Asp Gly Val Tyr Phe Ala Ser Thr Glu
                 85                  90                  95

Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
                115                 120                 125

Lys Val Cys Glu Phe Gln Phe Cys Asn Asp Pro Phe Leu Gly Val Tyr
130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
                180                 185                 190

Val Phe Lys Asn Ile Asp Gly Tyr Phe Lys Ile Tyr Ser Lys His Thr
                195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Tyr Tyr Val Gly Tyr Leu Gln Pro
                260                 265                 270

Arg Thr Phe Leu Leu Lys Tyr Asn Glu Asn Gly Thr Ile Thr Asp Ala
                275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
                355                 360                 365

Tyr Asn Ser Ala Ser Phe Ser Thr Phe Lys Cys Tyr Gly Val Ser Pro
                370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Phe Thr Gly Cys
                420                 425                 430

Val Ile Ala Trp Asn Ser Asn Asn Leu Asp Ser Lys Val Gly Gly Asn
                435                 440                 445

Tyr Asn Tyr Leu Tyr Arg Leu Phe Arg Lys Ser Asn Leu Lys Pro Phe
450                 455                 460
```

```
Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
        690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880
```

```
Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
        980                 985                 990

Ile Asp Arg Leu Ile Thr Gly Arg Leu Gln Ser Leu Gln Thr Tyr Val
    995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270
```

```
<210> SEQ ID NO 2
<211> LENGTH: 29903
<212> TYPE: DNA
<213> ORGANISM: Severe acute respiratory syndrome coronavirus 2

<400> SEQUENCE: 2
attaaaggtt tataccttcc caggtaacaa accaaccaac tttcgatctc ttgtagatct     60
gttctctaaa cgaactttaa aatctgtgtg gctgtcactc ggctgcatgc ttagtgcact    120
cacgcagtat aattaataac taattactgt cgttgacagg acacgagtaa ctcgtctatc    180
ttctgcaggc tgcttacggt ttcgtccgtg ttgcagccga tcatcagcac atctaggttt    240
cgtccgggtg tgaccgaaag gtaagatgga gagccttgtc cctggtttca acgagaaaac    300
acacgtccaa ctcagtttgc ctgttttaca ggttcgcgac gtgctcgtac gtggctttgg    360
agactccgtg gaggaggtct tatcagaggc acgtcaacat cttaaagatg gcacttgtgg    420
cttagtagaa gttgaaaaag gcgttttgcc tcaacttgaa cagccctatg tgttcatcaa    480
acgttcggat gctcgaactg cacctcatgg tcatgttatg gttgagctgg tagcagaact    540
cgaaggcatt cagtacggtc gtagtggtga cacttggt gtccttgtcc ctcatgtggg    600
cgaaatacca gtggcttacc gcaaggttct tcttcgtaag aacggtaata aaggagctgg    660
tggccatagt tacggcgccg atctaaagtc atttgactta ggcgacgagc ttggcactga    720
tccttatgaa gattttcaag aaaactggaa cactaaacat agcagtggtg ttacccgtga    780
actcatgcgt gagcttaacg gaggggcata cactcgctat gtcgataaca cttctgtgg    840 ccctgatggc taccctcttg agtgcattaa agaccttcta gcacgtgctg gtaaagcttc    900
atgcactttg tccgaacaac tggactttat tgacactaag agggtgtat actgctgccg    960 tgaacatgag catgaaattg cttggtacac ggaacgttct gaaaagagct atgaattgca   1020
gacacctttt gaaattaaat tggcaaagaa atttgacacc ttcaatgggg aatgtccaaa   1080
ttttgtattt ccccttaaatt ccataatcaa gactattcaa ccaagggttg aaaagaaaaa   1140
gcttgatggc tttatgggta gaattcgatc tgtctatcca gttgcgtcac caaatgaatg   1200
caaccaaatg tgccttttcaa ctctcatgaa gtgtgatcat tgtggtgaaa cttcatggca   1260
gacgggcgat tttgttaaag ccacttgcga attttgtggc actgagaatt tgactaaaga   1320
aggtgccact acttgtggtt acttacccca aaatgctgtt gttaaaattt attgtccagc   1380
atgtcacaat tcagaagtag gacctgagca tagtcttgcc gaataccata tgaatctgg   1440 cttgaaaacc attcttcgta agggtggtcg cactattgcc tttggaggct gtgtgttctc   1500
ttatgttggt tgccataaca gtgtgcctta ttgggttcca cgtgctagcg ctaacatagg   1560
ttgtaaccat acaggtgttg ttggagaagg ttccgaaggt cttaatgaca accttcttga   1620
aatactccaa aaagagaaag tcaacatcaa tattgttggt gactttaaac ttaatgaaga   1680
gatcgccatt atttttggcat ctttttctgc ttccacaagt gcttttgtgg aaactgtgaa   1740
aggtttggat tataaagcat tcaaacaaat tgttgaatcc tgtggtaatt ttaaagttac   1800
aaaaggaaaa gctaaaaaag gtgcctggaa tattggtgaa cagaaatcaa tactgagtcc   1860
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
```

-continued

```
agagaagttt aaggaaggtg tagagtttct tagagacggt tgggaaattg ttaaatttat    2220
ctcaacctgt gcttgtgaaa ttgtcggtgg acaaattgtc acctgtgcaa aggaaattaa    2280
ggagagtgtt cagacattct ttaagcttgt aaataaattt ttggctttgt gtgctgactc    2340
tatcattatt ggtggagcta aacttaaagc cttgaatta ggtgaaacat ttgtcacgca    2400
ctcaaaggga ttgtacagaa agtgtgttaa atccagagaa gaaactggcc tactcatgcc    2460
tctaaaagcc ccaaaagaaa ttatcttctt agagggagaa acacttccca cagaagtgtt    2520
aacagaggaa gttgtcttga aaactggtga tttacaacca ttagaacaac ctactagtga    2580
agctgttgaa gctccattgg ttggtacacc agtttgtatt aacgggctta tgttgctcga    2640
aatcaaagac acagaaaagt actgtgccct tgcacctaat atgatggtaa caaacaatac    2700
cttcacactc aaaggcggtg caccaacaaa ggttactttt ggtgatgaca ctgtgataga    2760
agtgcaaggt tacaagagtg tgaatatcac ttttgaactt gatgaaagga ttgataaagt    2820
acttaatgag aagtgctctg cctatacagt tgaactcggt acagaagtaa atgagttcgc    2880
ctgtgttgtg gcagatgctg tcataaaaac tttgcaacca gtatctgaat tacttacacc    2940
actgggcatt gatttagatg agtggagtat ggctacatac tacttatttg atgagtctgg    3000
tgagtttaaa ttggcttcac atatgtattg ttctttctac cctccagatg aggatgaaga    3060
agaaggtgat tgtgaagaag aagagtttga gccatcaact caatatgagt atggtactga    3120
agatgattac caaggtaaac ctttggaatt tggtgccact tctgctgctc ttcaacctga    3180
agaagagcaa gaagaagatt ggttagatga tgatagtcaa caaactgttg gtcaacaaga    3240
cggcagtgag gacaatcaga caactactat tcaaacaatt gttgaggttc aacctcaatt    3300
agagatggaa cttacaccag ttgttcagac tattgaagtg aatagtttta gtggttattt    3360
aaaacttact gacaatgtat acattaaaaa tgcagacatt gtggaagaag ctaaaaaggt    3420
aaaaccaaca gtggttgtta atgcagccaa tgtttacctt aaacatggag gaggtgttgc    3480
aggagcctta aataaggcta ctaacaatgc catgcaagtt gaatctgatg attacatagc    3540
tactaatgga ccacttaaag tgggtggtag ttgtgtttta agcggacaca atcttgctaa    3600
acactgtctt catgttgtcg gcccaaatgt taacaaaggt gaagacattc aacttcttaa    3660
gagtgcttat gaaaatttta atcagcacga agttctactt gcaccattat tatcagctgg    3720
tattttggt gctgacccta tacattcttt aagagtttgt gtagatactg ttcgcacaaa    3780
tgtctactta gctgtctttg ataaaaatct ctatgacaaa cttgtttcaa gcttttggga    3840
aatgaagagt gaaaagcaag ttgaacaaaa gatcgctgag attcctaaag aggaagttaa    3900
gccatttata actgaaagta aaccttcagt tgaacagaga aaacaagatg ataagaaaat    3960
caaagcttgt gttgaagaag ttacaacaac tctggaagaa actaagttcc tcacagaaaa    4020
cttgttactt tatattgaca ttaatggcaa tcttcatcca gattctgcca ctcttgttag    4080
tgacattgac atcactttct taagaagaga tgctccatat atagtgggtg atgttgttca    4140
agagggtgtt ttaactgctg tggttatacc tactaaaaag gctggtggca ctactgaaat    4200
gctagcgaaa gctttgagaa aagtgccaac agacaattat ataaccactt acccgggtca    4260
gggtttaaat ggttacactg tagaggaggc aaagacagtg cttaaaaagt gtaaaagtgc    4320
cttttacatt ctaccatcta ttatctctaa tgagaagcaa gaaattcttg gaactgtttc    4380
ttggaatttg cgagaaatgc ttgcacatgc agaagaaaca cgcaaattaa tgcctgtctg    4440
tgtggaaact aaagccatag tttcaactat acagcgtaaa tataagggta ttaaaataca    4500
agagggtgtg gttgattatg gtgctagatt ttacttttac accagtaaaa caactgtagc    4560
```

-continued

```
gtcacttatc aacacactta acgatctaaa tgaaactctt gttacaatgc cacttggcta    4620
tgtaacacat ggcttaaatt tggaagaagc tgctcggtat atgagatctc tcaaagtgcc    4680
agctacagtt tctgtttctt cacctgatgc tgttacagcg tataatggtt atcttacttc    4740
ttcttctaaa acacctgaag aacatttat tgaaccatc tcacttgctg gttcctataa    4800
agattggtcc tattctggac aatctacaca actaggtata gaatttctta agagaggtga    4860
taaaagtgta tattcacta gtaatcctac cacattccac ctagatggtg aagttatcac    4920
ctttgacaat cttaagacac ttctttcttt gagagaagtg aggactatta aggtgtttac    4980
aacagtagac aacattaacc tccacacgca agttgtggac atgtcaatga catatggaca    5040
acagtttggt ccaacttatt tggatggagc tgatgttact aaaataaaac ctcataattc    5100
acatgaaggt aaaacatttt atgttttacc taatgatgac actctacgtg ttgaggcttt    5160
tgagtactac cacacaactg atcctagttt tctgggtagg tacatgtcag cattaaatca    5220
cactaaaaag tggaaatacc cacaagttaa tggtttaact tctattaaat gggcagataa    5280
caactgttat cttgccactg cattgttaac actccaacaa atagagttga agtttaatcc    5340
acctgctcta caagatgctt attacagagc aagggctggt gaagctgcta acttttgtgc    5400
acttatctta gcctactgta ataagacagt aggtgagtta ggtgatgtta gagaaacaat    5460
gagttacttg tttcaacatg ccaatttaga ttccttgcaaa agagtcttga acgtggtgtg    5520
taaaacttgt ggacaacagc agacaaccct taagggtgta gaagctgtta tgtacatggg    5580
cacactttct tatgaacaat ttaagaaagg tgttcagata ccttgtacgt gtggtaaaca    5640
agctacaaaa tatctagtac aacaggagtc accttttgtt atgatgtcag caccacctgc    5700
tcagtatgaa cttaagcatg gtacatttac ttgtgctagt gagtcacactg gtaattacca    5760 gtgtggtcac tataaacata taacttctaa agaaactttg tattgcatag acggtgcttt    5820
acttacaaag tcctcagaat acaaaggtcc tattacggat gttttctaca agaaaacag    5880 ttacacaaca accataaaac cagttactta taaattggat ggtgttgttt gtacagaaat    5940
tgaccctaag ttggacaatt attataagaa agacaattct tatttcacag agcaaccaat    6000
tgatcttgta ccaaaccaac catatccaaa cgcaagcttc gataatttta agtttgtatg    6060
tgataatatc aaatttgctg atgatttaaa ccagttaact ggttataaga aacctgcttc    6120
aagagagctt aaagttacat ttttccctga cttaaatggt gatgtggtgg ctattgatta    6180
taaacactac acaccctctt ttaagaaagg agctaaattg ttacataaac ctattgtttg    6240
gcatgttaac aatgcaacta ataaagccac gtataaacca aatacctggt gtatacgttg    6300
tctttggagc acaaaaccag ttgaaacatc aaattcgttt gatgtactga agtcagagga    6360
cgcgcaggga atggataatc ttgcctgcga agatctaaaa ccagtctctg aagaagtagt    6420 ggaaatcct accatacaga aagacgttct tgagtgtaat gtgaaaacta ccgaagttgt    6480
aggagacatt atacttaaac cagcaaataa tagtttaaaa attacagaag aggttggcca    6540
cacagatcta atggctgctt atgtagacaa ttctagtctt actattaaga aacctaatga    6600
attatctaga gtattaggtt tgaaaacccct tgctactcat ggtttagctg ctgttaatag    6660 tgtccccttgg gatactatag ctaattatgc taagccttt cttaacaaag ttgttagtac    6720
aactactaac atagttacac ggtgtttaaa ccgtgtttgt actaattata tgccttatt    6780 ctttacttta ttgctacaat tgtgtacttt tactagaagt acaaattcta gaattaaagc    6840
atctatgccg actactatag caaagaatac tgttaagagt gtcggtaaat tttgtctaga    6900
```

```
ggcttcattt aattatttga agtcacctaa ttttctaaa ctgataaata ttataatttg    6960 gttttttacta ttaagtgttt gcctaggttc tttaatctac tcaaccgctg ctttaggtgt   7020
tttaatgtct aatttaggca tgccttctta ctgtactggt tacagagaag gctatttgaa    7080
ctctactaat gtcactattg caacctactg tactggttct ataccttgta gtgtttgtct    7140
tagtggttta gattctttag acacctatcc ttctttagaa actatacaaa ttaccatttc    7200
atcttttaaa tgggatttaa ctgcttttgg cttagttgca gagtggtttt tggcatatat    7260
tcttttcact aggttttttct atgtacttgg attggctgca atcatgcaat tgttttcag    7320 ctattttgca gtacatttta ttagtaattc ttggcttatg tggttaataa ttaatcttgt    7380
acaaatggcc ccgatttcag ctatggttag aatgtacatc ttctttgcat cattttatta    7440
tgtatggaaa agttatgtgc atgttgtaga cggttgtaat tcatcaactt gtatgatgtg    7500
ttacaaacgt aatagagcaa caagagtcga atgtacaact attgttaatg gtgttagaag    7560
gtccttttat gtctatgcta atggaggtaa aggcttttgc aaactacaca attggaattg    7620
tgttaattgt gatacattct gtgctggtag tacatttatt agtgatgaag ttgcgagaga    7680
cttgtcacta cagtttaaaa gaccaataaa tcctactgac cagtcttctt acatcgttga    7740
tagtgttaca gtgaagaatg gttccatcca tctttacttt gataaagctg gtcaaaagac    7800
ttatgaaaga cattctctct ctcattttgt taacttagac aacctgagag ctaataacac    7860
taaaggttca ttgcctatta atgttatagt ttttgatggt aaatcaaaat gtgaagaatc    7920
atctgcaaaa tcagcgtctg tttactacag tcagcttatg tgtcaaccta tactgttact    7980
agatcaggca ttagtgtctg atgttggtga tagtgcggaa gttgcagtta aaatgtttga    8040
tgcttacgtt aatacgtttt catcaacttt taacgtacca atggaaaaac tcaaaacact    8100
agttgcaact gcagaagctg aacttgcaaa gaatgtgtcc ttagacaatg tcttatctac    8160
ttttatttca gcagctcggc aagggtttgt tgattcagat gtagaaacta agatgttgt    8220 tgaatgtctt aaattgtcac atcaatctga catagaagtt actggcgata gttgtaataa    8280
ctatatgctc acctataaca agttgaaaaa catgacaccc cgtgaccttg gtgcttgtat    8340
tgactgtagt gcgcgtcata ttaatgcgca ggtagcaaaa agtcacaaca ttgctttgat    8400
atggaacgtt aaagatttca tgtcattgtc tgaacaacta cgaaaacaaa tacgtagtgc    8460
tgctaaaaag aataacttac cttttaagtt gacatgtgca actactagac aagttgttaa    8520
tgttgtaaca acaaagatag cacttaaggg tggtaaaatt gttaataatt ggttgaagca    8580
gttaattaaa gttacacttg tgttccttttt tgttgctgct attttctatt taataacacc    8640
tgttcatgtc atgtctaaac atactgactt ttcaagtgaa atcataggat acaaggctat    8700
tgatggtggt gtcactcgtg acatagcatc tacagatact tgtttttgcta acaaacatgc    8760 tgattttgac acatggttta gccagcgtgg tggtagttat actaatgaca aagcttgccc    8820
attgattgct gcagtcataa caagagaagt gggttttgtc gtgcctggtt tgcctggcac    8880
gatattacgc acaactaatg gtgactttt gcatttctta cctagagttt ttagtgcagt    8940
tggtaacatc tgttacacac catcaaaact tatagagtac actgactttg caacatcagc    9000
ttgtgttttg gctgctgaat gtacaatttt taaagatgct tctggtaagc cagtaccata    9060
ttgttatgat accaatgtac tagaaggttc tgttgcttat gaaagtttac gccctgacac    9120
acgttatgtg ctcatggatg gctctattat tcaatttcct aacacctacc ttgaaggttc    9180
tgttagagtg gtaacaactt ttgattctga gtactgtagg cacggcactt gtgaaagatc    9240
agaagctggt gtttgtgtat ctactagtgg tagatgggta cttaacaatg attattacag    9300
```

```
atctttacca ggagttttct gtggtgtaga tgctgtaaat ttacttacta atatgtttac   9360
accactaatt caacctattg gtgctttgga catatcagca tctatagtag ctggtggtat   9420
tgtagctatc gtagtaacat gccttgccta ctattttatg aggtttagaa gagcttttgg   9480
tgaatacagt catgtagttg cctttaatac tttactattc cttatgtcat tcactgtact   9540
ctgtttaaca ccagtttact cattcttacc tggtgtttat tctgttattt acttgtactt   9600
gacattttat cttactaatg atgtttcttt tttagcacat attcagtgga tggttatgtt   9660 cacacccttta gtacctttct ggataacaat tgcttatatc atttgtattt ccacaaagca   9720
tttctattgg ttctttagta attacctaaa gagacgtgta gtctttaatg gtgtttcctt   9780
tagtactttt gaagaagctg cgctgtgcac cttttttgtta aataaagaaa tgtatctaaa   9840
gttgcgtagt gatgtgctat tacctcttac gcaatataat agatacttag ctctttataa   9900
taagtacaag tattttagtg gagcaatgga tacaactagc tacagagaag ctgcttgttg  9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt tgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740 ctttaaccctt gtggctatga agtacaatta tgaacctcta acacaagacc atgttgacat  10800
actaggacct ctttctgctc aaactggaat tgccgttttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgcctttt   11100 acctttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520 gttttttggcc agaggtattg ttttttatgtg tgttgagtat tgccctattt tcttcataac  11580
tggtaataca cttcagtgta taatgctagt ttattgtttc ttaggctatt tttgtacttg  11640
```

-continued

```
ttactttggc ctctttttgtt tactcaaccg ctactttaga ctgactcttg gtgtttatga   11700
ttacttagtt tctacacagg agtttagata tatgaattca cagggactac tcccacccaa   11760
gaatagcata gatgccttca aactcaacat taaattgttg ggtgttggtg gcaaaccttg   11820
tatcaaagta gccactgtac agtctaaaat gtcagatgta aagtgcacat cagtagtctt   11880
actctcagtt ttgcaacaac tcagagtaga atcatcatct aaattgtggg ctcaatgtgt   11940
ccagttacac aatgacattc tcttagctaa agatactact gaagcctttg aaaaaatggt   12000
ttcactactt tctgttttgc tttccatgca gggtgctgta gacataaaca gctttgtga    12060
agaaatgctg acaacaggg caaccttaca agctatagcc tcagagttta gttcccttcc   12120
atcatatgca gcttttgcta ctgctcaaga agcttatgag caggctgttg ctaatggtga   12180
ttctgaagtt gttcttaaaa agttgaagaa gtctttgaat gtggctaaat ctgaatttga   12240
ccgtgatgca gccatgcaac gtaagttgga aaagatggct gatcaagcta tgacccaaat   12300
gtataaacag gctagatctg aggacaagag ggcaaaagtt actagtgcta tgcagacaat   12360
gctttttcact atgcttagaa agttggataa tgatgcactc aacaacatta tcaacaatgc   12420
aagagatggt tgtgttccct gaacataat acctcttaca acagcagcca aactaatggt   12480
tgtcatacca gactataaca catataaaaa tacgtgtgat ggtacaacat ttacttatgc   12540
atcagcattg tgggaaatcc aacaggttgt agatgcagat agtaaaattg ttcaacttag   12600
tgaaattagt atggacaatt cacctaattt agcatggcct cttattgtaa cagctttaag   12660
ggccaattct gctgtcaaat tacagaataa tgagcttagt cctgttgcac tacgacagat   12720
gtcttgtgct gccggtacta cacaaactgc ttgcactgat gacaatgcgt tagcttacta   12780
caacacaaca aagggaggta ggtttgtact tgcactgtta tccgatttac aggatttgaa   12840
atgggctaga ttccctaaga gtgatggaac tggtactatc tatacagaac tggaaccacc   12900
ttgtaggttt gttacagaca cacctaaagg tcctaaagtg aagtatttat actttattaa   12960
aggattaaac aacctaaata gaggtatggt acttggtagt ttagctgcca cagtacgtct   13020
acaagctggt aatgcaacag aagtgcctgc caattcaact gtattatctt tctgtgcttt   13080
tgctgtagat gctgctaaag cttacaaaga ttatctagct agtgggggac aaccaatcac   13140
taattgtgtt aagatgttgt gtacacacac tggtactggt caggcaataa cagttacacc   13200
ggaagccaat atggatcaag aatcctttgg tggtgcatcg tgttgtctgt actgccgttg   13260
ccacatagat catccaaatc ctaaaggatt ttgtgactta aaaggtaagt atgtacaaat   13320
acctacaact tgtgctaatg accctgtggg ttttacactt aaaaacacag tctgtaccgt   13380
ctgcggtatg tggaaaggtt atggctgtag ttgtgatcaa ctccgcgaac ccatgcttca   13440
gtcagctgat gcacaatcgt ttttaaacgg gtttgcggtg taagtgcagc ccgtcttaca   13500
ccgtgcggca caggcactag tactgatgtc gtatacaggg cttttgacat ctacaatgat   13560
aaagtagctg gttttgctaa attcctaaaa actaattgtt gtcgcttcca agaaaaggac   13620
gaagatgaca atttaattga ttcttacttt gtagttaaga gacacactt ctctaactac   13680
caacatgaag aaacaattta atttttactt aaggattgtc cagctgttgc taaacatgac   13740
ttctttaagt ttagaataga cggtgacatg gtaccacata tatcacgtca acgtcttact   13800
aaatacacaa tggcagacct cgtctatgct ttaaggcatt ttgatgaagg taattgtgac   13860
acattaaaag aaatacttgt cacatacaat tgttgtgatg atgattattt caataaaaag   13920
gactggtatg attttgtaga aaacccagat atattacgcg tatacgccaa cttaggtgaa   13980
cgtgtacgcc aagctttgtt aaaaacagta caattctgtg atgccatgcg aaatgctggt   14040
```

```
attgttggtg tactgacatt agataatcaa gatctcaatg gtaactggta tgatttcggt    14100
gatttcatac aaaccacgcc aggtagtgga gttcctgttg tagattctta ttattcattg    14160
ttaatgccta tattaacctt gaccagggct ttaactgcag agtcacatgt tgacactgac    14220
ttaacaaagc cttacattaa gtgggatttg ttaaaatatg acttcacgga agagaggtta    14280
aaactctttg accgttattt taaatattgg gatcagacat accacccaaa ttgtgttaac    14340
tgtttggatg acagatgcat tctgcattgt gcaaacttta atgttttatt ctctacagtg    14400
ttcccaccta caagttttgg accactagtg agaaaaatat tgttgatgg tgttccattt    14460
gtagtttcaa ctggatacca cttcagagag ctaggtgttg tacataatca ggatgtaaac    14520
ttacatagct ctagacttag ttttaaggaa ttacttgtgt atgctgctga ccctgctatg    14580
cacgctgctt ctggtaatct attactagat aaacgcacta cgtgcttttc agtagctgca    14640
cttactaaca atgttgcttt tcaaactgtc aaacccggta attttaacaa agacttctat    14700
gactttgctg tgtctaaggg tttctttaag gaaggaagtt ctgttgaatt aaaacacttc    14760
ttctttgctc aggatggtaa tgctgctatc agcgattatg actactatcg ttataatcta    14820
ccaacaatgt gtgatatcag acaactacta tttgtagttg aagttgttga taagtacttt    14880
gattgttacg atggtggctg tattaatgct aaccaagtca tcgtcaacaa cctagacaaa    14940
tcagctggtt ttccatttaa taaatggggt aaggctagac tttattatga ttcaatgagt    15000
tatgaggatc aagatgcact tttcgcatat acaaaacgta atgtcatccc tactataact    15060
caaatgaatc ttaagtatgc cattagtgca aagaatagag ctcgcaccgt agctggtgtc    15120
tctatctgta gtactatgac caatagacag tttcatcaaa aattattgaa atcaatagcc    15180
gccactagag gagctactgt agtaattgga acaagcaaat ctatggtgg ttggcacaac    15240
atgttaaaaa ctgtttatag tgatgtagaa aaccctcacc ttatgggttg ggattatcct    15300
aaatgtgata gagccatgcc taacatgctt agaattatgg cctcacttgt tcttgctcgc    15360
aaacatacaa cgtgttgtag cttgtcacac cgtttctata gattagctaa tgagtgtgct    15420
caagtattga gtgaaatggt catgtgtggc ggttcactat atgttaaacc aggtggaacc    15480
tcatcaggag atgccacaac tgcttatgct aatagtgttt ttaacatttg tcaagctgtc    15540
acggccaatg ttaatgcact tttatctact gatggtaaca aaattgccga taagtatgtc    15600
cgcaatttac aacacagact ttatgagtgt ctctatagaa atagagatgt tgacacagac    15660
tttgtgaatg agttttacgc atatttgcgt aaacatttct caatgatgat actctctgac    15720
gatgctgttg tgtgtttcaa tagcacttat gcatctcaag gtctagtggc tagcataaag    15780
aactttaagt cagttcttta ttatcaaaac aatgttttta tgtctgaagc aaaatgttgg    15840
actgagactg accttactaa aggacctcat gaatttgct ctcaacatac aatgctagtt    15900
aaacagggtg atgattatgt gtaccttcct tacccagatc catcaagaat cctaggggcc    15960
ggctgttttg tagatgatat cgtaaaaaca gatggtacac ttatgattga acggttcgtg    16020
tctttagcta tagatgctta cccacttact aaacatccta atcaggagta tgctgatgtc    16080
tttcatttgt acttacaata cataagaaag ctacatgatg agttaacagg acacatgtta    16140
gacatgtatt ctgttatgct tactaatgat aacacttcaa ggtattggga acctgagttt    16200
tatgaggcta tgtacacacc gcatacagtc ttacaggctg ttgggcttg tgttctttgc    16260
aattcacaga cttcattaag atgtggtgct tgcatacgta gaccattctt atgttgtaaa    16320
tgctgttacg accatgtcat atcaacatca cataaattag tcttgtctgt taatccgtat    16380
```

```
gtttgcaatg ctccaggttg tgatgtcaca gatgtgactc aactttactt aggaggtatg   16440
agctattatt gtaaatcaca taaaccaccc attagttttc cattgtgtgc taatggacaa   16500
gtttttggtt tatataaaaa tacatgtgtt ggtagcgata atgttactga ctttaatgca   16560
attgcaacat gtgactggac aaatgctggt gattacattt tagctaacac ctgtactgaa   16620
agactcaagc ttttttgcagc agaaacgctc aaagctactg aggagacatt taaactgtct   16680
tatggtattg ctactgtacg tgaagtgctg tctgacagag aattacatct ttcatgggaa   16740
gttggtaaac ctagaccacc acttaaccga aattatgtct ttactggtta tcgtgtaact   16800
aaaaacagta agtacaaat aggagagtac acctttgaaa aaggtgacta tggtgatgct   16860
gttgtttacc gaggtacaac aacttacaaa ttaaatgttg gtgattattt tgtgctgaca   16920
tcacatacag taatgccatt aagtgcacct acactagtgc cacaagagca ctatgttaga   16980
attactggct tatacccaac actcaatatc tcagatgagt tttctagcaa tgttgcaaat   17040
tatcaaaagg ttggtatgca aaagtattct acactccagg gaccacctgg tactggtaag   17100
agtcattttg ctattggcct agctctctac taccctttctg ctcgcatagt gtatacagct   17160
tgctctcatg ccgctgttga tgcactatgt gagaaggcat taaatatttt gcctatagat   17220
aaatgtagta gaattatacc tgcacgtgct cgtgtagagg ttttgataa attcaaagtg   17280 aattcaacat tagaacagta tgtctttttgt actgtaaatg cattgcctga cgacagcaga   17340
gatatagttg tctttgatga aatttcaatg gccacaaatt atgatttgag tgttgtcaat   17400
gccagattac gtgctaagca ctatgtgtac attggcgacc ctgctcaatt acctgcacca   17460
cgcacattgc taactaaggg cacactagaa ccagaatatt tcaattcagt gtgtagactt   17520
atgaaaacta taggtccaga catgttcctc ggaacttgtc ggcgttgtcc tgctgaaatt   17580
gttgacactg tgagtgcttt ggtttatgat aataagctta aagcacataa agacaaatca   17640
gctcaatgct ttaaaatgtt ttataagggt gttatcacgc atgatgtttc atctgcaatt   17700
aacaggccac aaataggcgt ggtaagagaa ttccttacac gtaaccctgc ttggagaaaa   17760 gctgtctttta tttcaccttta taattcacag aatgctgtag cctcaaagat tttgggacta   17820
ccaactcaaa ctgttgattc atcacagggc tcagaatatg actatgtcat attcactcaa   17880
accactgaaa cagctcactc ttgtaatgta aacagattta atgttgctat taccagagca   17940
aaagtaggca tactttgcat aatgtctgat agagacctttt atgacaagtt gcaatttaca   18000
agtcttgaaa ttccacgtag gaatgtggca actttacaag ctgaaaatgt aacaggactc   18060
tttaaagatt gtagtaaggt aatcactggg ttacatccta cacaggcacc tacacacctc   18120
agtgttgaca ctaaattcaa aactgaaggt ttatgtgttg acatacctgg catacctaag   18180
gacatgacct atagaagact catctctatg atgggtttta aaatgaatta tcaagttaat   18240
ggttacccta acatgtttat cacccgcgaa gaagctataa gacatgtacg tgcatggatt   18300
ggcttcgatg tcgagggggtg tcatgctact agagaagctg ttggtaccaa tttacccttta   18360 cagctaggtt tttctacagg tgttaaccta gttgctgtac ctacaggtta tgttgataca   18420
cctaataata cagattttttc cagagttagt gctaaaccac cgcctggaga tcaatttaaa   18480
cacctcatac cacttatgta caaggactt cccttggaatg tagtgcgtat aaagattgta   18540
caaatgttaa gtgacacact taaaaatctc tctgacagag tcgtatttgt cttatgggca   18600
catggctttg agttgacatc tatgaagtat tttgtgaaaa taggacctga gcgcacctgt   18660
tgtctatgtg atagacgtgc cacatgcttt tccactgctt cagacactta tgcctgttgg   18720
catcattcta ttggatttga ttacgtctat aatccgttta tgattgatgt tcaacaatgg   18780
```

```
ggttttacag gtaacctaca aagcaaccat gatctgtatt gtcaagtcca tggtaatgca   18840
catgtagcta gttgtgatgc aatcatgact aggtgtctag ctgtccacga gtgctttgtt   18900
aagcgtgttg actggactat tgaatatcct ataattggtg atgaactgaa gattaatgcg   18960
gcttgtagaa aggttcaaca catggttgtt aaagctgcat tattagcaga caaattccca   19020
gttcttcacg acattggtaa ccctaaagct attaagtgtg tacctcaagc tgatgtagaa   19080
tggaagttct atgatgcaca gccttgtagt gacaaagctt ataaaataga agaattattc   19140
tattcttatg ccacacattc tgacaaattc acagatggtg tatgcctatt ttggaattgc   19200
aatgtcgata gatatcctgc taattccatt gtttgtagat ttgacactag agtgctatct   19260
aaccttaact tgcctggttg tgatggtggc agtttgtatg taaataaaca tgcattccac   19320
acaccagctt ttgataaaag tgcttttgtt aatttaaaac aattaccatt tttctattac   19380
tctgacagtc catgtgagtc tcatggaaaa caagtagtgt cagatataga ttatgtacca   19440
ctaaagtctg ctacgtgtat aacacgttgc aatttaggtg gtgctgtctg tagacatcat   19500
gctaatgagt acagattgta tctcgatgct tataacatga tgatctcagc tggctttagc   19560
ttgtgggttt acaaacaatt tgatacttat aacctctgga acacttttac aagcttcag    19620 agtttagaaa atgtggcttt taatgttgta aataagggac actttgatgg acaacagggt   19680
gaagtaccag tttctatcat taataacact gtttacacaa aagttgatgg tgttgatgta   19740
gaattgtttg aaaataaaac aacattaccT gttaatgtag catttgagct ttgggctaag   19800
cgcaacatta aaccagtacc agaggtgaaa atactcaata atttgggtgt ggacattgct   19860
gctaatactg tgatctggga ctacaaaaga gatgctccag cacatatatc tactattggt   19920
gtttgttcta tgactgacat agccaagaaa ccaactgaaa cgatttgtgc accactcact   19980 gtctttttg atggtagagt tgatggtcaa gtagacttat ttagaaatgc ccgtaatggt   20040
gttcttatta cagaaggtag tgttaaaggt ttacaaccat ctgtaggtcc caaacaagct   20100
agtcttaatg gagtcacatt aattggagaa gccgtaaaaa cacagttcaa ttattataag   20160
aaagttgatg gtgttgtcca acaattacct gaaacttact ttactcagag tagaaattta   20220
caagaattta aacccaggag tcaaatggaa attgatttct tagaattagc tatggatgaa   20280
ttcattgaac ggtataaatt agaaggctat gccttcgaac atatcgttta tggagatttt   20340
agtcatagtc agtaggtgg tttacatcta ctgattggac tagctaaacg ttttaaggaa   20400 tcacctttg aattagaaga ttttattcct atggacagta cagttaaaaa ctatttcata   20460
acagatgcgc aaacaggttc atctaagtgt gtgtgttctg ttattgattt attacttgat   20520
gattttgttg aaataataaa atcccaagat ttatctgtag tttctaaggt tgtcaaagtg   20580
actattgact atacagaaat tcatttatgt ctttggtgta agatggcca tgtagaaaca   20640 ttttacccaa aattacaatc tagtcaagcg tggcaaccgg tgttgctat gcctaatctt   20700 tacaaaatgc aaagaatgct attagaaaag tgtgaccttc aaaattatgg tgatagtgca   20760
acattaccta aaggcataat gatgaatgtc gcaaaatata ctcaactgtg tcaatattta   20820
aacacattaa cattagctgt accctataat atgagagtta cattttgg tgctggttct   20880 gataaaggag ttgcaccagg tacagctgtt ttaagacagt ggttgcctac gggtacgctg   20940
cttgtcgatt cagatcttaa tgactttgtc tctgatgcag attcaacttt gattggtgat   21000
tgtgcaactg tacatacagc taataaatgg gatctcatta ttagtgatat gtacgaccct   21060
aagactaaaa atgttacaaa agaaaatgac tctaaagagg ttttttcac ttacatttgt   21120
```

```
gggtttatac aacaaaagct agctcttgga ggttccgtgg ctataaagat aacagaacat   21180
tcttggaatg ctgatcttta taagctcatg ggacacttcg catggtggac agcctttgtt   21240
actaatgtga atgcgtcatc atctgaagca ttttaattg gatgtaatta tcttggcaaa    21300
ccacgcgaac aaatagatgg ttatgtcatg catgcaaatt acatattttg gaggaataca   21360
aatccaattc agttgtcttc ctattcttta tttgacatga gtaaatttcc ccttaaatta   21420
aggggtactg ctgttatgtc tttaaaagaa ggtcaaatca atgatatgat tttatctctt   21480
cttagtaaag gtagacttat aattagagaa aacaacagag ttgttatttc tagtgatgtt   21540
cttgttaaca actaaacgaa caatgttgt ttttcttgtt ttattgccac tagtctctag    21600
tcagtgtgtt aatcttacaa ccagaactca attaccccct gcatacacta attctttcac   21660
acgtggtgtt tattaccctg acaaagtttt cagatcctca gttttacatt caactcagga   21720
cttgttctta ccttttcttt ccaatgttac ttggttccat gctatacatg tctctgggac   21780
caatggtact aagaggtttg ataaccctgt cctaccattt aatgatggtg tttattttgc   21840
ttccactgag aagtctaaca ataagagg ctggattttt ggtactactt tagattcgaa     21900
gacccagtcc ctacttattg ttaataacgc tactaatgtt gttattaaag tctgtgaatt   21960
tcaattttgt aatgatccat ttttgggtgt ttattaccac aaaaacaaca aaagttggat   22020
ggaaagtgag ttcagagttt attctagtgc gaataattgc acttttgaat atgtctctca   22080
gccttttctt atggaccttg aaggaaaaca gggtaatttc aaaaatctta gggaatttgt   22140
gtttaagaat attgatggtt attttaaaat atattctaag cacacgccta ttaatttagt   22200
gcgtgatctc cctcagggtt tttcggcttt agaaccattg gtagatttgc caataggtat   22260
taacatcact aggtttcaaa ctttacttgc tttacataga agttatttga ctcctggtga   22320
ttcttcttca ggttggacag ctggtgctgc agcttattat gtgggttatc ttcaacctag   22380
gacttttcta ttaaaatata tgaaaatgg aaccattaca gatgctgtag actgtgcact    22440 tgacccctc tcagaaacaa agtgtacgtt gaaatccttc actgtagaaa aggaatcta    22500 tcaaacttct aactttagag tccaaccaac agaatctatt gttagatttc ctaatattac   22560
aaacttgtgc ccttttggtg aagtttttaa cgccaccaga tttgcatctg tttatgcttg   22620
gaacaggaag agaatcagca actgtgttgc tgattattct gtcctatata attccgcatc   22680 atttttccact tttaagtgtt atggagtgtc tcctactaaa ttaaatgatc tctgctttac   22740
taatgtctat gcagattcat tgtaattag aggtgatgaa gtcagacaaa tcgctccagg   22800
gcaaactgga aagattgctg attataatta taaattacca gatgattta caggctgcgt   22860 tatagcttgg aattctaaca atcttgattc taaggttggt ggtaattata attacctgta   22920
tagattgttt aggaagtcta atctcaaacc ttttgagaga gatatttcaa ctgaaatcta   22980
tcaggccggt agcacacctt gtaatggtgt tgaaggtttt aattgttact tcccttaca    23040 atcatatggt ttccaaccca ctaatggtgt tggttaccaa ccatacagag tagtagtact   23100
ttcttttgaa cttctacatg caccagcaac tgtttgtgga cctaaaaagt ctactaattt   23160
ggttaaaaac aaatgtgtca atttcaactt caatggttta acaggcacag gtgttcttac   23220
tgagtctaac aaaaagtttc tgcctttcca acaattggc agagacattg ctgacactac   23280
tgatgctgtc cgtgatccac agacacttga gattcttgac attacaccat gttcttttgg   23340
tggtgtcagt gttataacac caggaacaaa tacttctaac caggttgctg ttctttatca   23400
ggatgttaac tgcacagaag tccctgttgc tattcatgca gatcaactta ctcctacttg   23460
gcgtgtttat tctacaggtt ctaatgtttt tcaaacacgt gcaggctgtt aatagggc    23520
```

```
tgaacatgtc aacaactcat atgagtgtga catacccatt ggtgcaggta tatgcgctag    23580
ttatcagact cagactaatt ctcctcggcg ggcacgtagt gtagctagtc aatccatcat    23640
tgcctacact atgtcacttg gtgcagaaaa ttcagttgct tactctaata actctattgc    23700
catacccaca aattttacta ttagtgttac cacagaaatt ctaccagtgt ctatgaccaa    23760
gacatcagta gattgtacaa tgtacatttg tggtgattca actgaatgca gcaatctttt    23820
gttgcaatat ggcagttttt gtacacaatt aaaccgtgct ttaactggaa tagctgttga    23880
acaagacaaa aacacccaag aagttttttgc acaagtcaaa caaatttaca aaacaccacc    23940
aattaaagat tttggtggtt ttaattttc acaaatatta ccagatccat caaaaccaag    24000
caagaggtca tttattgaag atctactttt caacaaagtg acacttgcag atgctggctt    24060
catcaaacaa tatggtgatt gccttggtga tattgctgct agagacctca tttgtgcaca    24120
aaagtttaac ggccttactg ttttgccacc tttgctcaca gatgaaatga ttgctcaata    24180
cacttctgca ctgttagcgg gtacaatcac ttctggttgg acctttggtg caggtgctgc    24240
attacaaata ccatttgcta tgcaaatggc ttataggttt aatggtattg gagttacaca    24300
gaatgttctc tatgagaacc aaaaattgat tgccaaccaa tttaatagtg ctattggcaa    24360
aattcaagac tcactttctt ccacagcaag tgcacttgga aaacttcaag atgtggtcaa    24420
ccaaaatgca caagctttaa acacgcttgt taaacaactt agctccaatt ttggtgcaat    24480
ttcaagtgtt ttaaatgata tcctttcacg tcttgacaaa gttgaggctg aagtgcaaat    24540
tgataggttg atcacaggca gacttcaaag tttgcagaca tatgtgactc aacaattaat    24600
tagagctgca gaaatcagag cttctgctaa tcttgctgct actaaaatgt cagagtgtgt    24660
acttggacaa tcaaaaagag ttgattttg tggaaagggc tatcatctta tgtccttccc    24720
tcagtcagca cctcatggtg tagtcttctt gcatgtgact tatgtccctg cacaagaaaa    24780
gaacttcaca actgctcctg ccatttgtca tgatggaaaa gcacactttc ctcgtgaagg    24840 tgtcttttgtt tcaaatggca cacactggtt tgtaacacaa aggaattttt atgaaccaca    24900
aatcattact acagacaaca catttgtgtc tggtaactgt gatgttgtaa taggaattgt    24960
caacaacaca gtttatgatc ctttgcaacc tgaattagac tcattcaagg aggagttaga    25020
taaatatttt aagaatcata catcaccaga tgttgattta ggtgacatct ctggcattaa    25080
tgcttcagtt gtaaacattc aaaaagaaat tgaccgcctc aatgaggttg ccaagaattt    25140
aaatgaatct ctcatcgatc tccaagaact tggaaagtat gagcagtata taaaatggcc    25200
atggtacatt tggctaggtt ttatagctgg cttgattgcc atagtaatgg tgacaattat    25260
gctttgctgt atgaccagtt gctgtagttg tctcaagggc tgttgttctt gtggatcctg    25320
ctgcaaattt gatgaagacg actctgagcc agtgctcaaa ggagtcaaat tacattacac    25380
ataaacgaac ttatggattt gtttatgaga atcttcacaa ttggaactgt aactttgaag    25440
caaggtgaaa tcaaggatgc tactccttca gattttgttc gcgctactgc aacgataccg    25500
atacaagcct cactcccttt cggatggctt attgttggcg ttgcacttct gctgttttt    25560 cagagcgctt ccaaaatcat aaccctcaaa aagagatggc aactagcact ctccaagggt    25620
gttcactttg tttgcaactt gctgttgttg tttgtaacag tttactcaca ccttttgctc    25680
gttgctgctg gccttgaagc ccctttctc tatctttatg ctttagtcta cttcttgcag    25740
agtataaact ttgtaagaat aataatgagg ctttggcttt gctggaaatg ccgttccaaa    25800
aacccattac tttatgatgc caactatttt ctttgctggc atactaattg ttacgactat    25860
```

```
tgtatacctt acaatagtgt aacttcttca attgtcatta cttcaggtga tggcacaaca   25920
agtcctattc tgaacatga ctaccagatt ggtggttata ctgaaaaatg ggaatctgga    25980
gtaaaagact gtgttgtatt acacagttac ttcacttcag actattacca gctgtactca   26040
actcaattga gtacagacac tggtgttgaa catgttacct tcttcatcta caataaaatt   26100
gttgatgagc ctgaagaaca tgtccaaatt cacacaatcg acggttcatc cggagttgtt   26160
aatccagtaa tggaaccaat ttatgatgaa ccgacgacga ctactagcgt gcctttgtaa   26220
gcacaagctg atgagtacga acttatgtac tcattcgttt cggaagagac aggtacgtta   26280
atagttaata gcgtacttct tttcttgct ttcgtggtat tcttgctagt tacactagcc     26340
atccttactg cgcttcgatt gtgtgcgtac tgctgcaata ttgttaacgt gagtcttgta   26400
aaaccttctt tttacgttta ctctcgtgtt aaaaatctga attcttctag agttcctgat   26460
cttctggtct aaacgaacta aatattatat tagttttct gttggaact ttaattttag      26520 ccatggcaga ttccaacggt actattaccg ttgaagagct aaaaagctc cttgaacaat    26580 ggaacctagt aataggtttc ctattcctta catggatttg tcttctacaa tttgcctatg   26640
ccaacaggaa taggttttg tatataatta agttaatttt cctctggctg ttatggccag     26700
taactttagc ttgttttgtg cttgctgctg tttacagaat aaattggatc accggtggaa   26760
ttgctatcgc aatggcttgt cttgtaggct tgatgtggct cagctacttc attgcttctt   26820
tcagactgtt tgcgcgtacg cgttccatgt ggtcattcaa tccagaaact aacattcttc   26880
tcaacgtgcc actccatggc actattctga ccagaccgct tctagaaagt gaactcgtaa    26940
tcggagctgt gatccttcgt ggacatcttc gtattgctgg acaccatcta ggacgctgtg   27000
acatcaagga cctgcctaaa gaaatcactg ttgctacatc acgaacgctt tcttattaca    27060
aattgggagc ttcgcagcgt gtagcaggtg actcaggttt tgctgcatac agtcgctaca   27120
ggattggcaa ctataaatta aacacagacc attccagtag cagtgacaat attgctttgc   27180
ttgtacagta agtgacaaca gatgtttcat ctcgttgact ttcaggttac tatagcagag   27240
atattactaa ttattatgag gacttttaaa gtttccattt ggaatcttga ttacatcata   27300
aacctcataa ttaaaatttt atctaagtca ctaactgaga ataaatattc tcaattagat   27360
gaagagcaac caatggagat tgattaaacg aacatgaaaa ttattctttt cttggcactg   27420
ataacactcg ctacttgtga gctttatcac taccaagagt gtgttagagg tacaacagta   27480 ctttttaaaag aaccttgctc ttctggaaca tacgagggca attcaccatt tcatcctcta   27540
gctgataaca aatttgcact gacttgcttt agcactcaat ttgctttgc ttgtcctgac    27600 ggcgtaaaac acgtctatca gttacgtgcc agatcagttt cacctaaact gttcatcaga   27660
caagaggaag ttcaagaact ttactctcca ttttttctta ttgttgcggc aatagtgttt   27720
ataacacttt gcttcacact caaaagaaag acagaatgat tgaactttca ttaattgact   27780
tctatttgtg cttttagcc tttctgctat tccttgtttt aattatgctt attatctttt    27840
ggttctcact tgaactgcaa gatcataatg aaacttgtca cgcctaaacg aacatgaaat   27900
ttcttgtttt cttaggaatc atcacaactg tagctgcatt tcaccaagaa tgtagtttac   27960
agtcatgtac tcaacatcaa ccatatgtag ttgatgaccc gtgtcctatt cacttctatt   28020
ctaaatggta tattagagta ggagctagaa aatcagcacc tttaattgaa ttgtgcgtgg   28080
atgaggctgg ttctaaatca cccattcagt acatcgatat cggtaattat acagtttcct   28140
gtttaccttt tacaattaat tgccaggaac ctaaattggg tagtcttgta gtgcgttgtt   28200
cgttctatga agactttta gagtatcatg acgttcgtgt tgttttagat ttcatctaaa    28260
```

```
cgaacaaact aaaatgtctg ataatggacc ccaaaatcag cgaaatgcac cccgcattac    28320
gtttggtgga ccctcagatt caactggcag taaccagaat ggagaacgca gtggggcgcg    28380
atcaaaacaa cgtcggcccc aaggtttacc caataatact gcgtcttggt tcaccgctct    28440
cactcaacat ggcaaggaag accttaaatt ccctcgagga caaggcgttc caattaacac    28500
caatagcagt ccagatgacc aaattggcta ctaccgaaga gctaccagac gaattcgtgg    28560
tggtgacggt aaaatgaaag atctcagtcc aagatggtat ttctactacc taggaactgg    28620
gccagaagct ggacttccct atggtgctaa caaagacggc atcatatggg ttgcaactga    28680
gggagccttg aatacaccaa agatcacat tggcacccgc aatcctgcta acaatgctgc    28740
aatcgtgcta caacttcctc aaggaacaac attgccaaaa ggcttctacg cagaagggag    28800
cagaggcggc agtcaagcct cttctcgttc ctcatcacgt agtcgcaaca gttcaagaaa    28860
ttcaactcca ggcagcagta ggggaacttc tcctgctaga atggctggca atggcggtga    28920
tgctgctctt gctttgctgc tgcttgacag attgaaccag cttgagagca aaatgtctgg    28980
taaaggccaa caacaacaag gccaaactgt cactaagaaa tctgctgctg aggcttctaa    29040
gaagcctcgg caaaaacgta ctgccactaa agcataacaat gtaacacaag ctttcggcag    29100
acgtggtcca gaacaaaccc aaggaaattt tggggaccag gaactaatca gacaaggaac    29160
tgattacaaa cattggccgc aaattgcaca atttgccccc agcgcttcag cgttcttcgg    29220
aatgtcgcgc attggcatgg aagtcacacc ttcgggaacg tggttgacct acacaggtgc    29280
catcaaattg gatgacaaag atccaaattt caaagatcaa gtcatttgc tgaataagca    29340 tattgacgca tacaaaacat tcccaccaac agagcctaaa aaggacaaaa agaagaaggc    29400
tgatgaaact caagccttac cgcagagaca gaagaaacag caaactgtga ctcttcttcc    29460
tgctgcagat ttggatgatt tctccaaaca attgcaacaa tccatgagca gtgctgactc    29520
aactcaggcc taaactcatg cagaccacac aaggcagatg ggctatataa acgttttcgc    29580
ttttccgttt acgatatata gtctactctt gtgcagaatg aattctcgta actacatagc    29640
acaagtagat gtagttaact ttaatctcac atagcaatct ttaatcagtg tgtaacatta    29700
gggaggactt gaaagagcca ccacattttc accgaggcca cgcggagtac gatcgagtgt    29760
acagtgaaca atgctaggga gagctgccta tatggaagag ccctaatgtg taaaattaat    29820
tttagtagtg ctatccccat gtgattttaa tagcttctta ggagaatgac aaaaaaaaaa    29880
aaaaaaaaaa aaaaaaaaaa aaa                                           29903
```

<210> SEQ ID NO 3
<211> LENGTH: 26
<212> TYPE: PRT
<213> ORGANISM: Apis mellifera

<400> SEQUENCE: 3

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 4
<211> LENGTH: 37
<212> TYPE: PRT
<213> ORGANISM: Homo sapiens

<400> SEQUENCE: 4

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
                35

<210> SEQ ID NO 5
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(29)
<223> OTHER INFORMATION: a, c, t, g, unknown or other
<220> FEATURE:
<221> NAME/KEY: modified_base
<222> LOCATION: (37)..(65)
<223> OTHER INFORMATION: a, c, t, g, unknown or other

<400> SEQUENCE: 5
nnnnnnnnnn nnnnnnnnnn nnnnnnnnnt caagagnnnn nnnnnnnnnn nnnnnnnnnn    60
nnnnnttttt tg                                                        72
```